United States Patent
Westman

(10) Patent No.: US 9,963,455 B2
(45) Date of Patent: May 8, 2018

(54) PYRAZOLO[1,5-A]PYRIMIDINES AS ANTIVIRAL COMPOUNDS

(71) Applicant: Curovir AB, Kalmar (SE)

(72) Inventor: Jacob Westman, Jarlasa (SE)

(73) Assignee: Curovir AB, Kalmar (SE)

(*) Notice: Subject to any disclaimer, the term of this patent is extended or adjusted under 35 U.S.C. 154(b) by 0 days. days.

(21) Appl. No.: 15/107,930

(22) PCT Filed: Jan. 21, 2015

(86) PCT No.: PCT/EP2015/051177
§ 371 (c)(1),
(2) Date: Jun. 24, 2016

(87) PCT Pub. No.: WO2015/110491
PCT Pub. Date: Jul. 30, 2015

(65) Prior Publication Data
US 2016/0318937 A1    Nov. 3, 2016

(30) Foreign Application Priority Data

Jan. 22, 2014 (EP) .................................... 14152202

(51) Int. Cl.
*C07D 487/04* (2006.01)
*A61K 31/519* (2006.01)

(52) U.S. Cl.
CPC .......... *C07D 487/04* (2013.01); *A61K 31/519* (2013.01)

(58) Field of Classification Search
None
See application file for complete search history.

(56) References Cited

U.S. PATENT DOCUMENTS

| | | | |
|---|---|---|---|
| 6,313,124 B1 | 11/2001 | He et al. | |
| 7,879,862 B2 * | 2/2011 | Lanier .................. | C07D 487/04 514/259.3 |
| 8,633,198 B1 | 1/2014 | Niazi et al. | |
| 2007/0072880 A1 | 3/2007 | Guzi et al. | |

FOREIGN PATENT DOCUMENTS

| | | | | |
|---|---|---|---|---|
| EP | 0 591 528 A1 | 4/1994 | | |
| JP | 03204877 A * | 9/1991 | ............ | C07D 487/04 |
| WO | WO 01/23387 A2 * | 4/2001 | ............ | C07D 487/00 |
| WO | 2010/086040 A1 | 8/2010 | | |

OTHER PUBLICATIONS

Database CAPLUS in STN, Acc. No. 1992:6580, Inoue et al., JP 03204877 A (Sep. 6, 1991) (abstract).*
Database CAPLUS in STN, Acc. No. 2001:247336, Darrow et al., WO 2001023387 A2 (Apr. 5, 2001) (abstract).*
International Search Report for corresponding International Application No. PCT/EP2015/051177 dated Jul. 13, 2015.
Written Opinion of the International Searching Authority for corresponding International Application No. PCT/EP2015/051177 dated Jul. 13, 2015.
Database Registry [Online] Chemical Abstracts Service, Columbus, Ohio, US; Jul. 25, 2006 (Jul. 25, 2006), XP002737844, retrieved from stn accession No. 896080-H.I-7, Database accession No. 896080-10-7, abstract.
Database Registry [Online] Chemical Abstracts Service, Columbus, Ohio, US; Jun. 29, 2008 (Jun. 29, 2008), XP002737845, accession No. 1031626-91-1, Database accession No. 1031626-91-1 1031598-41-0; abstract.
Database Registry [Online] Chemical Abstracts Service, Columbus, Ohio, US; Jul. 5, 2006 (Jul. 5, 2006), XP002737846, retrieved from stn accession No. 890638-53-6, Database accessionNo. 890638-53-6, abstract.
Database Registry [Online] Chemical Abstracts Service, Columbus, Ohio, US; Oct. 11, 2007 (Oct. 11, 2007), XP802737847, accession No. 950365-69-2, Database accession No. 950365-69-2, abstract.
Arita et al., "Phosphatidylinositol 4-Kinase III Beta is a Target of Enviroxime-Like Compounds for Antipoliovirus Activity", Journal of Virology, vol. 85, No. 5, Mar. 2011, pp. 2364-2372.
Hwang et al., "Discovery and characterization of a novel 7-aminopyrazolo[1,5-a]pyrimidine analog as a potent hepatitis C virus inhibitor", Bioorganic & Medicinal Chemistry Letters, vol. 22, 2012, pp. 7297-7301.
Tellew et al., "Discovery of NB1-77860/GSK561679, a potent corticotropin-releasing factor (CRF1) receptor antagonist with improved pharmacokinetic properties", Bioorganic & Medicinal Chemistry Letters, vol. 20, 2010, pp. 1259-7264.
Reynolds et al., "High throughput screening of a library based on kinase inhibitor scaffolds against *Mycobacterium tuberculosis* H37Rv", Tuberculois, vol. 92, 2012, pp. 72-83.
Bianco et al., "Metabolism of Phosphatidylinositol 4-Kinase IIIa-Dependent PI4P is Subverted by HCV and is Targeted by a 4-Anilino Quinazoline with Antiviral Activity", PLoS Pathogens, vol. 8, Issue 3, Mar. 2012, pp. 1-17.
Labroli et al., "Discovery of pyrazolo[1,5-a]pyrimidine-based CHKI inhibitors: A template-based approach—Part 2", Biiorganic & Medicinal Chemistry Letters, vol. 21, 2011, pp. 471-474.
Van Der Shaar et al., "A Novel, Broad-Spectrum Inhibitor of Enterovirus Replication That Targets Host Cell Factor Phosphatidylinositol 4-Kinase III-beta", Antimicrobial Agents and Chemotherapy, vol. 57, No. 10, Oct. 2013, pp. 1971-4981.

(Continued)

Primary Examiner — Brian J Davis
(74) Attorney, Agent, or Firm — Renner, Otto, Boisselle & Sklar, LLP

(57) ABSTRACT

A compound of formula (I) or a pharmaceutically acceptable salt thereof, useful in therapy, in particular in the treatment of a viral infection.

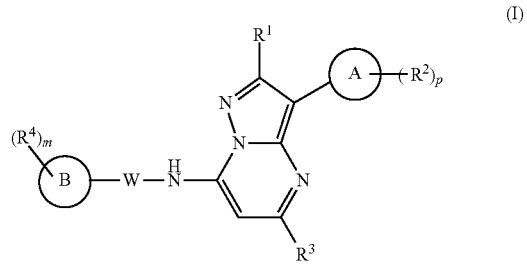

(I)

21 Claims, 1 Drawing Sheet

(56) References Cited

OTHER PUBLICATIONS

LaMarche et al., "Anti-Hepatitis C Virus Activity and Toxicity of Type III Phosphatidylinositol-4-Kinase Beta Inhibitors", Antimicrobial Agents and Chemotherapy, vol. 56, No. 10, Oct. 2012, pp. 5149-5156.

Yang et al., "Phosphatidylinositol 4-Kinase III-beta Is Required for Severe Acute Respiratory Syndrome Coronavirus Spike-mediated Cell Entry", The Journal of Biological Chemistry, vol. 287, No. 11, Mar. 9, 2012, pp. 8457-8467.

MacLeod et al., "Identification of a Series of Compounds with Potent Antiviral Activity for the Treatment of Enterovirus Infections", ACS Medicinal Chemistry Letters, vol. 4, 2013, pp. 585-589.

Gudmundsson et al., "Pyrazolopyrimidines and pyrazolotriazines with potent activity against herpesviruses", Bioorganic & Medicinal Chemistry Letters, vol. 19, 2009, pp. 5689-5692.

Decor et al., "Design, synthesis and biological evaluation of novel aminothiazoles as antiviral compounds acting against human rhinovirus", Bioorganic & Medicinal Chemistry Letters, vol. 23, 2013, pp. 3841-3847.

Griffith et al., "Discovery and evaluation of pyrazolo[t,5-a]pyrimidines as neuropeptide Y1 receptor antagonists", Bioorganic & Medicinal Chemistry Letters, vol. 21, 2011, pp. 2641-2645.

Chen et al., "Optimization of 3-phenylpyrazolo[1,5-a]pyrimidines as potent corticotropin-releasing factor-1 antagonists with adequate lipophilicity and water solubility", Bioorganic & Medicinal Chemistry Letters, vol. 14, 2004, pp. 3669-3673.

Gilligan et al., "-(4-Methoxyphenyl)pyrazolo[115-a]-1,3,5-triazines: Selective and Centrally Active Corticotropin-Releasing Factor Receptor-1 (CRF1) Antagonists", Journal of Medicinal Chemistry, vol. 52, No. 9, 2009, pp. 3073-3083.

Majo et al., "Facile Palladium-Catalyzed Synthesis of 3-Arylpyrazolo-[1,5-a]pyrimidines", Adv. Synth. Catal., vol. 345, 2003, pp. 620-624.

\* cited by examiner

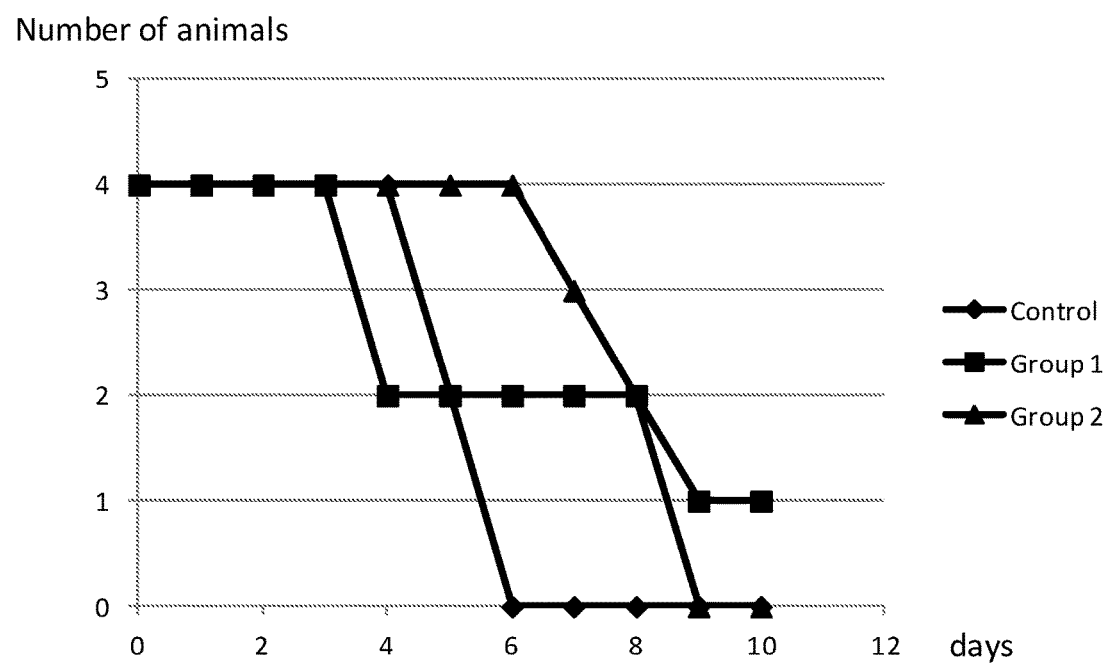

PYRAZOLO[1,5-A]PYRIMIDINES AS ANTIVIRAL COMPOUNDS

This application is a national phase of International Application No. PCT/EP2015/051177 filed Jan. 21, 2015 and claims priority to European Patent Application No. 14152202.9 filed on Jan. 22, 2014.

FIELD OF THE INVENTION

The present invention relates generally to compounds having usefulness in therapy, in particular in the treatment of conditions caused by certain viruses, such as diabetes, cancer, neurodegenerative diseases such as Alzheimer's disease and amyotrophic lateral sclerosis. More particularly the invention relates to pyrazolo[1,5-a]pyrimidin-7-amine derivatives for use in therapy.

BACKGROUND OF THE INVENTION

Pyrazolo[1,5-a]pyrimidine is a commonly used scaffold in medicinal chemistry and derivatives thereof are known for their potent utility as analgesics, benzodiazepine receptor antagonists, angiotensin II receptor antagonists, angiogenesis inhibitors, anti-inflammatory agents, neuropeptide Y receptor antagonists, COX2-inhibitor and corticotrophin-releasing hormone receptor type 1 antagonists and as CHK1 inhibitors (e.g. Mayo et al (Adv. Synth. Catal. 2003, 345, 620-624; Tellew et al (Bioorg. Med. Chem. Lett. 2010, 20, 7259-7264); Chen et al (Bioorg. Med. Chem. Lett. 2004, 14, 3669-3673); Labroli et al (Bioorg. Med. Chem. Lett. 2011, 21, 471-474); Griffith et al (Bioorg. Med. Chem. Lett. 2011, 21, 2641-2645); Gilligan et al, (J. Med. Chem. 2009, 52, 3073-3083); He et al. (U.S. Pat. No. 6,313,124 B1); and Wren et al. (WO 2010/086040).

The scaffold has also been described in phosphatidylinositol 4-kinase (PI4K) inhibitors. Bianco et al (PLoS Pathogens, 2012, 8(3), 1-17) and LaMarche et al (Antimicr. Agents and Chemother. 2012, 56(10), 5149-5156) have shown that PI4K is important for hepatitis C virus (HCV) replication and Yang et al (J. Biol. Chem. 2012, 287(11), 8547-8467) have shown the same for coronavirus. McLeod et al (ACS Med. Chem. Lett. 2013, 4(7), 585-589) and van der Schaar et al (Antimicrobial Agents Chemother. 2013, 57(10), 4971-4981) have shown some imidazopyrazines derivatives inhibiting PI4K that are potent antivirals towards picornavirus.

Gudmundsson et al (Bioorg. Med. Chem. Lett. 2009, 19, 5689-5692) have disclosed some 3-arylpyrazolo[1,5-a]pyrimidines with potent activity against herpesviruses.

Hwang et al (Bioorg. Med. Chem. Lett. 2012, 22, 7297-7301) have described 3-arylpyrazolo[1,5-a]pyrimidines as PI4K inhibitors that have anti-HCV effects.

Décor et al (Bioorg Med Chem Lett. 2013, 23, 3841-7) have also shown that PI4K is important for enterovirus replication. However, they have also shown that PI4K inhibitors (non 3-arylpyrazolo[1,5-a]pyrimidines) and the 3-arylpyrazolo[1,5-a]pyrimidine 3-(3,4-dimethoxyphenyl)-2,5-dimethyl-N-(2-morpholinoethyl)pyrazolo[1,5-a]pyrimidin-7-amine (called T-00127-HEV1) when tested in-vivo induced mortality in mice, which raised doubts on the safety of inhibiting PI4K.

SUMMARY OF THE INVENTION

One aspect is a compound of formula (I)

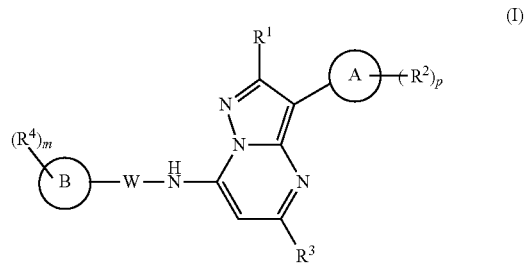

(I)

or a pharmaceutically acceptable salt thereof, wherein W is

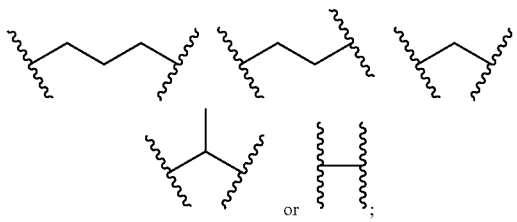

p is an integer of from 0 to 3;
$R^1$ is H or C1-C6 alkyl;
ring A is phenyl or 5- or 6-membered heteroaryl;
when ring A is phenyl, said phenyl is not substituted in ortho position;
each $R^2$ is independently selected from C1-C6 alkyl, $R^5O-$, $R^6R^7NC(O)-$, $R^9C(O)N(R^8)-$, $R^{10}OC(O)-$, $R^{11}C(O)O-$, and halogen;
  $R^5$, $R^6$, $R^7$ and $R^8$ are independently selected from H and C1-C6 alkyl;
  $R^9$, $R^{10}$ and $R^{11}$ are independently selected from C1-6 alkyl;
  any alkyl is optionally substituted by one or more F; or
two $R^2$ attached to adjacent carbon atoms together form a methylenedioxy or ethylenedioxy biradical;
$R^3$ is C1-C6 alkyl; and
m is an integer of from 0 to 2;
each $R^4$ is independently selected from C1-C6 alkyl, $R^{12}O$, halogen, $R^{13}R^{14}NC(O)-$, $R^{16}C(O)N(R^{15})-$, $R^{17}OC(O)-$, $R^{18}C(O)O-$, $R^{19}S(O)_2-$, $R^{20}S(O)_2N(H)-$, $NH_2S(O)_2-$, $R^{21}C(O)-$, $N(R^{22})(R^{23})-$, and $^-O-$;
  $R^{12}$, $R^{13}$, $R^{14}$, $R^{15}$, $R^{22}$, and $R^{23}$ are independently selected from H and C1-C6 alkyl,
  $R^{16}$, $R^{17}$, $R^{18}$, $R^{19}$, $R^{20}$, and $R^{21}$ are independently selected from C1-6 alkyl; any alkyl is optionally substituted by one or more F; or
two $R^4$ attached to adjacent atoms of ring B form, together with the atoms to which they are attached, a 5- or 6-membered heterocyclic or carbocyclic ring;
ring B is 5- or 6-membered saturated or unsaturated carbocyclyl, 5- or 6-membered heteroaryl, or phenyl;
for use in therapy,
provided that the compound is not:
3-(4-chlorophenyl)-N-(4-methoxyphenyl)-5-methylpyrazolo[1,5-a]pyrimidin-7-amine,
N-(cyclohexylmethyl)-2,5-dimethyl-3-(p-tolyl)pyrazolo[1,5-a]pyrimidin-7-amine,
2,5-dimethyl-N-phenyl-3-(p-tolyl)pyrazolo[1,5-a]pyrimidin-7-amine,
N-benzyl-2,5-dimethyl-3-(p-tolyl)pyrazolo[1,5-a]pyrimidin-7-amine, or 2,5-dimethyl-N-phenethyl-3-(p-tolyl)pyrazolo[1,5-a]pyrimidin-7-amine.

Some of the compounds according to formula (I) as defined herein above are novel. Thus, another aspect is a novel compound of formula (Id)

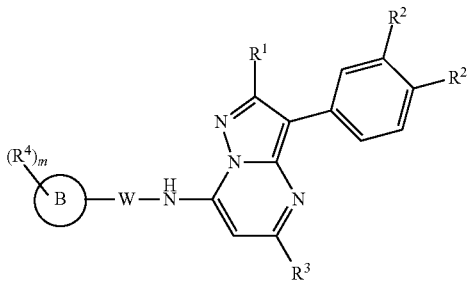

(Id)

or a pharmaceutically acceptable salt thereof, wherein
W is

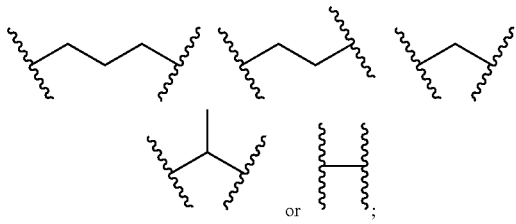

$R^1$ is H or C1-C6 alkyl,
each $R^2$ is independently selected from C1-C6 alkyl, $R^5O$—, $R^6R^7NC(O)$—, $R^9C(O)N(R^8)$—, $R^{10}OC(O)$—, $R^{11}C(O)O$—, and halogen;
  $R^5$, $R^6$, $R^7$ and $R^8$ are independently selected from H and C1-C6 alkyl;
  $R^9$, $R^{10}$ and $R^{11}$ are independently selected from C1-6 alkyl;
  any alkyl is optionally substituted by one or more F; or two $R^2$ together form a methylenedioxy or ethylenedioxy biradical;
$R^3$ is C1-C6 alkyl;
m is an integer of from 0 to 2;
each $R^4$ is independently selected from C1-C6 alkyl, $R^{12}O$, halogen, $R^{13}R^{14}NC(O)$—, $R^{16}C(O)N(R^{15})$—, $R^{17}OC(O)$—, $R^{18}C(O)O$—, $R^{19}S(O)_2$—, $R^{20}S(O)_2N(H)$—, $NH_2S(O)_2$—, $R^{21}C(O)$—, $N(R^{22})(R^{23})$—, and ⁻O—;
  $R^{12}$, $R^{13}$, $R^{14}$, $R^{15}$, $R^{22}$, and $R^{23}$ are independently selected from H and C1-C6 alkyl,
  $R^{16}$, $R^{17}$, $R^{18}$, $R^{19}$, $R^{20}$, and $R^{21}$ are independently selected from C1-6 alkyl;
  any alkyl is optionally substituted by one or more F; or two $R^4$ attached to adjacent atoms of ring B form, together with the atoms to which they are attached, a 5- or 6-membered heterocyclic or carbocyclic ring;
ring B is 5- or 6-membered heteroaryl, or phenyl;
provided that the compound is not:
N-[(4-chlorophenyl)methyl]-3-(3,4-dimethoxyphenyl)-2,5-dimethyl-pyrazolo[1,5-a]pyrimidin-7-amine,
3-(3,4-dimethoxyphenyl)-N-[(4-methoxyphenyl)methyl]-2,5-dimethyl-pyrazolo[1,5-a]pyrimidin-7-amine,
N-[2-(4-chlorophenyl)ethyl]-3-(3,4-dimethoxyphenyl)-2,5-dimethyl-pyrazolo[1,5-a]pyrimidin-7-amine,
3-(3,4-dimethoxyphenyl)-2,5-dimethyl-N-(p-tolylmethyl)pyrazolo[1,5-a]pyrimidin-7-amine,
3-(3,4-dimethoxyphenyl)-2,5-dimethyl-N-(3-phenylpropyl)pyrazolo[1,5-a]pyrimidin-7-amine,
N-(1,3-benzodioxol-5-ylmethyl)-3-(3,4-dimethoxyphenyl)-2,5-dimethyl-pyrazolo[1,5-a]pyrimidin-7-amine,
3-(3,4-dimethoxyphenyl)-N-[(4-fluorophenyl)methyl]-2,5-dimethyl-pyrazolo[1,5-a]pyrimidin-7-amine,
3-(3,4-dimethoxyphenyl)-2,5-dimethyl-N-(2-phenylpropyl)pyrazolo[1,5-a]pyrimidin-7-amine,
3-(3,4-dimethoxyphenyl)-N-[2-(2,4-dimethoxyphenyl)ethyl]-2,5-dimethyl-pyrazolo[1,5-a]pyrimidin-7-amine,
3-(3,4-dimethoxyphenyl)-2,5-dimethyl-N-(2-pyridylmethyl)pyrazolo[1,5-a]pyrimidin-7-amine,
N-benzyl-3-(3,4-dimethoxyphenyl)-2,5-dimethyl-pyrazolo[1,5-a]pyrimidin-7-amine,
N-(4-bromophenyl)-3-(3,4-dimethoxyphenyl)-2,5-dimethyl-pyrazolo[1,5-a]pyrimidin-7-amine,
N-(4-chlorophenyl)-3-(3,4-dimethoxyphenyl)-2,5-dimethyl-pyrazolo[1,5-a]pyrimidin-7-amine,
3-(3,4-dimethoxyphenyl)-2,5-dimethyl-N-(p-tolyl)pyrazolo[1,5-a]pyrimidin-7-amine,
3-(3,4-dimethoxyphenyl)-N-(4-methoxyphenyl)-2,5-dimethyl-pyrazolo[1,5-a]pyrimidin-7-amine,
3-(3,4-dimethoxyphenyl)-2,5-dimethyl-N-(m-tolyl)pyrazolo[1,5-a]pyrimidin-7-amine,
N-(3-chlorophenyl)-3-(3,4-dimethoxyphenyl)-2,5-dimethyl-pyrazolo[1,5-a]pyrimidin-7-amine,
3-(3,4-dimethoxyphenyl)-N-(3,4-dimethylphenyl)-2,5-dimethyl-pyrazolo[1,5-a]pyrimidin-7-amine,
3-(3,4-dimethoxyphenyl)-N-(4-fluorophenyl)-2,5-dimethyl-pyrazolo[1,5-a]pyrimidin-7-amine,
3-(3,4-dimethoxyphenyl)-N-(4-ethoxyphenyl)-2,5-dimethyl-pyrazolo[1,5-a]pyrimidin-7-amine,
N-(3-chloro-4-methyl-phenyl)-3-(3,4-dimethoxyphenyl)-2,5-dimethyl-pyrazolo[1,5-a]pyrimidin-7-amine,
3-(3,4-dimethoxyphenyl)-N-(3,5-dimethylphenyl)-2,5-dimethyl-pyrazolo[1,5-a]pyrimidin-7-amine,
3-(3,4-dimethoxyphenyl)-2,5-dimethyl-N-phenyl-pyrazolo[1,5-a]pyrimidin-7-amine,
N-[4-[[3-(3,4-dimethoxy phenyl)-2,5-dimethyl-pyrazolo[1,5-a]pyrimidin-7-yl]amino]phenyl]acetamide
N-(3,4-dichlorophenyl)-3-(3,4-dimethoxyphenyl)-2,5-dimethyl-pyrazolo[1,5-a]pyrimidin-7-amine,
3-(3,4-dimethoxyphenyl)-N-(4-isopropylphenyl)-2,5-dimethyl-pyrazolo[1,5-a]pyrimidin-7-amine,
3-(3,4-dimethoxyphenyl)-N-(3-methoxyphenyl)-2,5-dimethyl-pyrazolo[1,5-a]pyrimidin-7-amine
3-(3,4-dimethoxyphenyl)-N-(4-ethylphenyl)-2,5-dimethyl-pyrazolo[1,5-a]pyrimidin-7-amine,
N-(4-butylphenyl)-3-(3,4-dimethoxyphenyl)-2,5-dimethyl-pyrazolo[1,5-a]pyrimidin-7-amine, or
N-(3,5-dichlorophenyl)-3-(3,4-dimethoxyphenyl)-2,5-dimethyl-pyrazolo[1,5-a]pyrimidin-7-amine.

Still another aspect is a novel compound of formula (Ih)

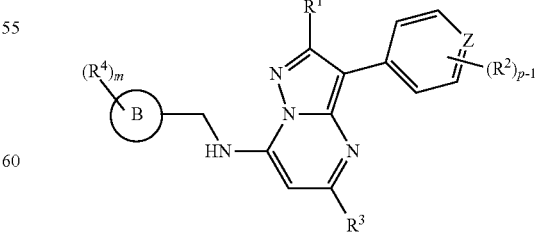

(Ih)

or a pharmaceutically acceptable salt thereof, wherein
p is an integer of from 1 to 3;
$R^1$ is H or C1-C6 alkyl;
Z is N or $CR^2$ each R² is independently selected from C1-C6 alkyl, R⁵O—, R⁶R⁷NC(O)—, R⁹C(O)N(R⁸)—, R¹⁰OC(O)—, R¹¹C(O)O—, and halogen;
  R⁵, R⁶, R⁷ and R⁸ are independently selected from H and C1-C6 alkyl;
  R⁹, R¹⁰ and R¹¹ are independently selected from C1-6 alkyl;
  any alkyl is optionally substituted by one or more F; or two R² together form a methylenedioxy or ethylenedioxy biradical;
no R² is attached in ortho position on the phenyl ring;
R³ is C1-C6 alkyl;
m is an integer of from 0 to 2;
each R⁴ is independently selected from C1-C6 alkyl, R¹²O, halogen, R¹³R¹⁴NC(O)—, R¹⁶C(O)N(R¹⁵)—, R¹⁷OC(O)—, R¹⁸C(O)O—, R¹⁹S(O)₂—, R²⁰S(O)₂N(H)—, NH₂S(O)₂—, R²¹C(O)—, N(R²²)(R²³)—, and ⁻O—;
  R¹², R¹³, R¹⁴, R¹⁵, R²², and R²³ are independently selected from H and C1-C6 alkyl,
  R¹⁶, R¹⁷, R¹⁸, R¹⁹, R²⁰, and R²¹ are independently selected from C1-6 alkyl;
  any alkyl is optionally substituted by one or more F; or two R⁴ attached to adjacent atoms of ring B form, together with the atoms to which they are attached, a 5- or 6-membered heterocyclic or carbocyclic ring;
ring B is 5- or 6-membered heteroaryl, or phenyl;
provided that the compound is not:
N-benzyl-2,5-dimethyl-3-(p-tolyl)pyrazolo[1,5-a]pyrimidin-7-amine,
3-(4-methoxyphenyl)-2,5-dimethyl-N-(pyridin-3-ylmethyl)pyrazolo[1,5-a]pyrimidin-7-amine,
3-(4-methoxyphenyl)-2,5-dimethyl-N-(pyridin-4-ylmethyl)pyrazolo[1,5-a]pyrimidin-7-amine,
N-[(4-chlorophenyl)methyl]-3-(3,4-dimethoxyphenyl)-2,5-dimethyl-pyrazolo[1,5-a]pyrimidin-7-amine,
3-(3,4-dimethoxyphenyl)-N-[(4-methoxyphenyl)methyl]-2,5-dimethyl-pyrazolo[1,5-a]pyrimidin-7-amine,
3-(3,4-dimethoxyphenyl)-2,5-dimethyl-N-(p-tolylmethyl)pyrazolo[1,5-a]pyrimidin-7-amine,
N-(1,3-benzodioxol-5-ylmethyl)-3-(3,4-dimethoxyphenyl)-2,5-dimethyl-pyrazolo[1,5-a]pyrimidin-7-amine,
3-(3,4-dimethoxyphenyl)-N-[(4-fluorophenyl)methyl]-2,5-dimethyl-pyrazolo[1,5-a]pyrimidin-7-amine,
N-benzyl-3-(4-fluorophenyl)-2,5-dimethyl-pyrazolo[1,5-a]pyrimidin-7-amine,
N-benzyl-3-(4-fluorophenyl)-5-methyl-pyrazolo[1,5-a]pyrimidin-7-amine,
N-benzyl-3-(4-chlorophenyl)-5-methyl-pyrazolo[1,5-a]pyrimidin-7-amine,
2,5-dimethyl-3-(p-tolyl)-N-(2-pyridylmethyl)pyrazolo[1,5-a]pyrimidin-7-amine,
2,5-dimethyl-3-(p-tolyl)-N-(3-pyridylmethyl)pyrazolo[1,5-a]pyrimidin-7-amine,
3-(3,4-dimethoxyphenyl)-2,5-dimethyl-N-(2-pyridylmethyl)pyrazolo[1,5-a]pyrimidin-7-amine,
3-(4-fluorophenyl)-2,5-dimethyl-N-(3-pyridylmethyl)pyrazolo[1,5-a]pyrimidin-7-amine,
3-(4-fluorophenyl)-2,5-dimethyl-N-(2-pyridylmethyl)pyrazolo[1,5-a]pyrimidin-7-amine,
N-benzyl-3-(3,4-dimethoxyphenyl)-2,5-dimethyl-pyrazolo[1,5-a]pyrimidin-7-amine,
3-(4-chlorophenyl)-2,5-dimethyl-N-(2-pyridylmethyl)pyrazolo[1,5-a]pyrimidin-7-amine,
3-(4-chlorophenyl)-2,5-dimethyl-N-(3-pyridylmethyl)pyrazolo[1,5-a]pyrimidin-7-amine,
3-(4-methoxyphenyl)-2,5-dimethyl-N-(3-pyridylmethyl)pyrazolo[1,5-a]pyrimidin-7-amine, or
3-(4-methoxyphenyl)-2,5-dimethyl-N-(4-pyridylmethyl)pyrazolo[1,5-a]pyrimidin-7-amine.

Another aspect is a compound of formula (Id) or of formula (Ih) for use in therapy.

Another aspect is a compound of formula (I), as defined herein, or a compound of formula (Id), or a compound of formula (Ih), for use in the treatment of a viral infection, e.g. an RNA viral infection.

Another aspect is a compound of formula (I)

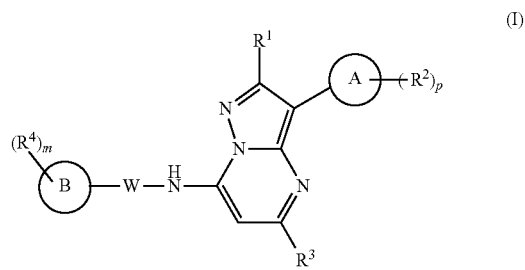

(I)

or a pharmaceutically acceptable salt thereof, wherein
W is

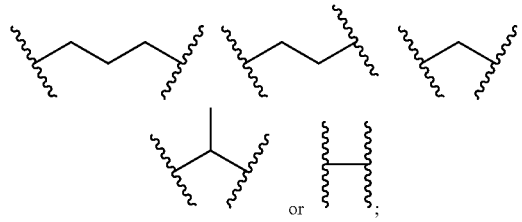

p is an integer of from 0 to 3,
R¹ is H or C1-C6 alkyl,
ring A is phenyl or 5- or 6-membered heteroaryl;
when ring A is phenyl, said phenyl is not substituted in ortho position;
each R² is independently selected from C1-C6 alkyl, R⁵O—, R⁶R⁷NC(O)—, R⁹C(O)N(R⁸)—, R¹⁰OC(O)—, R¹¹C(O)O—, and halogen;
  R⁵, R⁶, R⁷ and R⁸ are independently selected from H and C1-C6 alkyl;
  R⁹, R¹⁰ and R¹¹ are independently selected from C1-6 alkyl;
  any alkyl is optionally substituted by one or more F; or two R² attached to adjacent carbon atoms together form a methylenedioxy or ethylenedioxy biradical;
R³ is C1-C6 alkyl;
m is an integer of from 0 to 2;
each R⁴ is independently selected from C1-C6 alkyl, R¹²O, halogen, R¹³R¹⁴NC(O)—, R¹⁶C(O)N(R⁵)—, R¹⁷OC(O)—, R¹⁸C(O)O—, R¹⁹S(O)₂—, R²⁰S(O)₂N(H)—, NH₂S(O)₂—, R²¹C(O)—, N(R²²)(R²³)—, and ⁻O—;
  R¹², R¹³, R¹⁴, R¹⁵, R²², and R²³ are independently selected from H and C1-C6 alkyl,
  R¹⁶, R¹⁷, R¹⁸, R¹⁹, R²⁰, and R²¹ are independently selected from C1-6 alkyl;
  any alkyl is optionally substituted by one or more F; or two R⁴ attached to adjacent atoms of ring B form, together with the atoms to which they are attached, a 5- or 6-membered heterocyclic or carbocyclic ring, or a benzene ring;

ring B is 5- or 6-membered saturated or unsaturated carbocyclyl, 5- or 6-membered heteroaryl, or phenyl;
for use in the treatment of a viral infection,
provided that the compound is not:
N-(cyclohexylmethyl)-2,5-dimethyl-3-(p-tolyl)pyrazolo[1,5-a]pyrimidin-7-amine,
2,5-dimethyl-N-phenyl-3-(p-tolyl)pyrazolo[1,5-a]pyrimidin-7-amine,
N-benzyl-2,5-dimethyl-3-(p-tolyl)pyrazolo[1,5-a]pyrimidin-7-amine, or
2,5-dimethyl-N-phenethyl-3-(p-tolyl)pyrazolo[1,5-a]pyrimidin-7-amine.

In some embodiments, the viral infection is a non-enveloped single-stranded (+) RNA viral infection.

BRIEF DESCRIPTION OF THE DRAWINGS

The FIGURE is a diagram showing the number of surviving animals as a function of the number of days after infections with Coxsackie B3 virus, in mice treated with the compound of Ex. 9, 200 mg/kg once daily per orally starting on day 1 (group 1) or on day 3 (group 2), and in mice treated with vehicle only (0.4% Tween 80, 2% glycerol and 15% β-hydroxypropyl cyclodextrin).

DETAILED DESCRIPTION OF THE INVENTION

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

Unless otherwise stated or indicated, the term "C1-6 alkyl" denotes a straight or branched alkyl group having from 1 to 6 carbon atoms. Examples of said C1-6 alkyl include methyl, ethyl, n-propyl, iso-propyl, n-butyl, iso-butyl, sec-butyl, t-butyl and straight- and branched-chain pentyl and hexyl.

The term "C1-C6 hydroxyalkyl" refers to a C1-C6 alkyl substituted with one OH. An example of a C1-C6 hydroxyalkyl is hydroxymethyl: —CH$_2$OH.

Unless otherwise stated or indicated, the term "halogen" (or "halo") refers to fluorine (F), chlorine (Cl), or bromine (Br).

A moiety of the type R'R"NC(O)— is a moiety of formula

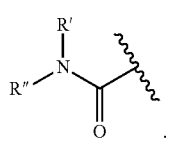

A moiety of the type R"C(O)N(R')— is a moiety of formula

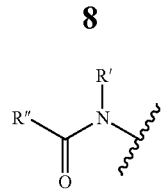

A moiety of the type R'OC(O)— is a moiety of formula

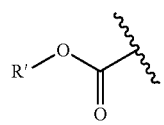

A moiety of the type R'C(O)O— is a moiety of formula

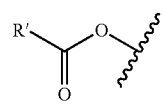

A moiety of the type R'S(O)$_2$— is a moiety of formula

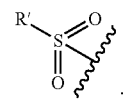

A moiety of the type R'S(O)$_2$N(H)— is a moiety of formula

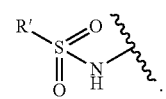

A moiety of the type NH$_2$S(O)$_2$— is a moiety of formula

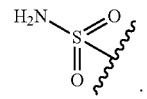

A moiety of the type R'C(O)— is a moiety of formula

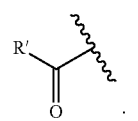

A moiety of the type N(R')(R")— is a moiety of formula

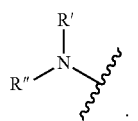

As used herein, the term "carbocyclic ring" refers to a saturated or unsaturated (e.g. monounsaturated or diunsaturated), non-aromatic cyclic moiety containing only carbon atoms in the ring, such as hexyl or hexenyl.

The term "heterocyclic ring" refers to a saturated or unsaturated, non-aromatic cyclic moiety containing not only carbon atoms, but also at least one other atom in the ring, e.g. selected from nitrogen (N), sulphur (S) and oxygen (O), in particular N and O; such as piperidinyl, or 1,2,3,4-tetrahydropyridinyl. Other examples of heterocyclyl include morpholinyl, pyrrolidinyl, piperazinyl, tetrahydrothienyl, and tetrahydrofuryl.

The term "heteroaryl" refers to an aromatic ring containing at least one ring heteroatom, such as furyl, isoxazolyl, isothiazolyl, imidazolyl, pyridyl, pyrrolyl, pyrazolyl, pyrimidinyl, pyridazinyl, pyrazinyl, oxadiazolyl, oxazolyl, thienyl, thiadiazolyl, thiazolyl, triazolyl, and tetrazolyl.

The term "aromatic", as used herein, refers to an unsaturated cyclic moiety that has an aromatic character, while the term "non-aromatic", as used herein, refers to a cyclic moiety, that may be saturated or unsaturated, e.g. polyunsaturated, but that does not have an aromatic character.

The term "phenyl" refers to a moiety of formula $C_6H_5-$, i.e.;

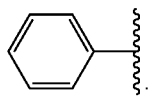

The term "benzyl" refers to a moiety of formula $C_6H_5CH_2-$, i.e.;

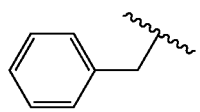

The term "phenylethyl" refers to a moiety of formula $C_6H_5C_2H_4-$, i.e.:

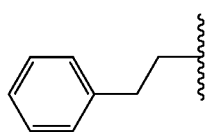

A "methylenedioxy biradical" is a biradical of formula $-OCH_2O-$.

An "ethylenedioxy biradical" is a biradical of formula $-OCH_2CH_2O-$.

"Treatment" as used herein includes prophylaxis of the named disorder or condition, or amelioration or elimination (i.e. cure) of the disorder once it has been established.

An "effective amount" refers to an amount of a compound that confers a therapeutic effect on the treated subject. The therapeutic effect may be objective (i.e., measurable by some test or marker, e.g. no measurable virus titre in a biological sample from the treated subject) or subjective (i.e., subject gives an indication of or feels an effect).

A "non-enveloped single-stranded (+) RNA viral infection" refers to an infection with a non-enveloped single-stranded (+) RNA virus.

A "non-enveloped virus" is a virus lacking viral envelope.

A "single-stranded (+) RNA virus" is a virus having genetic material which is single-stranded RNA and which RNA can be immediately translated to viral protein by the cell infected by the virus.

The term "mammal" refers to a human or any mammalian animal, e.g. a primate, a farm animal, a pet animal, or a laboratory animal. Examples of such animals are monkeys, cows, sheep, goats, horses, pigs, dogs, cats, rabbits, mice, rats etc. Preferably, the mammal is a human. In some embodiments, however, the mammal is an animal, e.g. a farm animal, such as a cow, sheep, goat, horse, or pigs. In some other embodiments, the animal is a pet, e.g. a dog, a cat or a rabbit.

The term "excipient" refers to pharmaceutically acceptable chemicals, such as known to those of ordinary skill in the art of pharmacy to aid the administration of the medicinal agent. It a compound that is useful in preparing a pharmaceutical composition, generally safe, non-toxic and neither biologically nor otherwise undesirable, and includes excipients that are acceptable for veterinary use as well as human pharmaceutical use. Exemplary excipients include binders, surfactants, diluents, disintegrants, antiadherents, and lubricants.

Herein below, any reference to a compound of formula (I) or a compound of the invention, should be construed as referring to a compound for use according to the invention, as defined in the claims.

In a compound of formula (I)

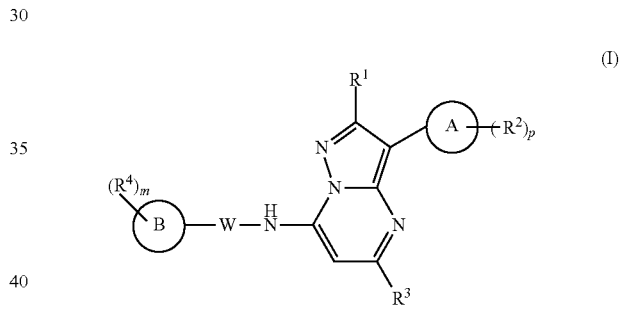

as defined herein above, $R^1$ is selected from H and C1-C6 alkyl, e.g. from H and C1-C4 alkyl, or from H and C1-C3 alkyl, e.g. from H, methyl and ethyl, or from H and methyl, e.g. $R^1$ is H.

In some embodiments, $R^1$ is selected from C1-C6 alkyl, e.g. from C1-C4 alkyl, or from C1-C3 alkyl; e.g. $R^1$ is $CH_3$. In some embodiments, $R^1$ is selected from $CH_3$ and $CH_3CH_2$.

In a compound of formula (I), ring A is phenyl or 5- or 6-membered heteroaryl.

When ring A is 5- or 6-membered heteroaryl, it may contain 1-4 heteroatoms, such as 1, 2 or 3 heteroatoms; or 1 or 2 heteroatoms, in particular 1 heteroatom, independently selected from N, O and S.

In some embodiments, ring A is 5-membered heteroaryl, containing 1-4 heteroatoms, such as 1, 2 or 3 heteroatoms; or 1 or 2 heteroatoms, in particular 1 heteroatom, independently selected from N, O and S.

In some embodiments, ring A is 6-membered heteroaryl, containing 1-4 heteroatoms, such as 1, 2 or 3 heteroatoms; or 1 or 2 heteroatoms, in particular 1 heteroatom, independently selected from N, O and S.

In some embodiments, ring A is phenyl. In some other embodiments, ring A is phenyl or 6-membered heteroaryl, e.g. ring A is 6-membered heteroaryl, such as pyridyl.

In still other embodiments, ring A is 5- or 6-membered heteroaryl, e.g. thienyl or pyridyl. In some embodiments, ring A is 5-membered heteroaryl. In some embodiments, ring A is phenyl or 5-membered heteroaryl, e.g. ring A is phenyl or thienyl.

In those embodiments where ring A is phenyl, the compound of formula (I) may be represented by formula (Ia)

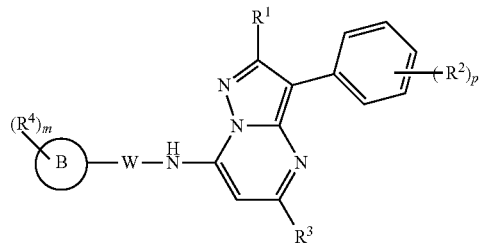

wherein $R^1$, each $R^2$, $R^3$, each $R^4$, W, m and p are as defined herein.

In a compound of formula (I), the variable p, representing the number of substituents $R^2$ on ring A, is an integer of from 0 to 3, e.g. from 0 to 2. In some embodiments, ring A is phenyl and p is 0, 1 or 2. In some embodiments, e.g. when ring A is a 6-membered ring, e.g. ring A is phenyl, p is an integer of from 1 to 3, e.g. p is 1 or 2. In some embodiments, e.g. when ring A is a 6-membered ring, e.g. ring A is phenyl, p is 2 or 3, e.g. p is 2. In some other embodiments, e.g. when ring A is a 5-membered or 6-membered heteroaryl, e.g. A is thienyl or pyridyl, p is 0 or 1, e.g. p is 0.

When ring A is pyridyl, it e.g. may be 4-pyridyl.

In some embodiments, when ring A is 6-membered, e.g. in the embodiments when ring A is phenyl, $R^2$ is not attached to an atom of ring A adjacent to the bond linking ring A to the pyrazolopyrimidine moiety of the compound of formula (I), i.e. $R^2$ is not attached to a carbon atom in ortho position of ring A. Thus, when ring A is phenyl, any $R^2$ is attached in meta or para position on ring A.

In some embodiments, when ring A is phenyl, the moiety

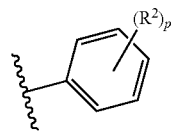

is selected from

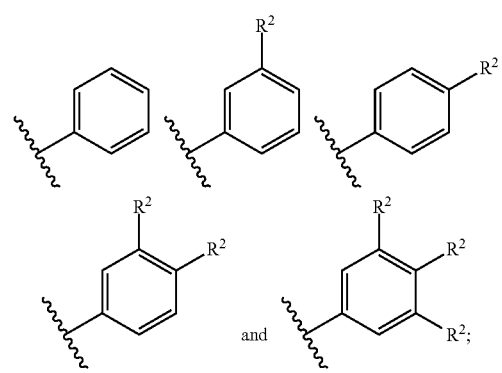

e.g. from

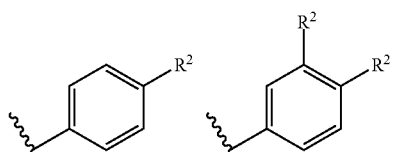

wherein each $R^2$ is as defined herein.

In some embodiments, when ring A is phenyl and p is 0, 1 or 2, the moiety

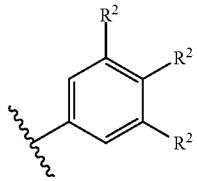

is selected from

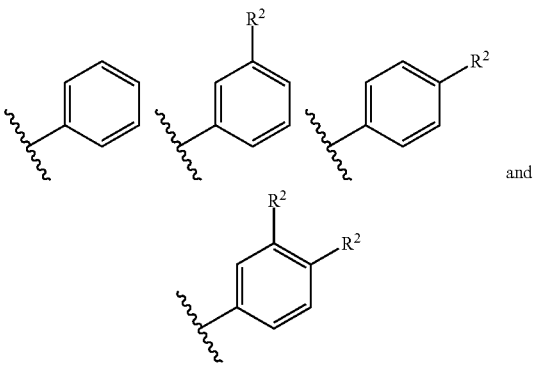

wherein each $R^2$ is as defined herein.

In some embodiments, when ring A is phenyl and p is 1 or 2, the moiety

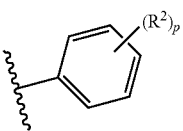

is selected from

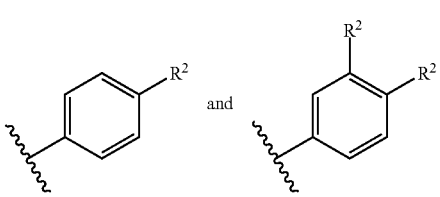

wherein each $R^2$ is as defined herein.

In some particular embodiments, when ring A is phenyl and p is 2, the moiety is

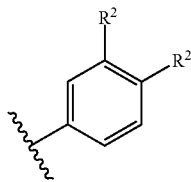

wherein each $R^2$ is as defined herein.

In some embodiments, when ring A is phenyl and the integer p is 2 or 3, the moiety

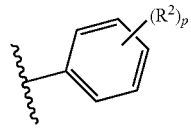

is selected from

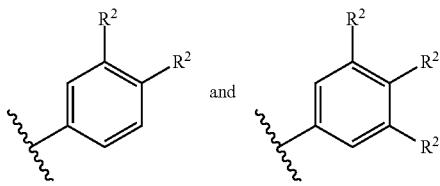

wherein each $R^2$ is as defined herein.

In some embodiments, ring A is selected from phenyl, said phenyl being substituted with 1-3 groups $R^2$, e.g. 1 or 2 groups $R^2$, in particular 2 groups $R^2$; and pyridyl, e.g. 4-pyridyl, said pyridyl being substituted with 0, 1 or 2 groups $R^2$, e.g. 0 or 1 group $R^2$, in particular 0 group $R^2$; and thienyl, said thienyl being substituted with 0 or 1 group $R^2$, e.g. 0 group $R^2$.

In some embodiments, ring A is selected from phenyl, said phenyl being substituted with 1-3 groups $R^2$, e.g. 1 or 2 groups $R^2$, in particular 2 groups $R^2$; and thienyl, said thienyl being substituted with 0 or 1 group $R^2$, e.g. 0 group $R^2$.

In some embodiments, ring A is selected from phenyl, said phenyl being substituted with 1-3 groups $R^2$, e.g. 1 or 2 groups $R^2$, in particular 2 groups $R^2$; and pyridyl, e.g. 4-pyridyl, said pyridyl being substituted with 0, 1 or 2 groups $R^2$, e.g. 0 or 1 group $R^2$, in particular 0 group $R^2$.

In some particular embodiments, the moiety

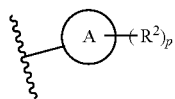

may be represented by the formula

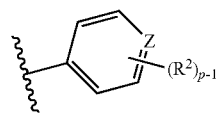

wherein Z is Z is N or $CR^2$, $R_2$ is as defined herein, and p is 1, 2 or 3. In some embodiments, Z is N. In some embodiments, when Z is N, p is 1 (i.e. p–1 is 0). In some other embodiments, Z is $CR^2$. In some embodiments, when Z is $CR^2$, p is 2 or 3, i.e. ring A is mono- or disubstituted.

In a compound of formula (I), each $R^2$ is independently selected from C1-C6 alkyl, $R^5O-$, $R^6R^7NC(O)-$, $R^9C(O)N(R^8)-$, $R^{10}OC(O)-$, $R^{11}C(O)O-$, and halogen; or two $R^2$ attached to adjacent carbon atoms form together a methylenedioxy or ethylenedioxy biradical.

In some embodiments, each $R^2$ is independently selected from C1-C6 alkyl, $R^5O-$, $R^{10}OC(O)-$, and halogen or two $R^2$ attached to adjacent carbon atoms form together a methylenedioxy or ethylenedioxy biradical.

In some embodiments, each $R^2$ is independently selected from C1-C6 alkyl, $R^5O-$, and halogen; or two $R^2$ attached to adjacent carbon atoms together form a methylenedioxy or ethylenedioxy biradical.

In some embodiments, each $R^2$ is independently selected from C1-C6 alkyl, $R^5O-$, and halogen. In some embodiments, each $R^2$ is independently selected from $R^5O-$ and halogen. In some other embodiments, each $R^2$ is independently selected from $R^5O-$ and C1-C6 alkyl. In still other embodiments, each $R^2$ is $R^5O-$.

In some embodiments, each $R^2$ is independently selected from $R^5O-$ and halogen; or two $R^2$ attached to adjacent carbon atoms together form a methylenedioxy or ethylenedioxy biradical.

In some embodiments, each $R^2$ is independently selected from C1-C6 alkyl and $R^5O-$, or two $R^2$ attached to adjacent carbon atoms together form a methylenedioxy or ethylenedioxy biradical.

In some embodiments, each $R^2$ is independently selected from $R^5O-$, or two $R^2$ attached to adjacent carbon atoms together form a methylenedioxy or ethylenedioxy biradical.

When $R^2$ is C1-C6 alkyl, it more particularly may be C1-C4 alkyl, or C1-C3 alkyl, such as methyl and ethyl, in particular methyl.

When $R^2$ is $R^5O-$, $R^6R^7NC(O)-$, $R^9C(O)N(R^8)-$, or $R^{10}OC(O)-$, the moieties $R^5$, $R^6$, $R^7$, $R^8$ and $R^{10}$ are independently selected from H and C1-C6 alkyl, e.g. from H and C1-C4 alkyl, e.g. H and C1-C3 alkyl, such as H, methyl and ethyl, in particular H and methyl. In some embodiments, $R^5$, $R^6$, $R^7$, $R^8$ and $R^{10}$ are independently selected from C1-C6 alkyl, e.g. from C1-C4 alkyl, or C1-C3 alkyl, such as methyl and ethyl, in particular methyl.

When $R^2$ is $R^9C(O)N(R^8)-$ or $R^{11}C(O)O-$, $R^9$ and $R^{11}$ are independently selected from C1-6 alkyl; e.g. C1-C4 alkyl, or C1-C3 alkyl, such as methyl and ethyl, in particular methyl.

When $R^2$ is halogen, said halogen e.g. may be selected from F and Cl.

In some embodiments, ring A is phenyl, p is 2, and each $R^2$ is independently selected from halogen and $R^5O-$, or the two $R^2$ are attached to adjacent carbon atoms and form together a methylenedioxy or ethylenedioxy biradical, e.g. ring A is phenyl, p is 2, and each $R^2$ is $R^5O-$, or the two $R^2$ are attached to adjacent carbon atoms and form together a methylenedioxy or ethylenedioxy biradical.

In some embodiments, when two $R^2$ are attached to adjacent carbon atoms and form together a methylenedioxy or ethylenedioxy biradical, said two $R^2$ more particularly form a methylenedioxy biradical.

In some embodiments, when p is 2, the moiety

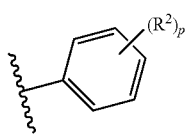

is a moiety of formula

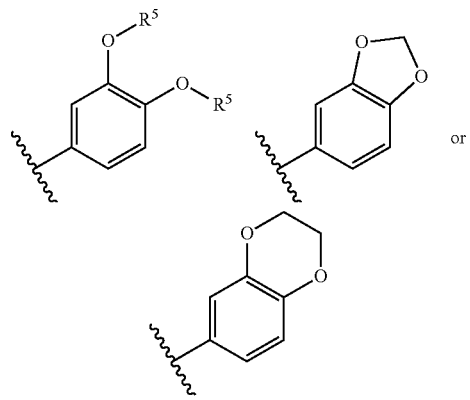

wherein each $R^5$ is as defined herein, e.g. each $R^5$ is C1-C6 alkyl, or each $R^5$ is C1-C3 alkyl, e.g. each $R^5$ is methyl.

In some embodiments, when p is 2, the moiety

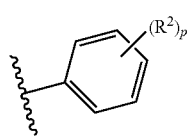

is a moiety of formula

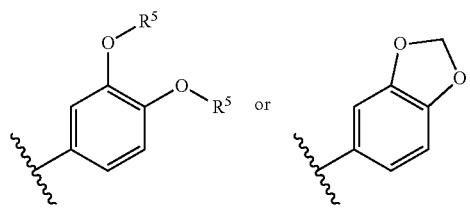

wherein each $R^5$ is as defined herein, e.g. each $R^5$ is methyl.

In some embodiments, when p is 2, the moiety

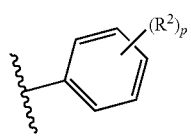

is a moiety of formula

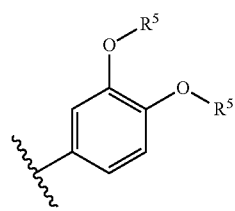

wherein each $R^5$ is as defined herein, e.g. each $R^5$ is methyl.

In a compound of formula (I), $R^3$ is C1-C6 alkyl, e.g. $R^3$ is selected from C1-C5 alkyl, or $R^3$ is selected from C1-C4 alkyl. In some embodiments, $R^3$ is selected from C1-C3 alkyl. In some embodiments, $R^3$ is $CH_3$.

The moiety W is

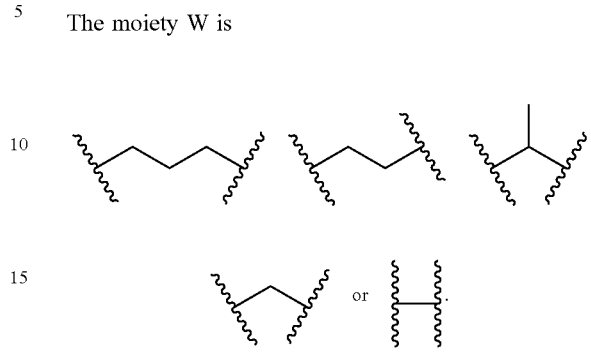

In some embodiments, W is

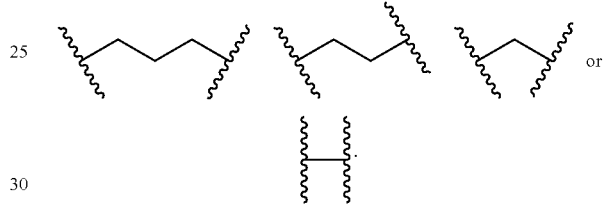

In some embodiments, W is

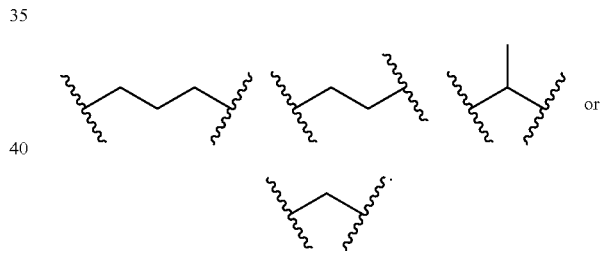

In some other embodiments, W is

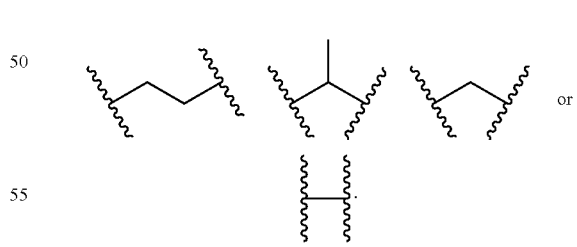

In some embodiments, W is

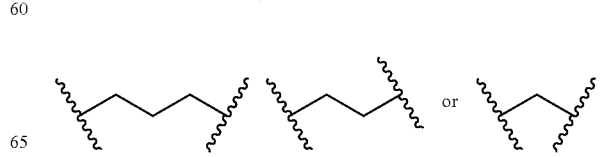

In some other embodiments, W is

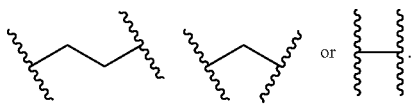

In some embodiments, W is

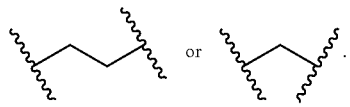

In some other embodiments, W is

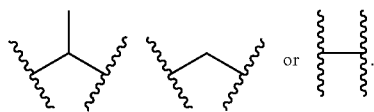

In still other embodiments, W is

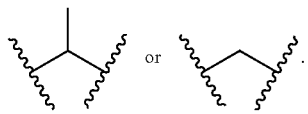

In still other embodiments, W is

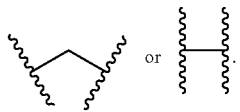

In some particular embodiments, W is

In a compound of formula (I), ring B is 5- or 6-membered saturated or unsaturated carbocyclyl, 5- or 6-membered heteroaryl, or phenyl.

In some embodiments, ring B is 5- or 6-membered saturated or unsaturated carbocyclyl. Any such carbocyclyl is non-aromatic and may be saturated (cycloalkyl) or e.g. mono-unsaturated (cycloalkenyl), e.g. selected from cyclopentyl, cyclohexyl and cyclohexenyl. In some embodiments, when ring B is carbocyclyl, said carbocyclyl is saturated. In some embodiments, when ring B is carbocycylcyl, said carbocyclyl is 5-membered. In some embodiments, when ring B is carbocycylcyl, said carbocyclyl is 6-membered. In some embodiments, ring B is cyclopentyl, cyclohexyl or cyclohexenyl. In some embodiments, ring B is cyclopentyl or cyclohexyl, e.g. ring B is cyclopentyl.

In some embodiments, ring B is 5- or 6-membered saturated or unsaturated carbocyclyl, or phenyl. In some embodiments, ring B is 6-membered saturated or unsaturated carbocyclyl, or phenyl, e.g. ring B is phenyl, cyclohexenyl or cyclohexyl.

In some embodiments, ring B is 5- or 6-membered heteroaryl. When ring B is 5- or 6-membered heteroaryl, it e.g. may contain 1-4 heteroatoms, such as 1, 2 or 3 heteroatoms; or 1 or 2 heteroatoms, or 1 heteroatom, independently selected from N, O and S.

In some embodiments, when ring B is 5- or 6-membered heteroaryl, said heteroaryl is selected from pyridinyl and imidazolyl, e.g. pyridin-2-yl, pyridin-3-yl, pyridin-4-yl and 1H-imidazol-1-yl. In some other embodiments, when ring B is 5- or 6-membered heteroaryl, said heteroaryl is selected from pyridinyl, imidazolyl, pyrimidinyl, thienyl, thiazolyl, isoxazolyl, e.g. pyridin-2-yl, pyridin-3-yl, pyridin-4-yl, 1H-imidazol-1-yl, pyrimidin-4-yl, thien-2-yl, thiazol-2-yl, and isoxazol-3-yl.

In some embodiments, ring B is 5-membered heteroaryl, containing one or more, e.g. 1-4, or 1-3, e.g. 1 or 2 heteroatoms, selected from N, O and S. When ring B is 5-membered heteroaryl, said heteroaryl e.g. may be selected from imidazolyl, thienyl, thiazolyl, isoxazolyl, e.g. 1H-imidazo-1-yl, thien-2-yl, thiazol-2-yl, and isoxazol-3-yl.

In some other particular embodiments, ring B is 6-membered heteroaryl, for example, containing one or more, 1-4, or 1-3, e.g. 1 or 2 heteroatoms, selected from N and O.

When ring B is 6-membered heteroaryl, said heteroaryl e.g. may be selected from pyridinyl, i.e. pyridin-2-yl, pyridin-3-yl, pyridin-4-yl, in particular it may be pyridin-4-yl. In some other embodiments, when ring B is 6-membered heteroaryl, said heteroaryl is selected from pyridinyl and pyrimidinyl e.g. pyridin-2-yl, pyridin-3-yl, pyridin-4-yl, and pyrimidin-4-yl.

In some embodiments, when ring B is heteroaryl, said heteroaryl is not oxadiazolyl. In some embodiments, when ring B is heteroaryl at least one ring heteroatom is nitrogen, e.g. each ring heteroatom is nitrogen.

In some embodiments, when ring B is 5- or 6-membered heteroaryl, said heteroaryl contains 1 heteroatom. In some embodiments, when ring B is 5- or 6-membered heteroaryl, said heteroaryl contains 2 heteroatoms.

In some embodiments, ring B is 5- or 6-membered heteroaryl containing 1 heteroatom. In some other embodiments, ring B is 5- or 6-membered heteroaryl containing 2 heteroatoms.

In some embodiments, ring B is 5- or 6-membered heteroaryl or phenyl, e.g. ring B is 6-membered heteroaryl or phenyl. In some other embodiments, ring B is 5-membered heteroaryl or phenyl.

In some embodiments, ring B is selected from

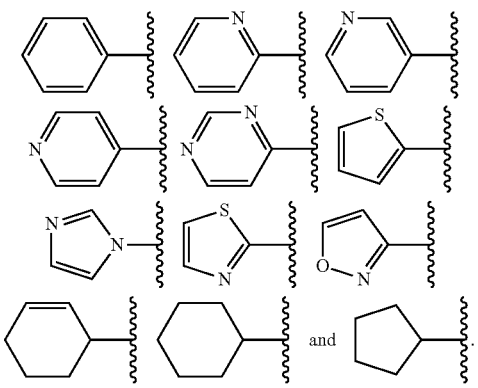

In some embodiments, ring B is phenyl.

When ring B is phenyl, the compound of the invention may be represented by formula (Ib)

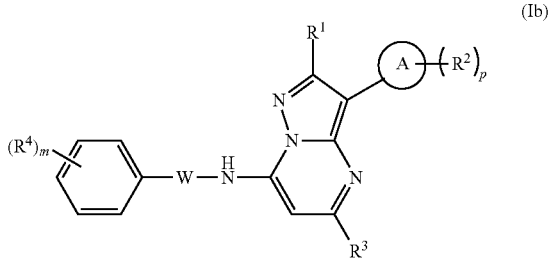

(Ib)

wherein ring A, $R^1$, each $R^2$, $R^3$, each $R^4$, W, m and p are as defined herein.

The integer m represents the number of moieties $R^4$ attached to ring B and is 0, 1, or 2. In some embodiments, m is 0 or 1, e.g. m is 0. In other embodiments, m is 1 or 2. In some embodiments, m is 1. In some embodiments, m is 2.

For example, in some embodiments, ring B is phenyl or 5- or 6-membered heteroaryl, and ring B is optionally substituted with 1-2 moieties $R^4$.

In some embodiments, ring B is 5- or 6-membered heteroaryl, said heteroaryl optionally being substituted with 1 or 2 moieties $R^4$.

In some embodiments, ring B is phenyl, m is 1 or 2, e.g. m is 1, and one $R^4$ is in para position on the phenyl ring.

When m is 1 or 2, each $R^4$ is independently selected from C1-C6 alkyl, $R^{12}O$, halogen, $R^{13}R^{14}NC(O)$—, $R^{16}C(O)N(R^5)$—, $R^{17}OC(O)$—, $R^{18}C(O)O$—, $R^{19}S(O)_2$—, $R^{20}S(O)_2N(H)$—, $NH_2S(O)_2$—, $R^{21}C(O)$—, $N(R^{22})(R^{23})$—, and $^-O$—.

In some embodiments, each $R^4$ is independently selected from C1-C6 alkyl, $R^{12}O$, halogen, $R^{13}R^{14}NC(O)$—, $R^{16}C(O)N(R^{15})$—, $R^{17}OC(O)$— and $R^{18}C(O)O$—.

In some embodiments, each $R^4$ is independently selected from C1-C6 alkyl, $R^{12}O$, halogen, and $R^{16}C(O)N(R^{15})$—. In some other embodiments, each $R^4$ is independently selected from C1-C6 alkyl, $R^{12}O$, and halogen. In still other embodiments, each $R^4$ is independently selected from halogen and $R^{12}O$, e.g. each $R^4$ is $R^{12}O$.

In some embodiments, two $R^4$ attached to adjacent atoms of the ring B form, together with the atoms to which they are attached, a 5- or 6-membered heterocyclic or carbocyclic ring, or a benzene ring. In some embodiments, two $R^4$ attached to adjacent atoms of the ring B form, together with the atoms to which they are attached, a 5- or 6-membered heterocyclic ring or a benzene ring. In some embodiments, two $R^4$ attached to adjacent atoms of the ring B form, together with the atoms to which they are attached a benzene ring. In some embodiments, two $R^4$ attached to adjacent atoms of the ring B form, together with the atoms to which they are attached, a 5- or 6-membered heterocyclic ring.

When $R^4$ is C1-C6 alkyl, said alkyl e.g. may be selected from C1-C4 alkyl, e.g. C1-C3 alkyl, such as methyl and ethyl, in particular methyl.

When $R^4$ is $R^{12}O$, $R^{12}$ is selected from H and C1-C6 alkyl. In some embodiments, $R^{12}$ is selected from C1-C6 alkyl, e.g. from C1-C4 alkyl, in particular from C1-C3 alkyl, such as methyl and ethyl, in particular methyl.

When $R^4$ is halogen, said halogen e.g. may be selected from F, Cl and Br. In some embodiments, when $R^4$ is halogen, said halogen is Cl or Br, in particular Cl. In some other embodiments, when $R^4$ is halogen, said halogen is F or Cl, in particular said halogen is F.

When $R^4$ is selected from $R^{13}R^{14}NC(O)$—, $R^{16}C(O)N(R^{15})$—, $R^{17}OC(O)$—, $R^{18}C(O)O$—, $R^{19}S(O)_2$—, $R^{20}S(O)_2N(H)$—, $R^{21}C(O)$—, and $N(R^{22})(R^{23})$—, each $R^{13}$, $R^{14}$, $R^{15}$, $R^{22}$ and $R^{23}$ is independently selected from H and C1-C6 alkyl, e.g. from H and C1-C4 alkyl, or from H and C1-C3 alkyl, e.g. from H and methyl; and each $R^{16}$, $R^{17}$, $R^{18}$, $R^{19}$, $R^{20}$, and $R^{21}$ is independently selected from C1-6 alkyl, e.g. from C1-C4 alkyl, in particular from C1-C3 alkyl, such as methyl and ethyl, in particular methyl.

When $R^4$ is an alkyl moiety or comprises an alkyl moiety, any such alkyl moiety may be substituted by one or more F.

When two $R^4$ attached to adjacent atoms of the ring B form, together with the atoms to which they are attached, a 5- or 6-membered heterocyclic or carbocyclic ring, said ring e.g. may be 5-membered. For example, two $R^4$ attached to adjacent atoms of the ring B may together with the atoms to which they are attached, a 1,3-dioxolane ring.

In some embodiments, the moiety

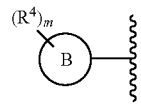

is selected from

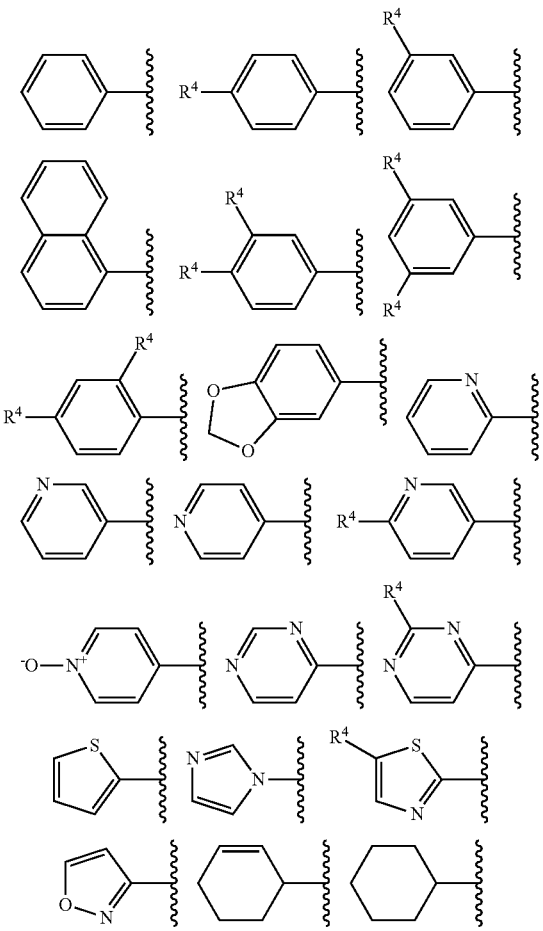

-continued

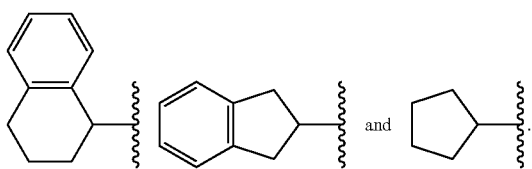

In some embodiments, the moiety

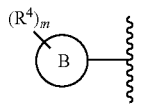

is selected from

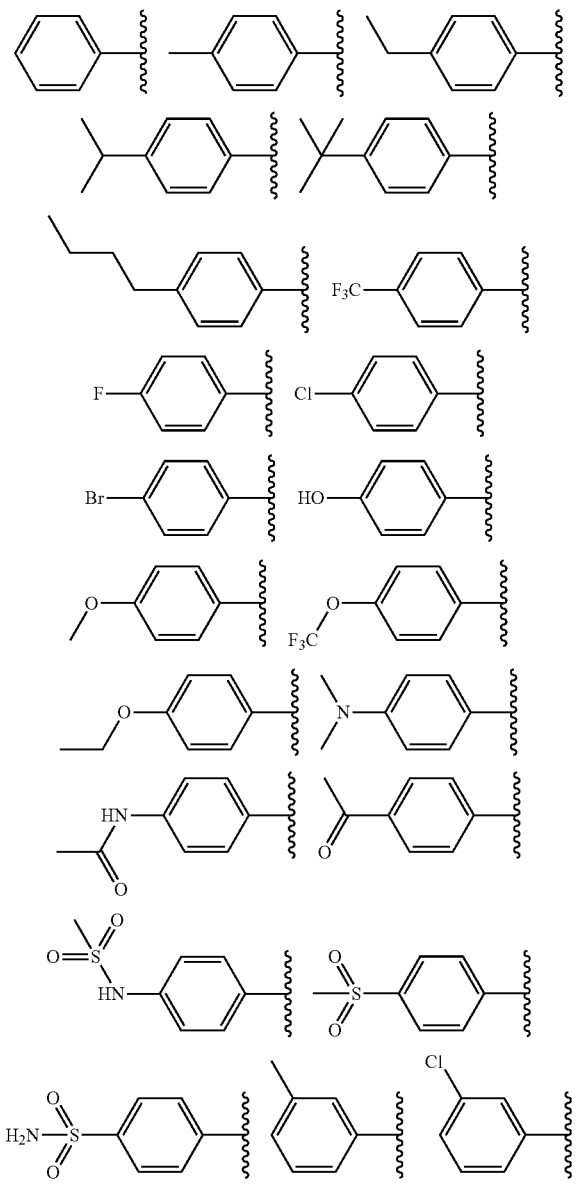

It should be realized that features of the various embodiments described herein may be freely combined within the scope of the present invention, unless mutually incompatible, or unless otherwise specified. For example, in some embodiments of the compound of formula (Ia), ring B is phenyl, as represented in formula (Ib). In these embodiments, the compound may be represented by formula (Ic)

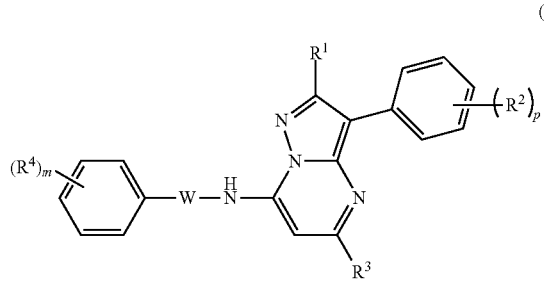

(Ic)

wherein $R^1$, each $R^2$, $R^3$, each $R^4$, W, m and p are as defined herein.

In some embodiments of the compound of formula (Ia), p is 2. In some embodiments of a compound of formula (Ia), when p is 2, the compound is a compound of formula (Id)

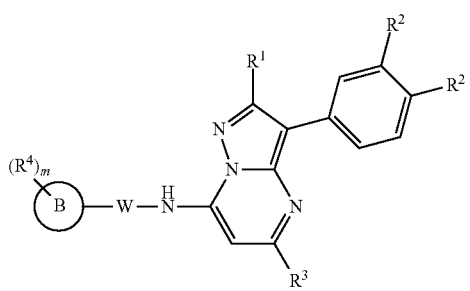

(Id)

wherein $R^1$, each $R^2$, $R^3$, each $R^4$, W, m and ring B are as defined herein.

In some embodiments of a compound of formula (Id), ring B is phenyl or 5- or 6-membered heteroaryl. In some other embodiments of a compound of formula (Id), ring B is phenyl.

In some embodiments of a compound of formula (Ia), e.g. in some embodiments of a compound of formula (Id), each $R^2$ is independently selected from C1-C6 alkyl, $R^5O$— and halogen.

In some particular embodiments of a compound of formula (I), e.g. in a compound of formula (Ia), p is 2 and W is a methylene group. In some embodiments, when p is 2 and W is a methylene group, the compound of formula (Ia) is a compound as represented by formula (Ie)

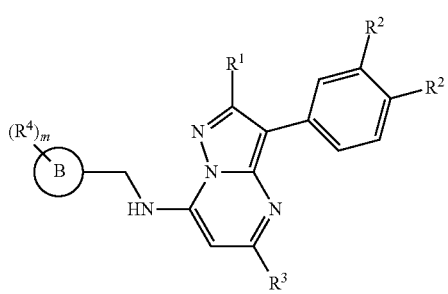

(Ie)

wherein ring B, $R^1$, each $R^2$, $R^3$, each $R^4$, and m are as defined herein.

In some particular embodiments of a compound of formula (Ie), ring B is phenyl, i.e. the compound may represented by formula (If)

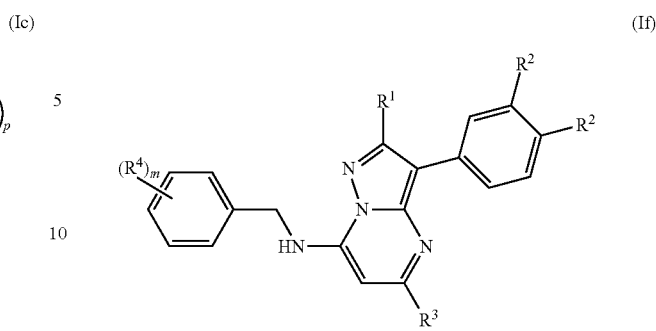

(If)

wherein $R^1$, each $R^2$, $R^3$, each $R^4$, and m are as defined herein.

In some embodiments of a compound of formula (Ib), i.e. in some embodiments of a compound of formula (Ic), in particular in some embodiments of a compound of formula (If), when m is 1 or 2, one moiety $R^4$ is in para position on ring B. In some of these embodiments, m is 1.

In some embodiments of a compound of formula (If), m is 1 and $R^4$ is in para position, i.e. the compound may be represented by formula (Ig)

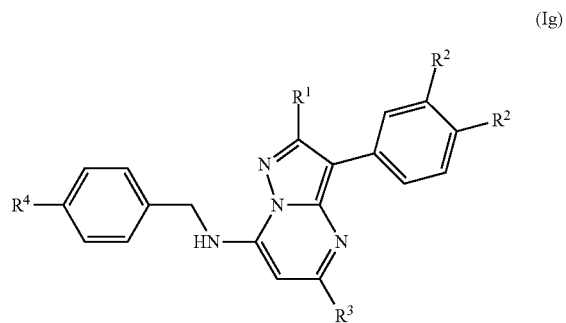

(Ig)

wherein $R^1$, each $R^2$, $R^3$, and $R^4$ are as defined herein.

In some further embodiments a compound of formula (I) may be represented by formula (Ih)

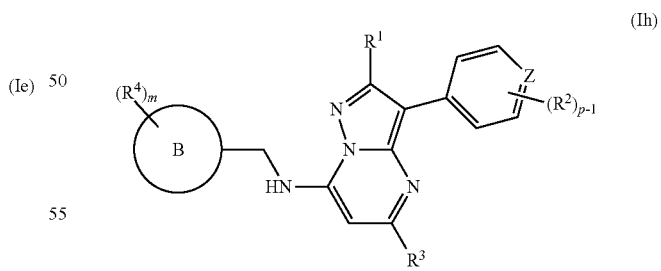

(Ih)

wherein $R^1$, each $R^2$, $R^3$, $R^4$, m, ring B and Z are as defined herein and p is an integer of from 1 to 3.

In formula (Ih), Z is N or $CR^2$. In some embodiments, Z is N. In some embodiments, when Z is N, p is 1 (i.e. p−1 is 0).

In some embodiments of a compound of formula (Ih), Z is $CR^2$, in which case the compound may be represented by formula (Ij)

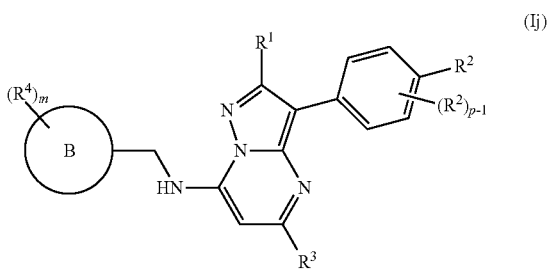

(Ij)

wherein R¹, each R², R³, each R⁴, m and ring B are as defined herein and p is an integer of from 1 to 3, e.g. p is 1 or 2, or p is 2.

In some embodiments of a compound of formula (I), e.g. in some embodiments of formula (Ih), or in some embodiments of formula (Ij), p is 1 or 2. In other embodiments of a compound of formula (I), e.g. in embodiments of formula (Ih), or in embodiments of formula (Ij), p is 1. In some particular embodiments, the compound may be represented by formula (Ik)

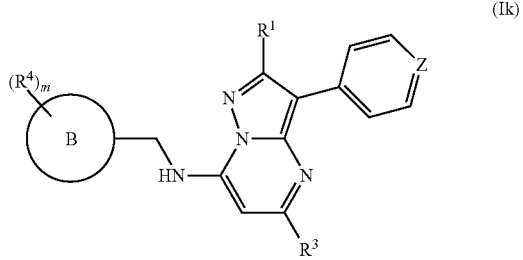

(Ik)

wherein R¹, R³, each R⁴, m, Z and ring B are as defined herein.

In some embodiments of a compound of formula (I), e.g. in embodiments of formula (Ia), or formula (Id), or formula (Ie), or formula (Ih), or formula (Ij), or formula (Ik), ring B is 6-membered heteroaryl, said heteroaryl being substituted by a moiety R⁴ in para position or having a heteroatom, such as N, in para position, or ring B is phenyl, said phenyl being substituted by a moiety R⁴ in para position.

In some embodiments of a compound of formula (I), e.g. in embodiments of formula (Ia), or formula (Id), or formula (Ie), or formula (Ih), or formula (Ij), or formula (Ik), ring B is 6-membered heteroaryl, said heteroaryl being substituted by a moiety R⁴ in para position or having a heteroatom, such as N, in para position.

In some embodiments of a compound of formula (I), e.g. in some embodiments of formula (Ih), or of formula (Ij) or of formula (Ik), ring B is phenyl, said phenyl being substituted by R⁴ in para position. In some embodiments, the compound may be represented by formula (Im)

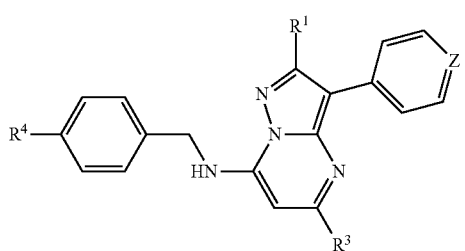

(Im)

wherein R¹, R³, R⁴ and Z are as defined herein.

In some embodiments, in a compound of formula (Im), Z is CR², and the compound may be represented by formula (In)

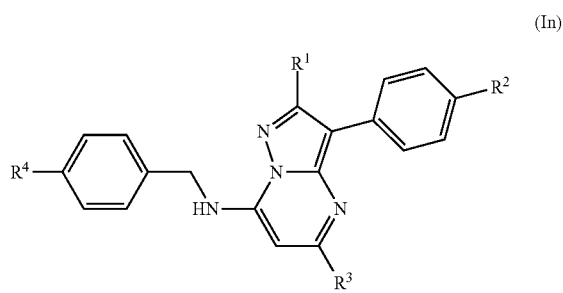

(In)

wherein R¹, R², R³, and R⁴ are as defined herein.

It should be realized that, unless the contrary is apparent from the context or specified, any reference herein to a compound of formula (I) also should be construed as a reference to a compound of any of the embodiments thereof, e.g. a compound according to any one of the formulas (Ia), (Ib), (Ic), (Id), (Ie), (If), (Ig), (Ih), (Ij), (Ik), (Im) and (In).

As noted herein above, some of the compounds of formula (I) are novel. Thus, with the exceptions listed herein, novel compounds are provided according to formula (Id) or according to formula (Ih).

In some embodiments, the novel compound is as represented by formula (Ie), provided that the compound is not
N-[(4-chlorophenyl)methyl]-3-(3,4-dimethoxyphenyl)-2,5-dimethyl-pyrazolo[1,5-a]pyrimidin-7-amine,
3-(3,4-dimethoxyphenyl)-N-[(4-methoxyphenyl)methyl]-2,5-dimethyl-pyrazolo[1,5-a]pyrimidin-7-amine,
3-(3,4-dimethoxyphenyl)-2,5-dimethyl-N-(p-tolylmethyl) pyrazolo[1,5-a]pyrimidin-7-amine,
N-(1,3-benzodioxol-5-ylmethyl)-3-(3,4-dimethoxyphenyl)-2,5-dimethyl-pyrazolo[1,5-a]pyrimidin-7-amine,
3-(3,4-dimethoxyphenyl)-N-[(4-fluorophenyl)methyl]-2,5-dimethyl-pyrazolo[1,5-a]pyrimidin-7-amine,
3-(3,4-dimethoxyphenyl)-2,5-dimethyl-N-(2-pyridylmethyl)pyrazolo[1,5-a]pyrimidin-7-amine, or
N-benzyl-3-(3,4-dimethoxyphenyl)-2,5-dimethyl-pyrazolo[1,5-a]pyrimidin-7-amine.

In some embodiments, the novel compound is as represented by formula (If), provided that the compound is not
N-[(4-chlorophenyl)methyl]-3-(3,4-dimethoxyphenyl)-2,5-dimethyl-pyrazolo[1,5-a]pyrimidin-7-amine,
3-(3,4-dimethoxyphenyl)-N-[(4-methoxyphenyl)methyl]-2,5-dimethyl-pyrazolo[1,5-a]pyrimidin-7-amine,
3-(3,4-dimethoxyphenyl)-2,5-dimethyl-N-(p-tolylmethyl) pyrazolo[1,5-a]pyrimidin-7-amine,
N-(1,3-benzodioxol-5-ylmethyl)-3-(3,4-dimethoxyphenyl)-2,5-dimethyl-pyrazolo[1,5-a]pyrimidin-7-amine,
3-(3,4-dimethoxyphenyl)-N-[(4-fluorophenyl)methyl]-2,5-dimethyl-pyrazolo[1,5-a]pyrimidin-7-amine, or
N-benzyl-3-(3,4-dimethoxyphenyl)-2,5-dimethyl-pyrazolo[1,5-a]pyrimidin-7-amine.

In some embodiments, the novel compound is as represented by formula (Ig), provided that the compound is not
N-[(4-chlorophenyl)methyl]-3-(3,4-dimethoxyphenyl)-2,5-dimethyl-pyrazolo[1,5-a]pyrimidin-7-amine,
3-(3,4-dimethoxyphenyl)-N-[(4-methoxyphenyl)methyl]-2,5-dimethyl-pyrazolo[1,5-a]pyrimidin-7-amine,
3-(3,4-dimethoxyphenyl)-2,5-dimethyl-N-(p-tolylmethyl) pyrazolo[1,5-a]pyrimidin-7-amine, or
3-(3,4-dimethoxyphenyl)-N-[(4-fluorophenyl)methyl]-2,5-dimethyl-pyrazolo[1,5-a]pyrimidin-7-amine.

In some embodiments, the novel compound is as represented by formula (Ik), provided that the compound is not N-benzyl-3-(4-fluorophenyl)-2,5-dimethyl-pyrazolo[1,5-a]pyrimidin-7-amine,
N-benzyl-3-(4-fluorophenyl)-5-methyl-pyrazolo[1,5-a]pyrimidin-7-amine,
N-benzyl-3-(4-chlorophenyl)-5-methyl-pyrazolo[1,5-a]pyrimidin-7-amine,
2,5-dimethyl-3-(p-tolyl)-N-(2-pyridylmethyl)pyrazolo[1,5-a]pyrimidin-7-amine,
2,5-dimethyl-3-(p-tolyl)-N-(3-pyridylmethyl)pyrazolo[1,5-a]pyrimidin-7-amine,
3-(4-fluorophenyl)-2,5-dimethyl-N-(3-pyridylmethyl)pyrazolo[1,5-a]pyrimidin-7-amine,
3-(4-fluorophenyl)-2,5-dimethyl-N-(2-pyridylmethyl)pyrazolo[1,5-a]pyrimidin-7-amine,
3-(4-chlorophenyl)-2,5-dimethyl-N-(2-pyridylmethyl)pyrazolo[1,5-a]pyrimidin-7-amine,
3-(4-chlorophenyl)-2,5-dimethyl-N-(3-pyridylmethyl)pyrazolo[1,5-a]pyrimidin-7-amine,
3-(4-methoxyphenyl)-2,5-dimethyl-N-(3-pyridylmethyl)pyrazolo[1,5-a]pyrimidin-7-amine,
3-(4-methoxyphenyl)-2,5-dimethyl-N-(4-pyridylmethyl)pyrazolo[1,5-a]pyrimidin-7-amine,
N-(cyclohexylmethyl)-2,5-dimethyl-3-(p-tolyl)pyrazolo[1,5-a]pyrimidin-7-amine,
N-benzyl-2,5-dimethyl-3-(p-tolyl)pyrazolo[1,5-a]pyrimidin-7-amine,
3-(4-methoxyphenyl)-2,5-dimethyl-N-(pyridin-3-ylmethyl)pyrazolo[1,5-a]pyrimidin-7-amine, or
3-(4-methoxyphenyl)-2,5-dimethyl-N-(pyridin-4-ylmethyl)pyrazolo[1,5-a]pyrimidin-7-amine.

In some embodiments, the novel compound is as represented by formula (Im).

In some embodiments, the novel compound is as represented by formula (In).

Scheme 1 below illustrates suitable ways of synthesizing compounds of formula (I). For example, compounds of formula (I) may be formed from compounds of formula (III) by treatment with POCl₃ under reflux conditions to give compounds of formula (II), followed by reaction of amines using methods well-known to the person skilled in the art. Examples illustrating the synthetic methods are described in Griffith et al (Bioorg. Med. Chem. Lett. 2011, 21, 2641-2645); Hwang et al (Bioorg. Med. Chem. Lett. 2012, 22, 7297-7301); Gilligan et al, (J. Med. Chem. 2009, 52, 3073-3083); Chen et al (Bioorg. Med. Chem. Lett. 2004, 14, 3669-3673); Tellew et al (Bioorg. Med. Chem. Lett. 2010, 20, 7259-7264); and Yu et al (Med. Chem. Lett. 2013, 4, 230-234).

Compounds of formula (I) can also be formed form compounds of formula (IV) via palladium-catalyzed synthetic methods such as Suzuki, Stille or Negishi reactions, depending on the halogen, as for example described in Gudmundsson et al (Bioorg. Med. Chem. Lett. 2009, 19, 5689-5692); Mayo et al (Adv. Synth. Catal. 2003, 345, 620-624); and US2006/0135526. Compounds of formula (I) may also be formed from compounds of formula (V) by N-alkylations as described by Saito et al (Bioorg. Med. Chem. 2011, 19, 5432-5445.).

Scheme 1

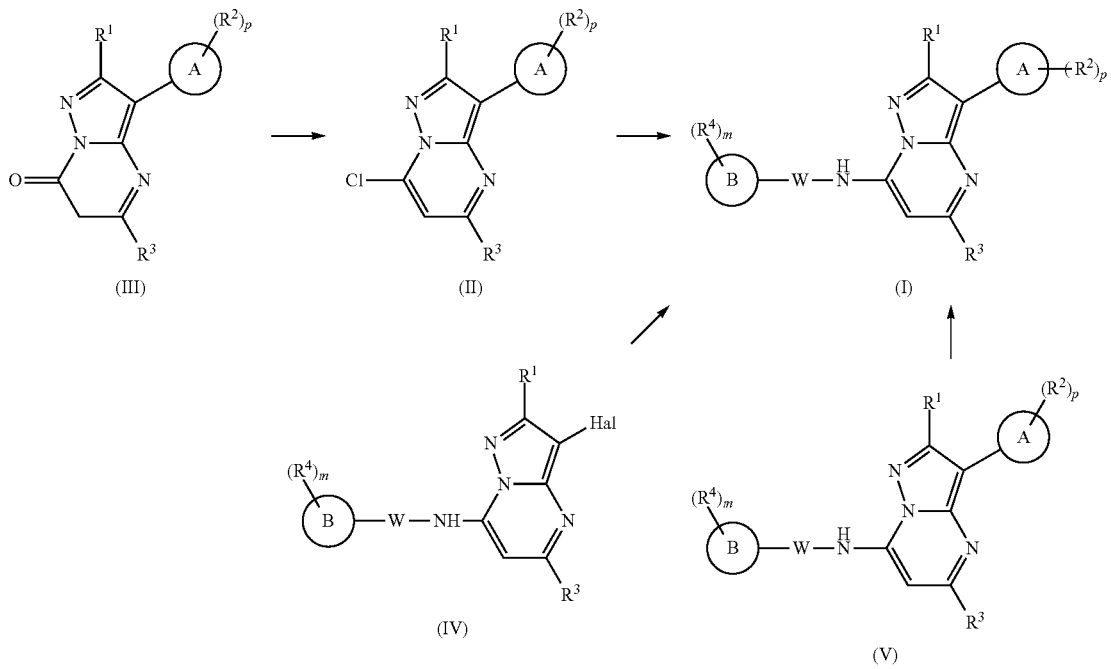

As illustrated below in scheme 2, compounds of formula (IV) can be formed from commercially available starting material (compounds of formula XIII and XIV) followed alkylation of the amine of formula (VI) by a method as described in Majo et al 2003 and references therein. Compounds of formula (IV) can also be formed from compounds of 10 formula (X) by treatment with POCl₃ to give compounds of formula (IX) by a method as described previously, followed by amination, as described in US2006/0135526 or Novinson et al (J. Med. Chem. 1977, 20(2), 296-299), to give compounds of formula (VIII). Compounds of formula (VIII) may then be halogenated using NIS or NBr to give compounds of formula (IV) using methods as described in Labroli et al (Bioorg. Med. Chem. Lett. 2011, 21, 471-474), US20050187224 or US2006135526.

Scheme 2

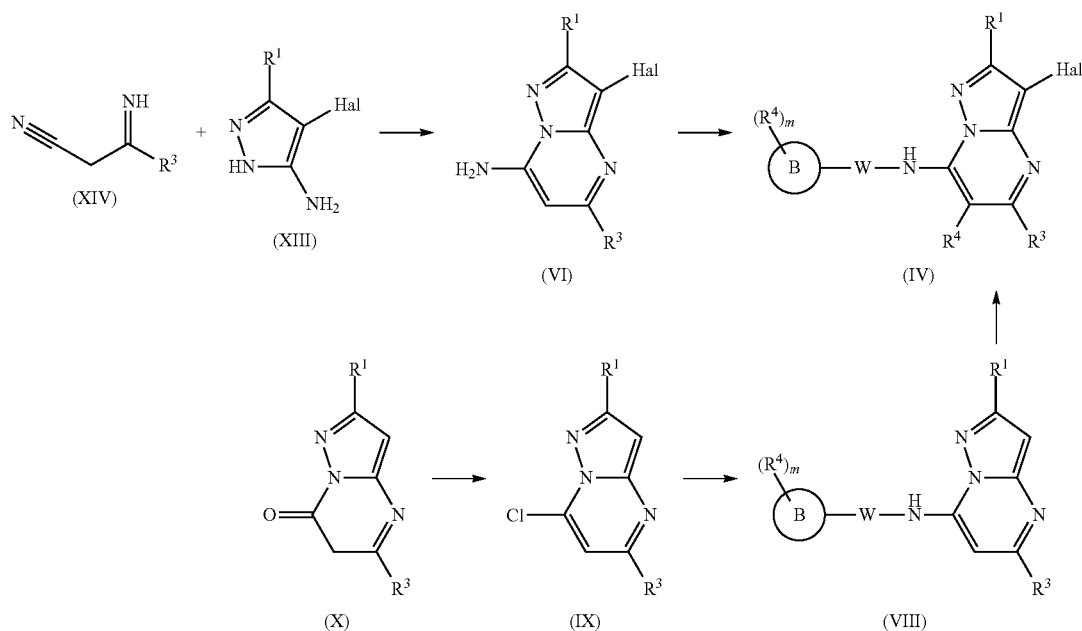

As illustrated below in scheme 3, compounds of formula (IV) can also be formed starting from compounds of formula (X), by treatment with a halogenating agent (e.g. $SOCl_2$, $POCl_3$, $PCl_3$, $PBr_3$ etc) as described previously, to give compounds of formula (IX), which may then be treated with NBS or NIS to give compounds of formula (VII). Methods useful for synthesizing compounds of formula (VII) from compounds of formula (X) are also described in WO2005103052, WO2012033753 and Gudmundsson et al (Bioorg. Med. Chem. Lett. 2009, 19, 5689-5692). Compounds of formula (VII) can then be reacted with amines to give compounds of formula (IV), by methods as described by Gudmundsson et al (Bioorg. Med. Chem. Lett. 2009, 19, 5689-5692) or Bel Abed (Tetrahedron Lett. 2013, 54(21) 2612-2614)

-continued

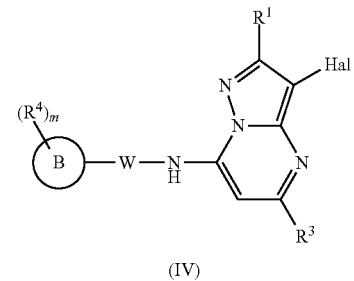

Scheme 3

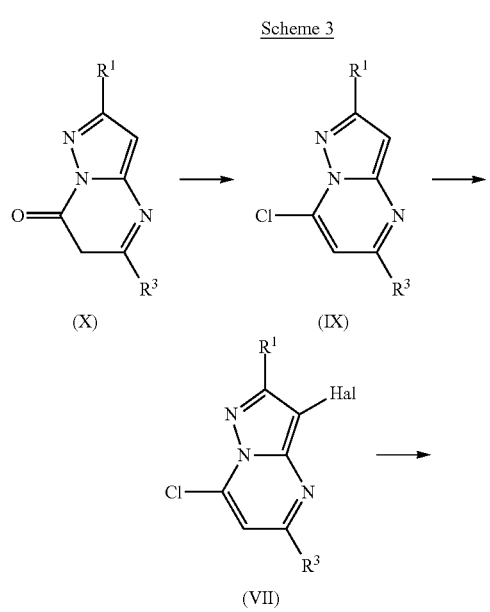

As illustrated below in scheme 4, compounds of formula (III) and formula (X) can be formed from commercially available starting material (compounds of formula XV), by reaction with compounds of formula (XI) or (XII) under conditions described in, for example, Griffith et al (Bioorg. Med. Chem. Lett. 2011, 21, 2641-2645); Hwang et al (Bioorg. Med. Chem. Lett. 2012, 22, 7297-7301); Chen et al (Bioorg. Med. Chem. Lett. 2004, 14, 3669-3673); Yu et al (Med. Chem. Lett. 2013, 4, 230-234) or US2006/0135526.

Scheme 4

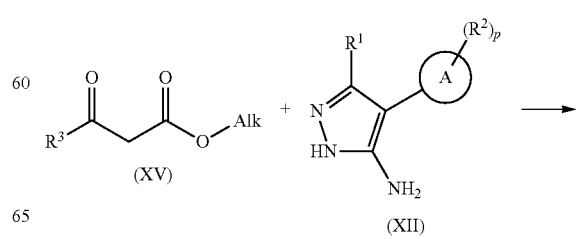

-continued

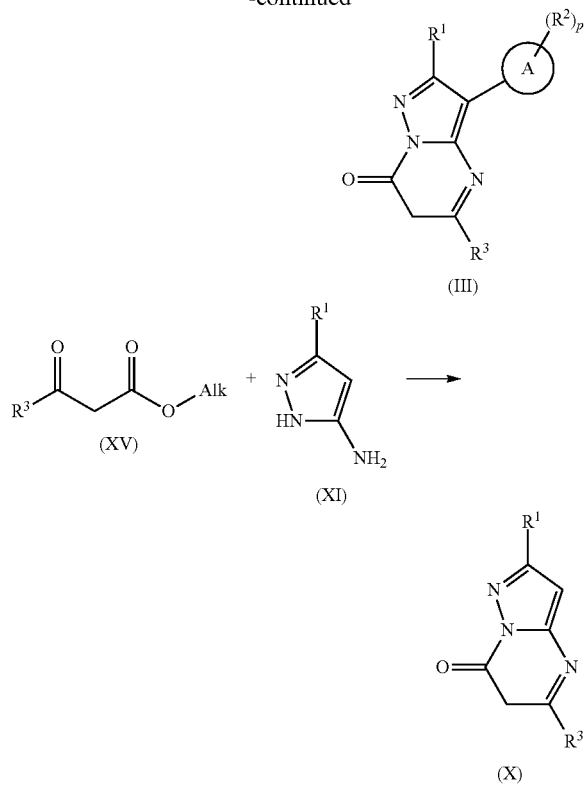

(III)

(XV) + (XI) →

(X)

As illustrated below in scheme 5, compounds of formula (XI), formula (XII) and formula (XIII) can be formed from commercially available starting material (compounds of formula XVI), by reaction with hydrazine under conditions described in several of the above-mentioned publications (Labroli, Chen, Hwang, Griffith, Yu, Bel Abed etc).

Scheme 5

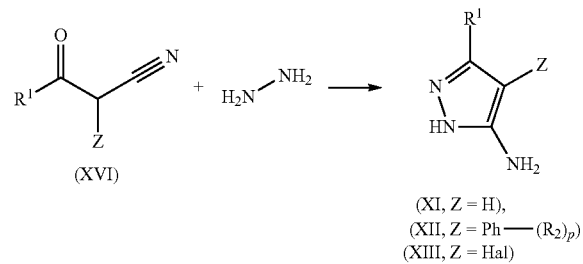

(XVI)

(XI, Z = H),
(XII, Z = Ph—($R_2$)$_p$)
(XIII, Z = Hal)

The term pharmaceutically acceptable salt of a compound refers to a salt that is pharmaceutically acceptable, as defined herein, and that possesses the desired pharmacological activity of the parent compound. Pharmaceutically acceptable salts include acid addition salts formed with inorganic acids, e.g. hydrochloric acid, hydrobromic acid, sulphuric acid, nitric acid, phosphoric acid; or formed with organic acids, e.g. acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, etc.

In the preparation of acid addition salts, preferably such acid are used which form suitably therapeutically acceptable salts. Examples of such acids are hydrohalogen acids, sulfuric acid, phosphoric acid, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid.

Whenever a chiral carbon is present in a chemical structure, it is intended that all stereoisomers associated with that chiral carbon are encompassed by the structure, unless otherwise specified. Using the Cahn-Ingold-Prelog RS notational system, any asymmetric carbon atom may be present in the (R)- or (S)-configuration, and the compound may be present as a mixture of its stereoisomers, e.g. a racemic mixture, or one stereoisomer only.

The present invention includes pharmaceutical compositions comprising at least one compound of formula (I), or an individual isomer, racemic or non-racemic mixture of isomers or a pharmaceutically acceptable salt thereof, together with at least one pharmaceutically acceptable excipient, e.g. a carrier, and optionally other therapeutic and/or prophylactic ingredients.

A pharmaceutical composition according to the invention may be for topical (local) or systemic administration, e.g. for enteral administration, such as rectal or oral administration, or for parenteral administration to a mammal (especially a human), and comprises a therapeutically effective amount of a compound according to the invention or a pharmaceutically acceptable salt thereof, as active ingredient, in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, the disease to be treated and the mode of administration.

For enteral, e.g. oral, administration, the compounds of the invention may be formulated in a wide variety of dosage forms. The pharmaceutical compositions and dosage forms may comprise a compound or compounds of the present invention or pharmaceutically acceptable salt(s) thereof as the active component. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The formulation of the active compound may comprise an encapsulating material as carrier, providing a capsule in which the active component, with or without carriers, is surrounded by a carrier, which is in association with it.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavors, stabilizers, buffers, artificial and natural sweeteners, dispersants, thickeners, solubilising agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compounds of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intracutaneous and subcutaneous injection or infusion.

Thus, for parenteral administration, the pharmaceutical compositions of the invention may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and cholorobutanol.

For inhalation or nasal administration, suitable pharmaceutical formulations are as particles, aerosols, powders, mists or droplets, e.g. with an average size of about 10 µm in diameter or less. For example, compositions for inhalation may be prepared as solutions in saline, employing benzyl alcohol or other suitable preservatives, absorption promoters to enhance bioavailability, fluorocarbons, and/or other solubilising or dispersing agents known in the art.

The pharmaceutical compositions of the invention also may be administered topically, to the skin or to a mucous membrane. For topical application, the pharmaceutical composition may be e.g. a lotion, a gel, a paste, a tincture, a transdermal patch, a gel for transmucosal delivery.

The composition may be formulated as a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water.

Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water.

The pharmaceutical compositions of this invention may also be topically applied to the lower intestinal tract by rectal suppository formulation or in a suitable enema formulation.

Suitable pharmaceutical excipients, e.g. carriers, and methods of preparing pharmaceutical dosage forms are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient.

In general, the compounds of the invention will be administered in a therapeutically effective amount by any of the accepted modes of administration for agents that serve similar utilities. Suitable daily dosages typically ranges from 1 to 1000 mg, e.g. 1-500 mg daily, or 1-50 mg daily, depending upon numerous factors such as the severity of the disease to be treated, the age and relative health of the patient, the potency of the compound used, the route and form of administration, and the indication towards which the administration is directed, etc. One of ordinary skill in the art of treating such diseases will be able, without undue experimentation and in reliance upon personal knowledge and the disclosure of this application, to ascertain a therapeutically effective amount of the compounds of the present invention for a given disease. Compounds of the invention may be administered as pharmaceutical formulations including those suitable for enteral or parenteral administration. The preferred manner of administration is generally oral using a convenient daily dosage regimen which can be adjusted according to the degree of affliction.

The compound of the present invention is contemplated as useful for the treatment of diseases caused by RNA viral infection in a mammal, e.g. non-enveloped single-stranded (+) RNA viral infection, in particular diseases caused by picornaviruses, which is either a human or animal, but preferably a human. The picornavirus e.g. may be a Parechovirus (e.g. Ljungan or Parecho), a Cardiovirus (e.g. EMCV or Theiler's virus), Enterovirus (e.g. EV, Coxsackie, Polio, Rhino) or a hepatovirus. For veterinary use, the picornavirus may be e.g. an Aphthovirus or a Teschovirus.

Diseases that are considered to be linked to, caused by, or otherwise associated with virus infection, e.g. by picornaviruses, are e.g. neurodegenerative diseases such as multiple sclerosis, Parkinson's disease, amyotrophic lateral sclerosis, Alzheimer's disease, Huntington's disease, poliomyelitis, encephalitis, meningitis, sepsis, cancer, paralysis, myocarditis, diabetes, common cold, hand-foot-and-mouth disease, herpangina, pleurodynia, diarrhea, mucocutaneous lesions, respiratory illness, conjunctivitis, myositis, and chronic fatigue syndrome.

The present invention consequently also includes a compound of formula (I) for use in the treatment of any of the above mentioned conditions, as well as the use of a compound of formula (I) in the manufacturing of a medicament for the treatment of any of the above mentioned conditions.

The invention also includes a method of treatment of any of the above mentioned conditions, by administering to an animal or human in need thereof, a compound of formula (I).

The invention is further illustrated by some non-limiting examples.

EXAMPLES

In Table 1, the chemical name of some exemplifying compounds for use of the invention (Ex. 1 to 71) and of some exemplifying novel compounds of the invention (Ex. 72 to 112) are given.

TABLE 1

| Ex | Chemical name |
|----|---------------|
| 1 | N-[(4-chlorophenyl)methyl]-3-(3,4-dimethoxyphenyl)-2,5-dimethyl-pyrazolo[1,5-a]pyrimidin-7-amine |
| 2 | 3-(3,4-dimethoxyphenyl)-N-[(4-methoxyphenyl)methyl]-2,5-dimethyl-pyrazolo[1,5-a]pyrimidin-7-amine |
| 3 | 3-(4-fluorophenyl)-2,5-dimethyl-N-(1-phenylethyl)pyrazolo[1,5-a]pyrimidin-7-amine |
| 4 | N-benzyl-5-isopropyl-3-phenyl-pyrazolo[1,5-a]pyrimidin-7-amine |
| 5 | N-[2-(4-chlorophenyl)ethyl]-3-(3,4-dimethoxyphenyl)-2,5-dimethyl-pyrazolo[1,5-a]pyrimidin-7-amine |
| 6 | 3-(3,4-dimethoxyphenyl)-2,5-dimethyl-N-(p-tolylmethyl)pyrazolo[1,5-a]pyrimidin-7-amine |
| 7 | 3-(3,4-dimethoxyphenyl)-2,5-dimethyl-N-(3-phenylpropyl)pyrazolo[1,5-a]pyrimidin-7-amine |
| 8 | N-(1,3-benzodioxol-5-ylmethyl)-3-(3,4-dimethoxyphenyl)-2,5-dimethyl-pyrazolo[1,5-a]pyrimidin-7-amine |
| 9 | 3-(3,4-dimethoxyphenyl)-N-[(4-fluorophenyl)methyl]-2,5-dimethyl-pyrazolo[1,5-a]pyrimidin-7-amine |
| 10 | 3-(3,4-dimethoxyphenyl)-2,5-dimethyl-N-(2-phenylpropyl)pyrazolo[1,5-a]pyrimidin-7-amine |
| 11 | N-(2-cyclohexen-1-ylethyl)-3-(3,4-dimethoxyphenyl)-2,5-dimethyl-pyrazolo[1,5-a]pyrimidin-7-amine |
| 12 | 3-(3,4-dimethoxyphenyl)-N-[2-(2,4-dimethoxyphenyl)ethyl]-2,5-dimethyl-pyrazolo[1,5-a]pyrimidin-7-amine |
| 13 | N-benzyl-3-(4-fluorophenyl)-2,5-dimethyl-pyrazolo[1,5-a]pyrimidin-7-amine |
| 14 | 3-(4-fluorophenyl)-2,5-dimethyl-N-phenethyl-pyrazolo[1,5-a]pyrimidin-7-amine |
| 15 | N-[2-(3,4-dimethoxyphenyl) ethyl]-3-(4-fluorophenyl)-2,5-dimethyl-pyrazolo[1,5-a]pyrimidin-7-amine |
| 16 | N-(2-cyclohexen-1-ylethyl)-3-(4-fluorophenyl)-2,5-dimethyl-pyrazolo[1,5-a]pyrimidin-7-amine |
| 17 | 3-(4-fluorophenyl)-2,5-dimethyl-N-(1-phenylethyl)pyrazolo[1,5-a]pyrimidin-7-amine |
| 18 | N-benzyl-3-(4-fluorophenyl)-5-methyl-pyrazolo[1,5-a]pyrimidin-7-amine |
| 19 | N-[2-(3,4-dimethoxyphenyl)ethyl]-3-(4-fluorophenyl)-5-methyl-pyrazolo[1,5-a]pyrimidin-7-amine |
| 20 | 5-tert-butyl-N-(2-cyclohexen-1-ylethyl)-3-(4-fluorophenyl)-2-methyl-pyrazolo[1,5-a]pyrimidin-7-amine |
| 21 | N-benzyl-5-methyl-3-phenyl-pyrazolo[1,5-a]pyrimidin-7-amine |
| 22 | N-[2-(3,4-dimethoxyphenyl)ethyl]-5-methyl-3-phenyl-pyrazolo[1,5-a]pyrimidin-7-amine |
| 23 | 5-tert-butyl-N-(3-imidazol-1-ylpropyl)-3-phenyl-pyrazolo[1,5-a]pyrimidin-7-amine |
| 24 | N-(3-imidazol-1-ylpropyl)-2-methyl-3-phenyl-5-propyl-pyrazolo[1,5-a]pyrimidin-7-amine |
| 25 | N-benzyl-3-(4-chlorophenyl)-5-methyl-pyrazolo[1,5-a]pyrimidin-7-amine |
| 26 | 3-(4-chlorophenyl)-5-methyl-N-phenethyl-pyrazolo[1,5-a]pyrimidin-7-amine |
| 27 | 3-(4-chlorophenyl)-N-[2-(3,4-dimethoxyphenyl)ethyl]-5-methyl-pyrazolo[1,5-a]pyrimidin-7-amine |
| 28 | 3-(4-chlorophenyl)-N-(3-imidazol-1-ylpropyl)-5-methyl-pyrazolo[1,5-a]pyrimidin-7-amine |
| 29 | N-[2-(3,4-dimethoxy phenyl)ethyl]-5-methyl-3-(p-tolyl)pyrazolo[1,5-a]pyrimidin-7-amine |
| 30 | N-[2-(3,4-dimethoxyphenyl) ethyl]-2-ethyl-5-methyl-3-phenyl-pyrazolo[1,5-a]pyrimidin-7-amine |
| 31 | 2-ethyl-N-(3-imidazol-1-ylpropyl)-5-methyl-3-phenyl-pyrazolo[1,5-a]pyrimidin-7-amine |
| 32 | 3-(4-chlorophenyl)-2,5-dimethyl-N-[2-(p-tolyl)ethyl]pyrazolo[1,5-a]pyrimidin-7-amine |
| 33 | 2,5-dimethyl-3-(p-tolyl)-N-(2-pyridylmethyl)pyrazolo[1,5-a]pyrimidin-7-amine |
| 34 | 2,5-dimethyl-3-(p-tolyl)-N-(3-pyridylmethyl)pyrazolo[1,5-a]pyrimidin-7-amine |
| 35 | 3-(3,4-dimethoxyphenyl)-2,5-dimethyl-N-(2-pyridylmethyl)pyrazolo[1,5-a]pyrimidin-7-amine |

TABLE 1-continued

| Ex | Chemical name |
|---|---|
| 36 | 3-(4-fluorophenyl)-2,5-dimethyl-N-(3-pyridylmethyl)pyrazolo[1,5-a]pyrimidin-7-amine |
| 37 | 3-(4-fluorophenyl)-2,5-dimethyl-N-(2-pyridylmethyl)pyrazolo[1,5-a]pyrimidin-7-amine |
| 38 | N-cyclopentyl-3-(4-fluorophenyl)-2,5-dimethyl-pyrazolo[1,5-a]pyrimidin-7-amine |
| 39 | 2,5-dimethyl-3-phenyl-N-(3-pyridylmethyl)pyrazolo[1,5-a]pyrimidin-7-amine |
| 40 | N-benzyl-3-(3,4-dimethoxyphenyl)-2,5-dimethyl-pyrazolo[1,5-a]pyrimidin-7-amine |
| 41 | N-cyclopentyl-3-(3,4-dimethoxyphenyl)-2,5-dimethyl-pyrazolo[1,5-a]pyrimidin-7-amine |
| 42 | 3-(4-chlorophenyl)-2,5-dimethyl-N-(2-pyridylmethyl)pyrazolo[1,5-a]pyrimidin-7-amine |
| 43 | N-cyclohexyl-3-(3,4-dimethoxyphenyl)-2,5-dimethyl-pyrazolo[1,5-a]pyrimidin-7-amine |
| 44 | 3-(4-chlorophenyl)-N-(3-imidazol-1-ylpropyl)-2,5-dimethyl-pyrazolo[1,5-a]pyrimidin-7-amine |
| 45 | 3-(4-chlorophenyl)-2,5-dimethyl-N-(3-pyridylmethyl)pyrazolo[1,5-a]pyrimidin-7-amine |
| 46 | N-(4-bromophenyl)-3-(3,4-dimethoxyphenyl)-2,5-dimethyl-pyrazolo[1,5-a]pyrimidin-7-amine |
| 47 | N-(4-chlorophenyl)-3-(3,4-dimethoxyphenyl)-2,5-dimethyl-pyrazolo[1,5-a]pyrimidin-7-amine |
| 48 | 3-(3,4-dimethoxyphenyl)-2,5-dimethyl-N-(p-tolyl)pyrazolo[1,5-a]pyrimidin-7-amine |
| 49 | 3-(3,4-dimethoxyphenyl)-N-(4-methoxyphenyl)-2,5-dimethyl-pyrazolo[1,5-a]pyrimidin-7-amine |
| 50 | 3-(3,4-dimethoxyphenyl)-2,5-dimethyl-N-(m-tolyl)pyrazolo[1,5-a]pyrimidin-7-amine |
| 51 | N-(3-chlorophenyl)-3-(3,4-dimethoxyphenyl)-2,5-dimethyl-pyrazolo[1,5-a]pyrimidin-7-amine |
| 52 | 3-(3,4-dimethoxyphenyl)-N-(3,4-dimethylphenyl)-2,5-dimethyl-pyrazolo[1,5-a]pyrimidin-7-amine |
| 53 | 3-(3,4-dimethoxyphenyl)-N-(4-fluorophenyl)-2,5-dimethyl-pyrazolo[1,5-a]pyrimidin-7-amine |
| 54 | 3-(3,4-dimethoxyphenyl)-N-(4-ethoxyphenyl)-2,5-dimethyl-pyrazolo[1,5-a]pyrimidin-7-amine |
| 55 | N-(3-chloro-4-methyl-phenyl)-3-(3,4-dimethoxyphenyl)-2,5-dimethyl-pyrazolo[1,5-a]pyrimidin-7-amine |
| 56 | 3-(3,4-dimethoxyphenyl)-N-(3,5-dimethylphenyl)-2,5-dimethyl-pyrazolo[1,5-a]pyrimidin-7-amine |
| 57 | 3-(3,4-dimethoxyphenyl)-2,5-dimethyl-N-phenyl-pyrazolo[1,5-a]pyrimidin-7-amine |
| 58 | N-[4-[[3-(3,4-dimethoxy phenyl)-2,5-dimethyl-pyrazolo[1,5-a]pyrimidin-7-yl]amino]phenyl]acetamide |
| 59 | N-(3,4-dichlorophenyl)-3-(3,4-dimethoxyphenyl)-2,5-dimethyl-pyrazolo[1,5-a]pyrimidin-7-amine |
| 60 | 3-(3,4-dimethoxyphenyl)-N-(4-isopropylphenyl)-2,5-dimethyl-pyrazolo[1,5-a]pyrimidin-7-amine |
| 61 | 3-(3,4-dimethoxyphenyl)-N-(3-methoxyphenyl)-2,5-dimethyl-pyrazolo[1,5-a]pyrimidin-7-amine |
| 62 | 3-(3,4-dimethoxyphenyl)-N-(4-ethylphenyl)-2,5-dimethyl-pyrazolo[1,5-a]pyrimidin-7-amine |
| 63 | N-(4-butylphenyl)-3-(3,4-dimethoxyphenyl)-2,5-dimethyl-pyrazolo[1,5-a]pyrimidin-7-amine |
| 64 | N-(3,5-dichlorophenyl)-3-(3,4-dimethoxyphenyl)-2,5-dimethyl-pyrazolo[1,5-a]pyrimidin-7-amine |
| 65 | 3-(4-methoxyphenyl)-2,5-dimethyl-N-(3-pyridylmethyl)pyrazolo[1,5-a]pyrimidin-7-amine |
| 66 | 3-(4-methoxyphenyl)-2,5-dimethyl-N-(4-pyridylmethyl)pyrazolo[1,5-a]pyrimidin-7-amine |
| 67 | N-(3-imidazol-1-ylpropyl)-3-(4-methoxyphenyl)-2,5-dimethyl-pyrazolo[1,5-a]pyrimidin-7-amine |
| 68 | 3-(4-methoxyphenyl)-2,5-dimethyl-N-[2-(2-pyridyl)ethyl]pyrazolo[1,5-a]pyrimidin-7-amine |
| 69 | 2,5-dimethyl-N-(3-pyridylmethyl)-3-(2-thienyl)pyrazolo[1,5-a]pyrimidin-7-amine |
| 70 | 2,5-dimethyl-N-(4-pyridylmethyl)-3-(2-thienyl)pyrazolo[1,5-a]pyrimidin-7-amine |
| 71 | N-(3-imidazol-1-ylpropyl)-2,5-dimethyl-3-(2-thienyl)pyrazolo[1,5-a]pyrimidin-7-amine |
| 72 | 3-(3,4-dimethoxyphenyl)-2,5-dimethyl-N-[[4-(trifluoromethyl)phenyl]methyl]pyrazolo[1,5-a]pyrimidin-7-amine |
| 73 | 3-(3,4-dimethoxyphenyl)-2,5-dimethyl-N-[4-(trifluoromethyl)phenyl]pyrazolo[1,5-a]pyrimidin-7-amine |
| 74 | 3-(3,4-dimethoxyphenyl)-2,5-dimethyl-N-(4-pyridyl)pyrazolo[1,5-a]pyrimidin-7-amine |
| 75 | 3-(3,4-dimethoxyphenyl)-2,5-dimethyl-N-(4-pyridylmethyl)pyrazolo[1,5-a]pyrimidin-7-amine |
| 76 | 3-(3,4-dimethoxyphenyl)-2,5-dimethyl-N-[[4-(trifluoromethoxy)phenyl]methyl]pyrazolo[1,5-a]pyrimidin-7-amine |

TABLE 1-continued

| Ex | Chemical name |
|---|---|
| 77 | N-[4-[[[3-(3,4-dimethoxyphenyl)-2,5-dimethyl-pyrazolo[1,5-a]pyrimidin-7-yl]amino]methyl]phenyl]acetamide |
| 78 | 3-(3,4-dimethoxyphenyl)-N-[(4-dimethylaminophenyl)methyl]-2,5-dimethyl-pyrazolo[1,5-a]pyrimidin-7-amine |
| 79 | 3-(3,4-dimethoxyphenyl)-N-[(6-methoxy-3-pyridyl)methyl]-2,5-dimethyl-pyrazolo[1,5-a]pyrimidin-7-amine |
| 80 | N-[4-[[[3-(3,4-dimethoxyphenyl)-2,5-dimethyl-pyrazolo[1,5-a]pyrimidin-7-yl]amino]methyl]phenyl]methanesulfonamide |
| 81 | 4-[[[3-(3,4-dimethoxyphenyl)-2,5-dimethyl-pyrazolo[1,5-a]pyrimidin-7-yl]amino]methyl]phenol |
| 82 | 3-(3,4-dimethoxyphenyl)-2,5-dimethyl-N-[(3-methylsulfonylphenyl)methyl]pyrazolo[1,5-a]pyrimidin-7-amine |
| 83 | 3-(3,4-dimethoxyphenyl)-2,5-dimethyl-N-[(1-oxidopyridin-1-ium-4-yl)methyl]pyrazolo[1,5-a]pyrimidin-7-amine |
| 84 | 3-(3,4-dimethoxyphenyl)-2,5-dimethyl-N-[(4-methylsulfonylphenyl)methyl]pyrazolo[1,5-a]pyrimidin-7-amine |
| 85 | 3-(3,4-dimethoxyphenyl)-2,5-dimethyl-N-[2-(2-pyridyl)ethyl]pyrazolo[1,5-a]pyrimidin-7-amine |
| 86 | N-[(4-tert-butylphenyl)methyl]-3-(3,4-dimethoxyphenyl)-2,5-dimethyl-pyrazolo[1,5-a]pyrimidin-7-amine |
| 87 | 3-(3,4-dimethoxyphenyl)-2,5-dimethyl-N-[(2-methylpyrimidin-4-yl)methyl]pyrazolo[1,5-a]pyrimidin-7-amine |
| 88 | 3-(3,4-dimethoxyphenyl)-2,5-dimethyl-N-[2-(2-thienyl)ethyl]pyrazolo[1,5-a]pyrimidin-7-amine |
| 89 | 3-(3,4-dimethoxyphenyl)-2,5-dimethyl-N-[2-(4-pyridyl)ethyl]pyrazolo[1,5-a]pyrimidin-7-amine |
| 90 | 3-(3,4-dimethoxyphenyl)-2,5-dimethyl-N-pyrazin-2-yl-pyrazolo[1,5-a]pyrimidin-7-amine |
| 91 | 3-(3,4-dimethoxyphenyl)-N-indan-2-yl-2,5-dimethyl-pyrazolo[1,5-a]pyrimidin-7-amine |
| 92 | 3-(3,4-dimethoxyphenyl)-2,5-dimethyl-N-[(6-methyl-3-pyridyl)methyl]pyrazolo[1,5-a]pyrimidin-7-amine |
| 93 | N-[3-(3,4-dimethoxyphenyl)-2,5-dimethyl-pyrazolo[1,5-a]pyrimidin-7-yl]-5-methyl-thiazol-2-amine |
| 94 | 1-[4-[[[3-(3,4-dimethoxyphenyl)-2,5-dimethyl-pyrazolo[1,5-a]pyrimidin-7-yl]amino]methyl]phenyl]ethanone |
| 95 | N-[3-(3,4-dimethoxyphenyl)-2,5-dimethyl-pyrazolo[1,5-a]pyrimidin-7-yl]isoxazol-3-amine |
| 96 | 3-(3,4-dimethoxyphenyl)-2,5-dimethyl-N-(1-naphthylmethyl)pyrazolo[1,5-a]pyrimidin-7-amine |
| 97 | 4-[[[3-(3,4-dimethoxyphenyl)-2,5-dimethyl-pyrazolo[1,5-a]pyrimidin-7-yl]amino]methyl]benzenesulfonamide |
| 98 | 3-(3,4-dimethoxyphenyl)-2,5-dimethyl-N-[1-(4-pyridyl)ethyl]pyrazolo[1,5-a]pyrimidin-7-amine |
| 99 | 3-(3,4-dimethoxyphenyl)-N-[(4-fluorophenyl)methyl]-5-methyl-pyrazolo[1,5-a]pyrimidin-7-amine |
| 100 | 3-(3,4-dimethoxyphenyl)-5-methyl-N-(4-pyridylmethyl)pyrazolo[1,5-a]pyrimidin-7-amine |
| 101 | 3-(3,4-dimethoxyphenyl)-5-methyl-N-[(3-methylsulfonylphenyl)methyl]pyrazolo[1,5-a]pyrimidin-7-amine |
| 102 | 3-(1,3-benzodioxol-5-yl)-N-[(4-fluorophenyl)methyl]-2,5-dimethyl-pyrazolo[1,5-a]pyrimidin-7-amine |
| 103 | 3-(3,4-dichlorophenyl)-N-[(4-fluorophenyl)methyl]-2,5-dimethyl-pyrazolo[1,5-a]pyrimidin-7-amine |
| 104 | N-[(4-fluorophenyl)methyl]-2,5-dimethyl-3-[4-(trifluoromethyl)phenyl]pyrazolo[1,5-a]pyrimidin-7-amine |
| 105 | N-[(4-fluorophenyl)methyl]-2,5-dimethyl-3-(3,4,5-trimethoxyphenyl)pyrazolo[1,5-a]pyrimidin-7-amine |
| 106 | 3-(3,4-difluorophenyl)-N-[(4-fluorophenyl)methyl]-2,5-dimethyl-pyrazolo[1,5-a]pyrimidin-7-amine |
| 107 | methyl 4-[7-[(4-fluorophenyl)methylamino]-2,5-dimethyl-pyrazolo[1,5-a]pyrimidin-3-yl]benzoate |
| 108 | 3-(3-fluoro-4-methoxy-phenyl)-2,5-dimethyl-N-(p-tolylmethyl)pyrazolo[1,5-a]pyrimidin-7-amine |
| 109 | 3-(3,4-diethoxyphenyl)-N-[(4-fluorophenyl)methyl]-2,5-dimethyl-pyrazolo[1,5-a]pyrimidin-7-amine |
| 110 | 4-[2,5-dimethyl-7-(p-tolylmethylamino)pyrazolo[1,5-a]pyrimidin-3-yl]benzene-1,2-diol |
| 111 | 3-(3,4-dimethoxyphenyl)-N-[(4-fluorophenyl)methyl]-5-isopropyl-2-methyl-pyrazolo[1,5-a]pyrimidin-7-amine |
| 112 | N-[(4-fluorophenyl)methyl]-2,5-dimethyl-3-(4-pyridyl)pyrazolo[1,5-a]pyrimidin-7-amine |

In Table 2, the structural formulas of the compounds of Examples 1-112 are given.
TABLE 2
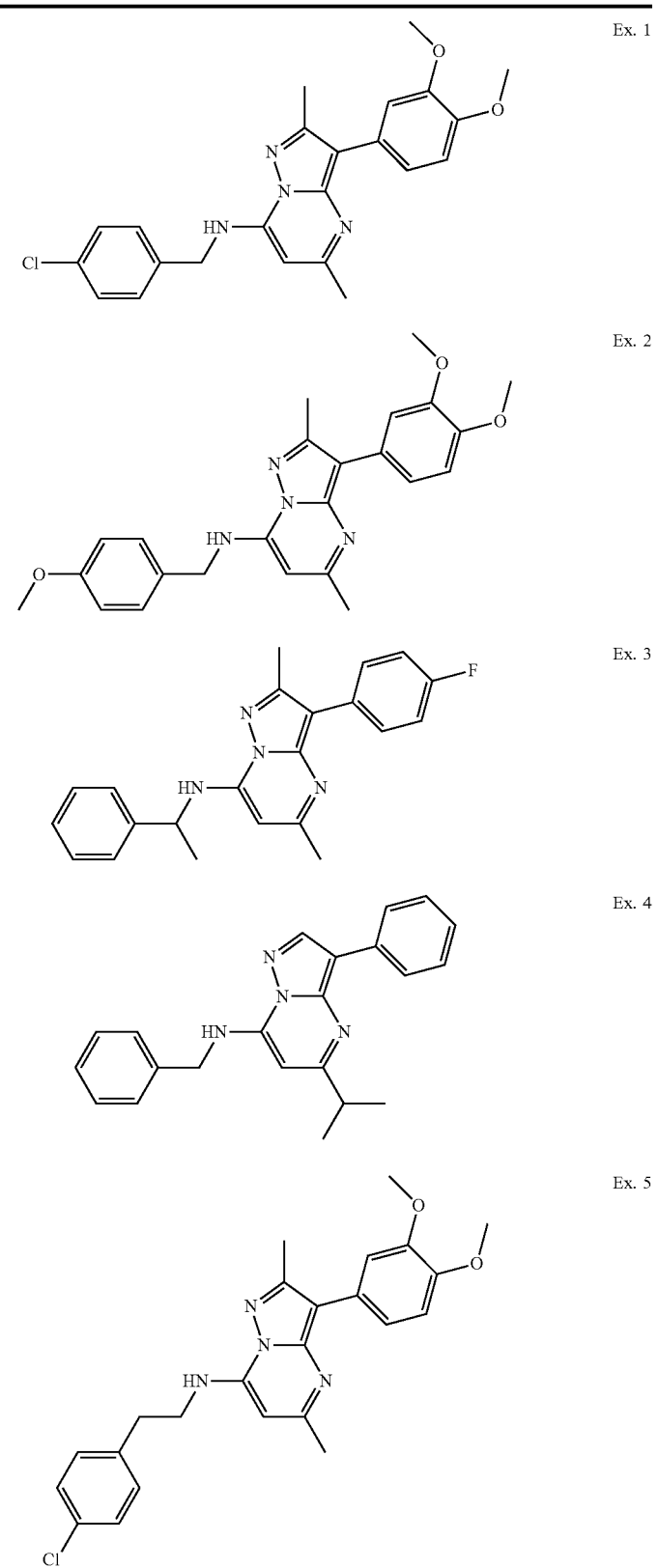
Ex. 1
Ex. 2
Ex. 3
Ex. 4
Ex. 5

TABLE 2-continued
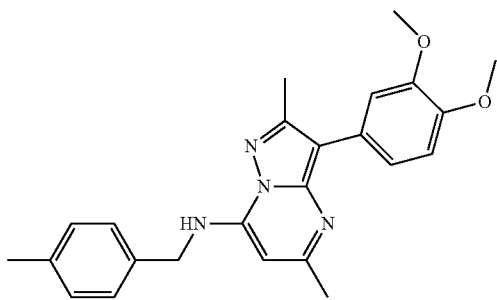
Ex. 6
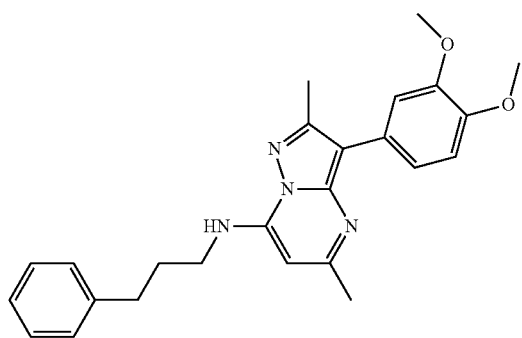 [SMILES: COc1ccc(-c2c(C)nn3c(NCCCc4ccccc4)cc(C)nc23)cc1OC]
Ex. 7
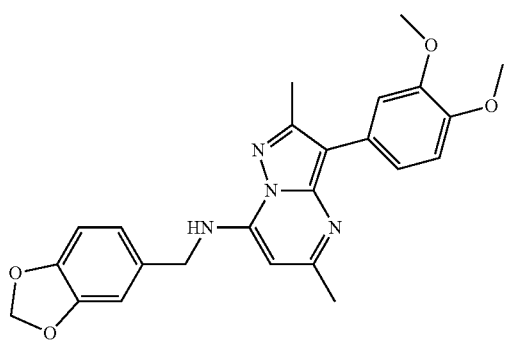 [SMILES: COc1ccc(-c2c(C)nn3c(NCc4ccc5c(c4)OCO5)cc(C)nc23)cc1OC]
Ex. 8
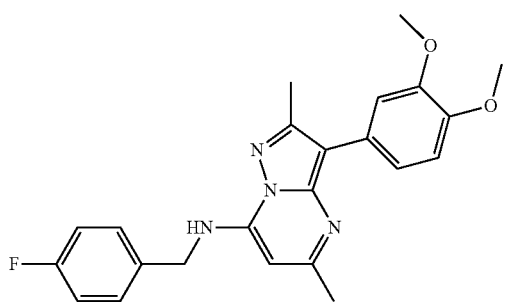 [SMILES: COc1ccc(-c2c(C)nn3c(NCc4ccc(F)cc4)cc(C)nc23)cc1OC]
Ex. 9

TABLE 2-continued
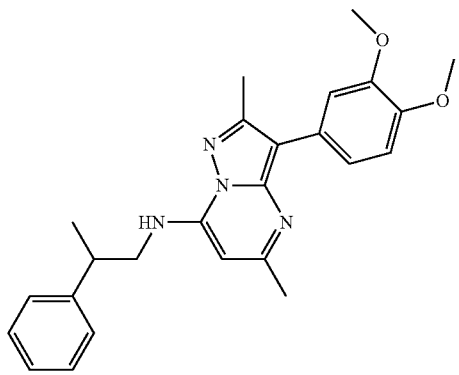 [SMILES: COc1ccc(-c2c(C)nn3c(NCC(C)c4ccccc4)cc(C)nc23)cc1OC]
Ex. 10
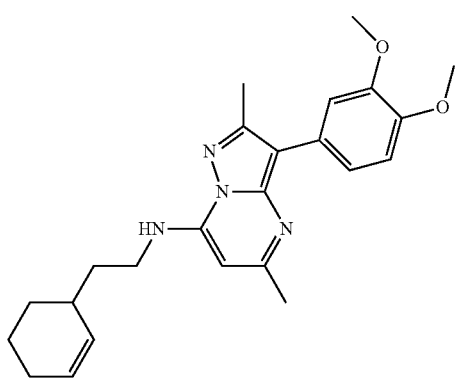 [SMILES: COc1ccc(-c2c(C)nn3c(NCCC4C=CCCC4)cc(C)nc23)cc1OC]
Ex. 11
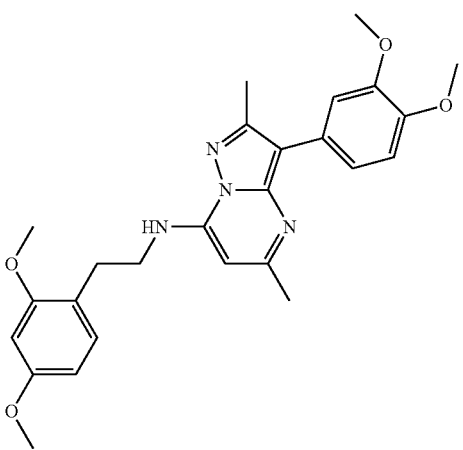 [SMILES: COc1ccc(CCNc2cc(C)nc3c(-c4ccc(OC)c(OC)c4)c(C)nn23)c(OC)c1]
Ex. 12
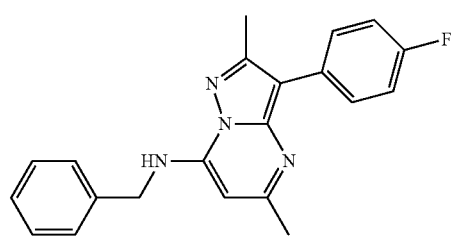 [SMILES: Cc1cc(NCc2ccccc2)n2nc(C)c(-c3ccc(F)cc3)c2n1]
Ex. 13

TABLE 2-continued
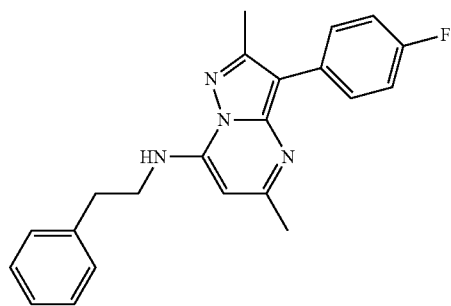 [SMILES: Cc1cc(NCCc2ccccc2)n2nc(C)c(-c3ccc(F)cc3)c2n1]
Ex. 14
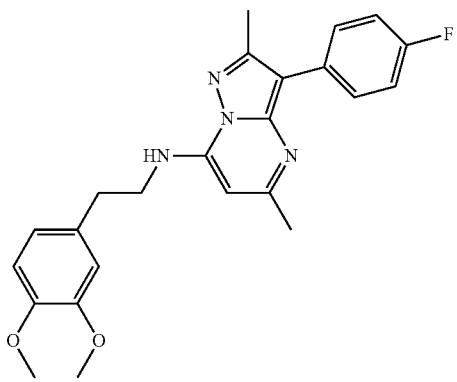 [SMILES: COc1ccc(CCNc2cc(C)nc3c(-c4ccc(F)cc4)c(C)nn23)cc1OC]
Ex. 15
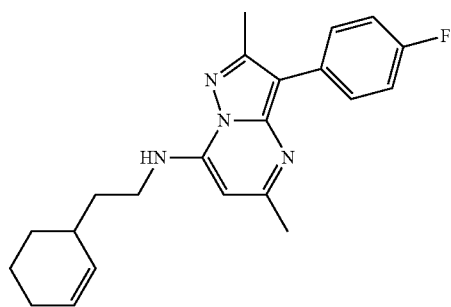 [SMILES: Cc1cc(NCCC2C=CCCC2)n2nc(C)c(-c3ccc(F)cc3)c2n1]
Ex. 16
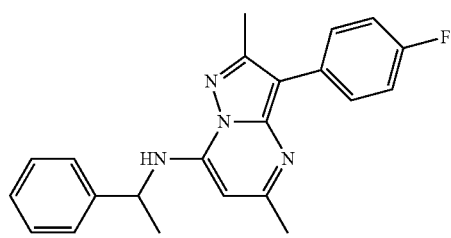 [SMILES: Cc1cc(NC(C)c2ccccc2)n2nc(C)c(-c3ccc(F)cc3)c2n1]
Ex. 17
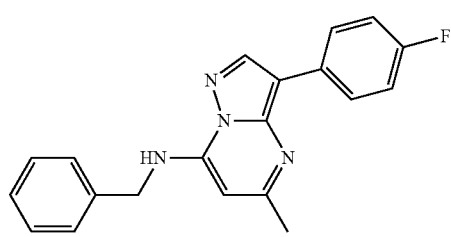 [SMILES: Cc1cc(NCc2ccccc2)n2ncc(-c3ccc(F)cc3)c2n1]
Ex. 18

TABLE 2-continued
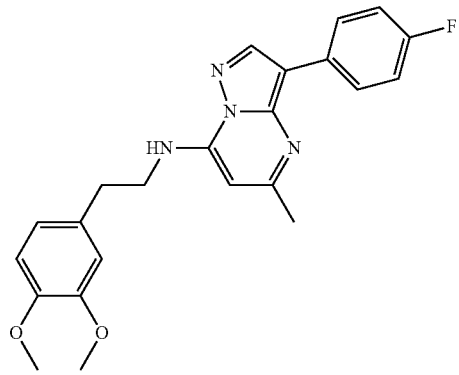 [SMILES: COc1ccc(CCNc2cc(C)nc3c(-c4ccc(F)cc4)cnn23)cc1OC]
Ex. 19
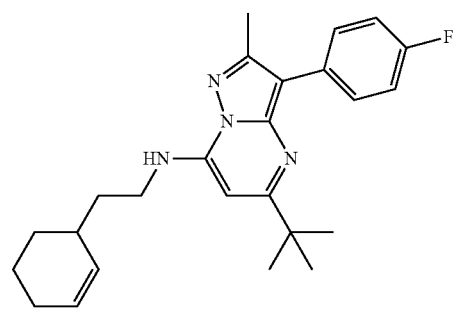 [SMILES: Cc1nn2c(NCCC3C=CCCC3)cc(C(C)(C)C)nc2c1-c1ccc(F)cc1]
Ex. 20
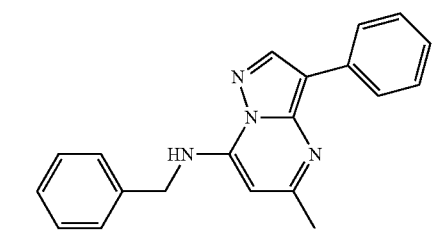 [SMILES: Cc1cc(NCc2ccccc2)n2ncc(-c3ccccc3)c2n1]
Ex. 21
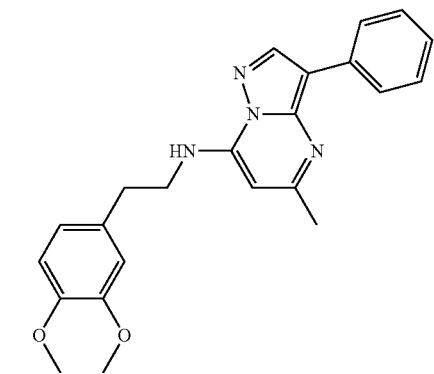 [SMILES: COc1ccc(CCNc2cc(C)nc3c(-c4ccccc4)cnn23)cc1OC]
Ex. 22
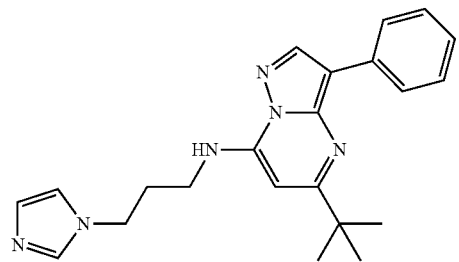 [SMILES: CC(C)(C)c1cc(NCCCn2ccnc2)n2ncc(-c3ccccc3)c2n1]
Ex. 23

TABLE 2-continued
| | |
|---|---|
| 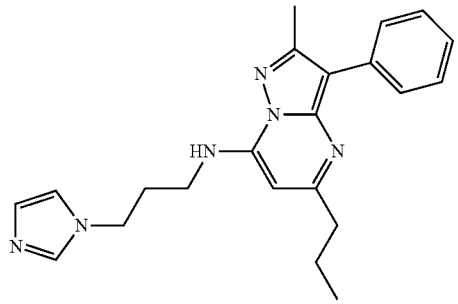 [SMILES: CCCc1cc(NCCCn2ccnc2)n2nc(C)c(-c3ccccc3)c2n1] | Ex. 24 |
| 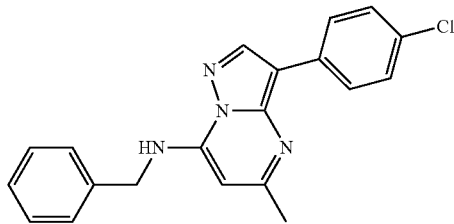 [SMILES: Cc1cc(NCc2ccccc2)n2ncc(-c3ccc(Cl)cc3)c2n1] | Ex. 25 |
| 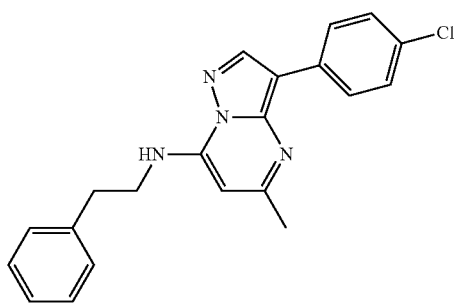 [SMILES: Cc1cc(NCCc2ccccc2)n2ncc(-c3ccc(Cl)cc3)c2n1] | Ex. 26 |
| 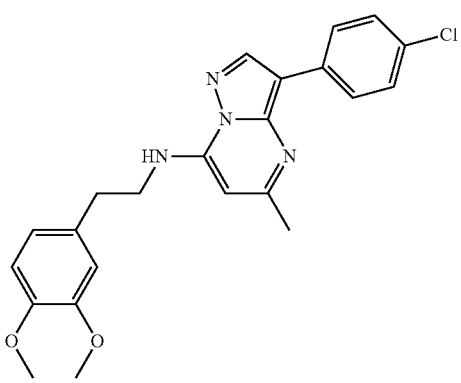 [SMILES: COc1ccc(CCNc2cc(C)nc3c(-c4ccc(Cl)cc4)cnn23)cc1OC] | Ex. 27 |
| 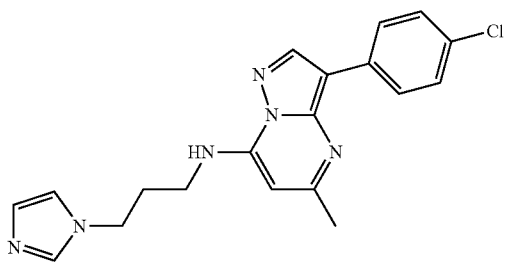 [SMILES: Cc1cc(NCCCn2ccnc2)n2ncc(-c3ccc(Cl)cc3)c2n1] | Ex. 28 |

TABLE 2-continued
| | |
|---|---|
| 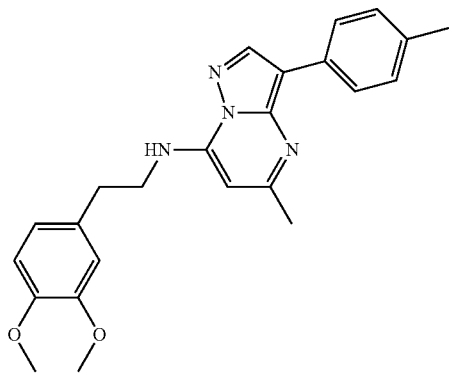 [SMILES: COc1ccc(CCNc2cc(C)nc3c(-c4ccc(C)cc4)cnn23)cc1OC] | Ex. 29 |
| 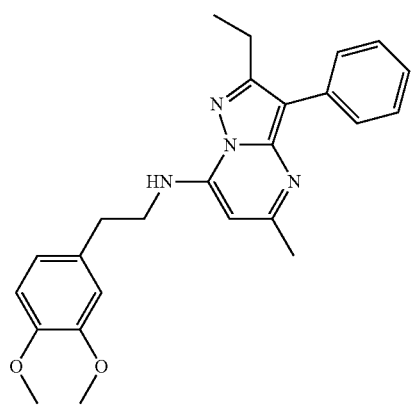 [SMILES: CCc1nn2c(NCCc3ccc(OC)c(OC)c3)cc(C)nc2c1-c1ccccc1] | Ex. 30 |
| 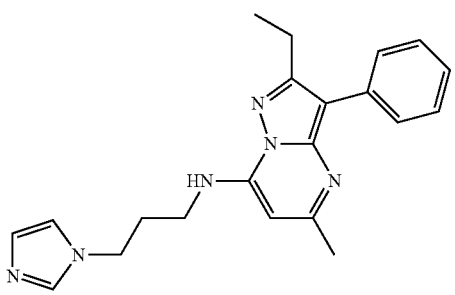 [SMILES: CCc1nn2c(NCCCn3ccnc3)cc(C)nc2c1-c1ccccc1] | Ex. 31 |
| 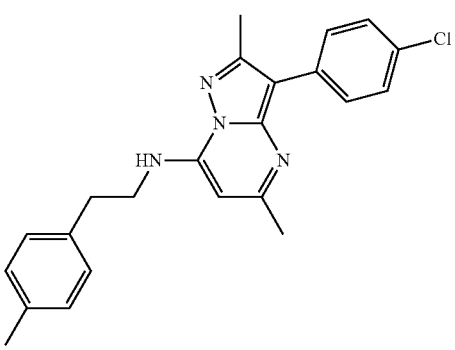 [SMILES: Cc1ccc(CCNc2cc(C)nc3c(-c4ccc(Cl)cc4)c(C)nn23)cc1] | Ex. 32 |
| 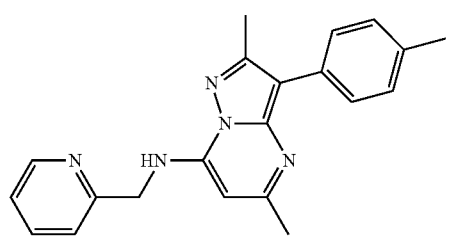 [SMILES: Cc1ccc(-c2c(C)nn3c(NCc4ccccn4)cc(C)nc23)cc1] | Ex. 33 |

TABLE 2-continued
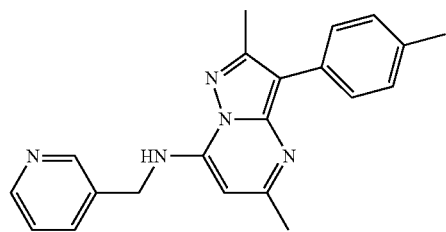 [SMILES: Cc1ccc(-c2c(C)nn3c(NCc4cccnc4)cc(C)nc23)cc1]
Ex. 34
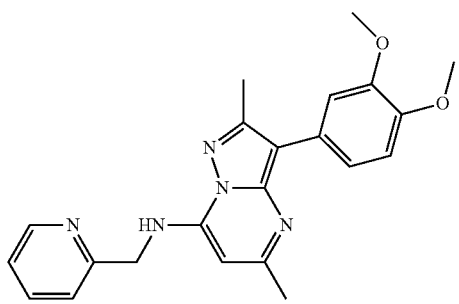 [SMILES: COc1ccc(-c2c(C)nn3c(NCc4ccccn4)cc(C)nc23)cc1OC]
Ex. 35
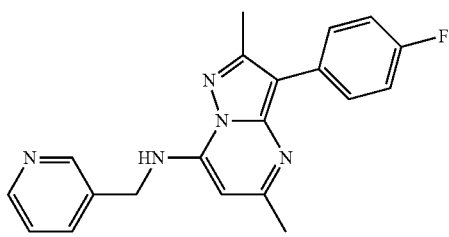 [SMILES: Cc1cc(NCc2cccnc2)n2nc(C)c(-c3ccc(F)cc3)c2n1]
Ex. 36
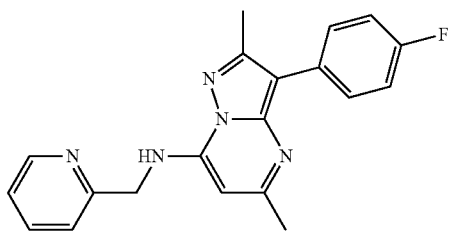 [SMILES: Cc1cc(NCc2ccccn2)n2nc(C)c(-c3ccc(F)cc3)c2n1]
Ex. 37
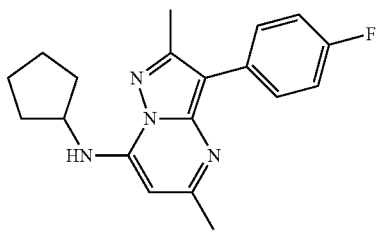 [SMILES: Cc1cc(NC2CCCC2)n2nc(C)c(-c3ccc(F)cc3)c2n1]
Ex. 38
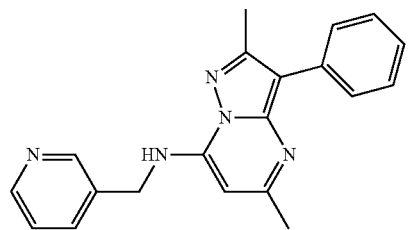 [SMILES: Cc1cc(NCc2cccnc2)n2nc(C)c(-c3ccccc3)c2n1]
Ex. 39

TABLE 2-continued
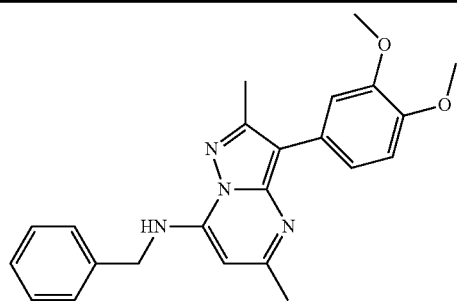
Ex. 40
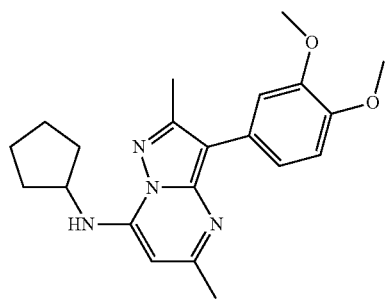 [SMILES: COc1ccc(-c2c(C)nn3c(NC4CCCC4)cc(C)nc23)cc1OC]
Ex. 41
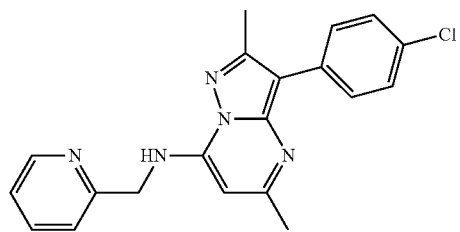 [SMILES: Cc1cc(NCc2ccccn2)n2nc(C)c(-c3ccc(Cl)cc3)c2n1]
Ex. 42
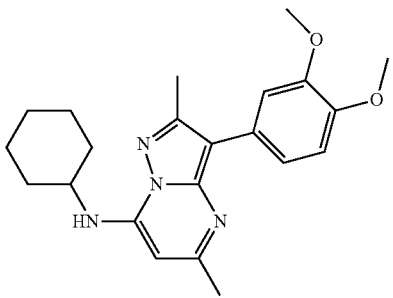 [SMILES: COc1ccc(-c2c(C)nn3c(NC4CCCCC4)cc(C)nc23)cc1OC]
Ex. 43
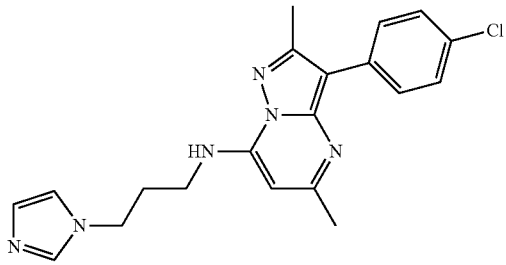 [SMILES: Cc1cc(NCCCn2ccnc2)n2nc(C)c(-c3ccc(Cl)cc3)c2n1]
Ex. 44
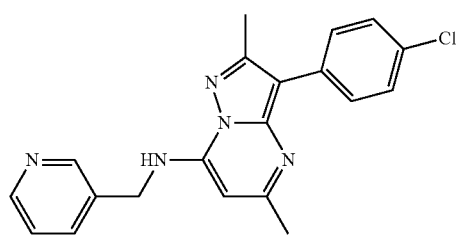 [SMILES: Cc1cc(NCc2cccnc2)n2nc(C)c(-c3ccc(Cl)cc3)c2n1]
Ex. 45

TABLE 2-continued
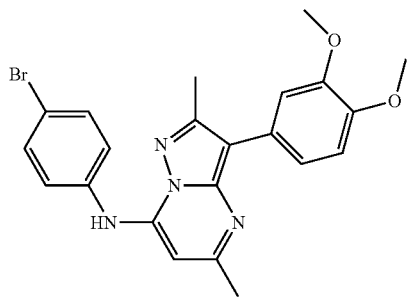 [SMILES: COc1ccc(-c2c(C)nn3c(Nc4ccc(Cl)cc4)cc(C)nc23)cc1OC] Ex. 46
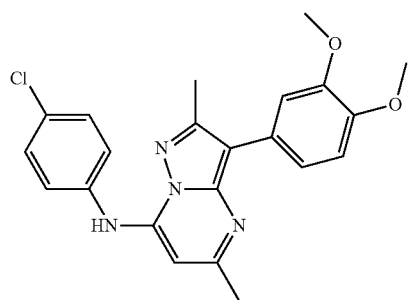 Ex. 47
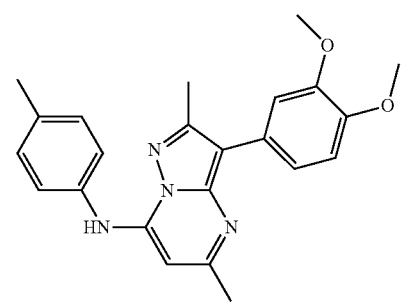 [SMILES: COc1ccc(-c2c(C)nn3c(Nc4ccc(C)cc4)cc(C)nc23)cc1OC] Ex. 48
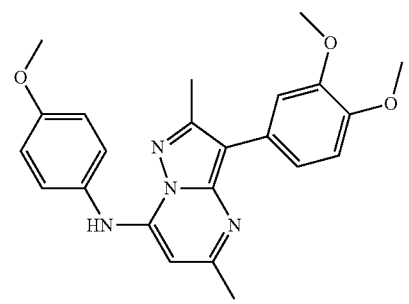 [SMILES: COc1ccc(Nc2cc(C)nc3c(-c4ccc(OC)c(OC)c4)c(C)nn23)cc1] Ex. 49
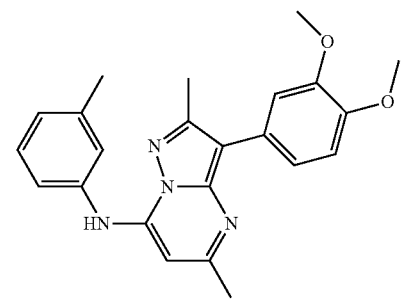 [SMILES: COc1ccc(-c2c(C)nn3c(Nc4cccc(C)c4)cc(C)nc23)cc1OC] Ex. 50

TABLE 2-continued
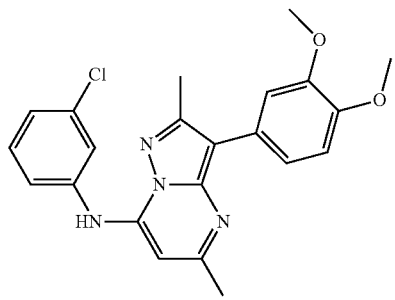 [SMILES: COc1ccc(-c2c(C)nn3c(Nc4cccc(Cl)c4)cc(C)nc23)cc1OC]
Ex. 51
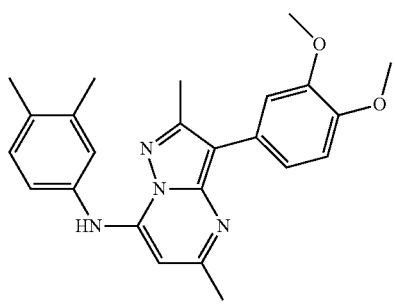 [SMILES: COc1ccc(-c2c(C)nn3c(Nc4ccc(C)c(C)c4)cc(C)nc23)cc1OC]
Ex. 52
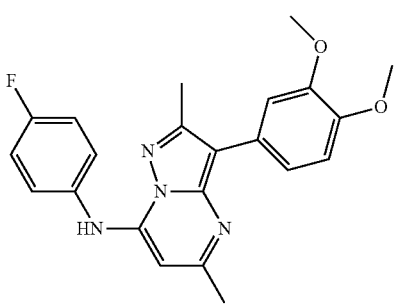 [SMILES: COc1ccc(-c2c(C)nn3c(Nc4ccc(F)cc4)cc(C)nc23)cc1OC]
Ex. 53
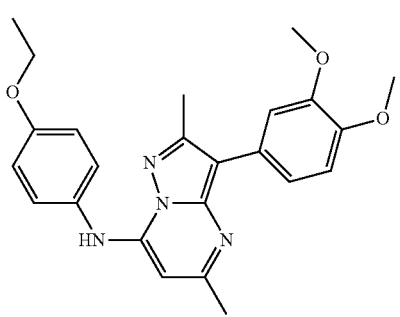 [SMILES: CCOc1ccc(Nc2cc(C)nc3c(-c4ccc(OC)c(OC)c4)c(C)nn23)cc1]
Ex. 54
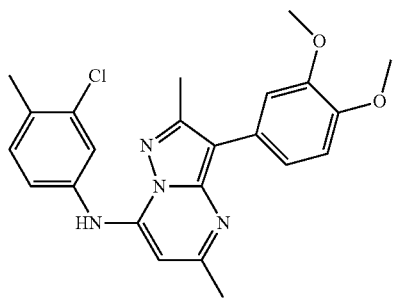
Ex. 55

TABLE 2-continued
| | |
|---|---|
| 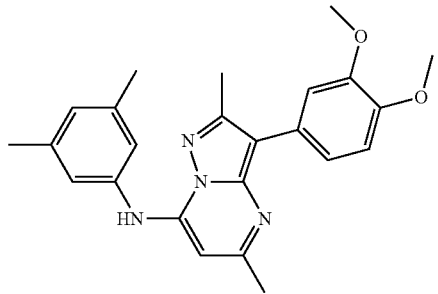 | Ex. 56 |
| 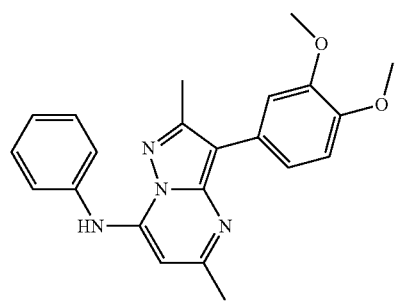 [SMILES: COc1ccc(-c2c(C)nn3c(Nc4ccccc4)cc(C)nc23)cc1OC] | Ex. 57 |
| 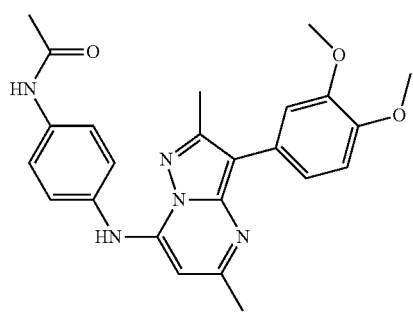 [SMILES: COc1ccc(-c2c(C)nn3c(Nc4ccc(NC(C)=O)cc4)cc(C)nc23)cc1OC] | Ex. 58 |
| 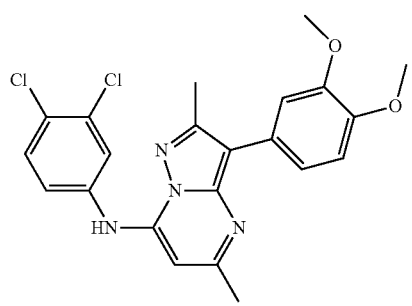 [SMILES: COc1ccc(-c2c(C)nn3c(Nc4ccc(Cl)c(Cl)c4)cc(C)nc23)cc1OC] | Ex. 59 |
| 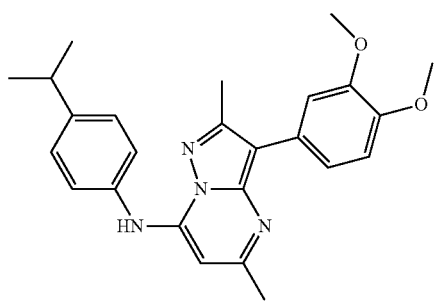 [SMILES: COc1ccc(-c2c(C)nn3c(Nc4ccc(C(C)C)cc4)cc(C)nc23)cc1OC] | Ex. 60 |

TABLE 2-continued
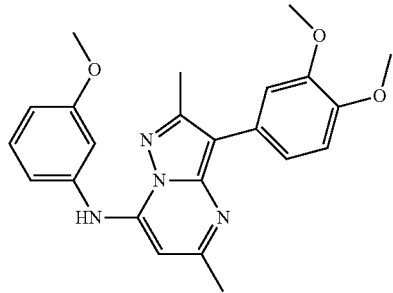 [SMILES: COc1cccc(Nc2cc(C)nc3c(-c4ccc(OC)c(OC)c4)c(C)nn23)c1]
Ex. 61
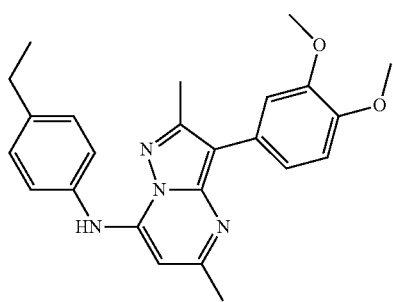 [SMILES: CCc1ccc(Nc2cc(C)nc3c(-c4ccc(OC)c(OC)c4)c(C)nn23)cc1]
Ex. 62
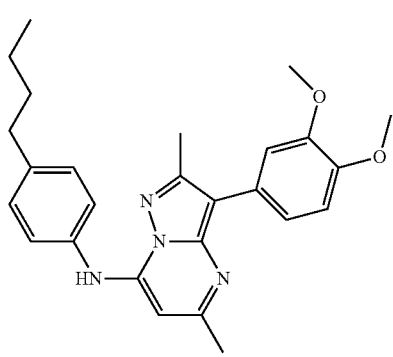 [SMILES: CCCCc1ccc(Nc2cc(C)nc3c(-c4ccc(OC)c(OC)c4)c(C)nn23)cc1]
Ex. 63
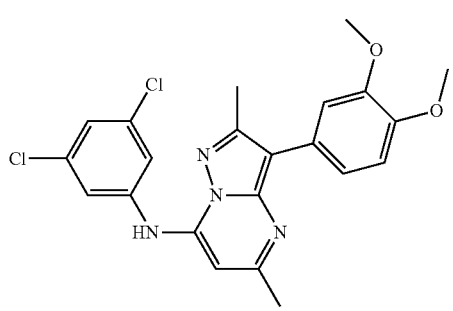 [SMILES: COc1ccc(-c2c(C)nn3c(Nc4cc(Cl)cc(Cl)c4)cc(C)nc23)cc1OC]
Ex. 64
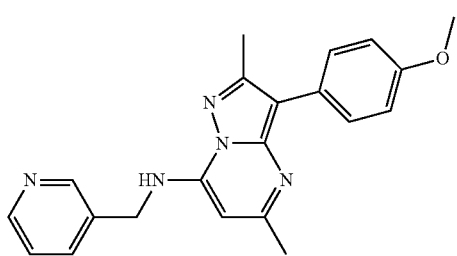 [SMILES: COc1ccc(-c2c(C)nn3c(NCc4cccnc4)cc(C)nc23)cc1]
Ex. 65

TABLE 2-continued
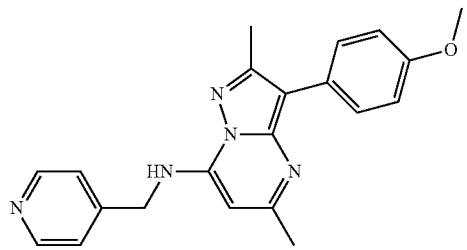 [SMILES: COc1ccc(-c2c(C)nn3c(NCc4ccncc4)cc(C)nc23)cc1]
Ex. 66
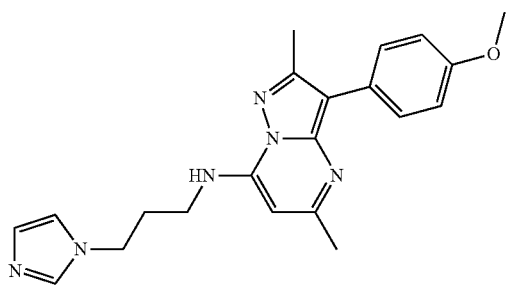 [SMILES: COc1ccc(-c2c(C)nn3c(NCCCn4ccnc4)cc(C)nc23)cc1]
Ex. 67
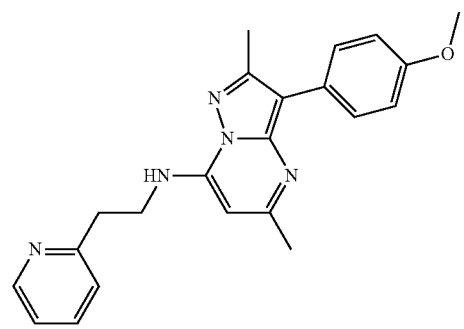 [SMILES: COc1ccc(-c2c(C)nn3c(NCCc4ccccn4)cc(C)nc23)cc1]
Ex. 68
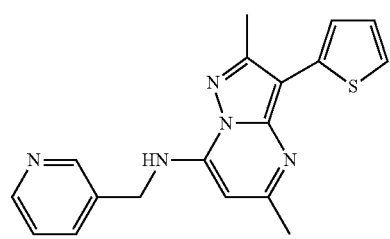 [SMILES: Cc1cc(NCc2cccnc2)n2nc(C)c(-c3cccs3)c2n1]
Ex. 69
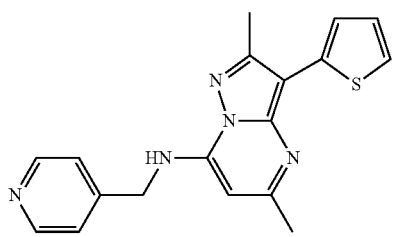 [SMILES: Cc1cc(NCc2ccncc2)n2nc(C)c(-c3cccs3)c2n1]
Ex. 70
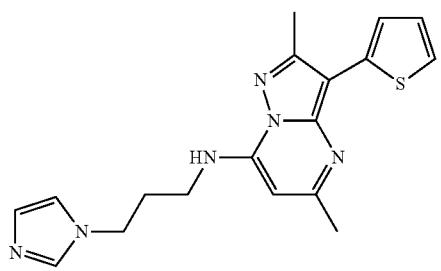 [SMILES: Cc1cc(NCCCn2ccnc2)n2nc(C)c(-c3cccs3)c2n1]
Ex. 71

TABLE 2-continued
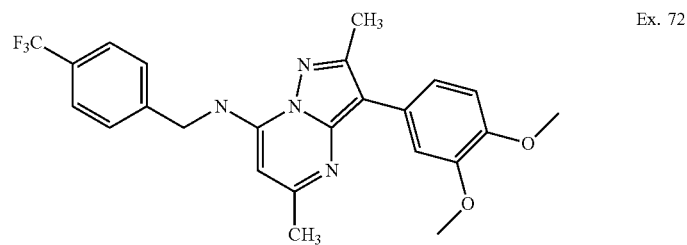
Ex. 72
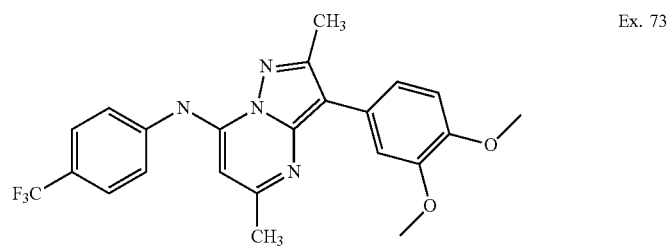
Ex. 73
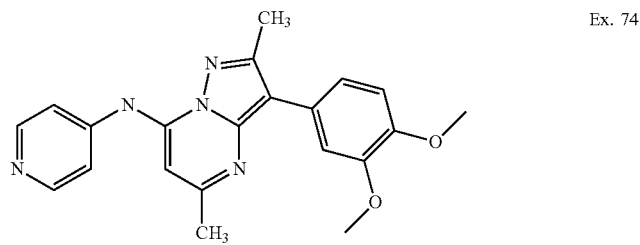
Ex. 74
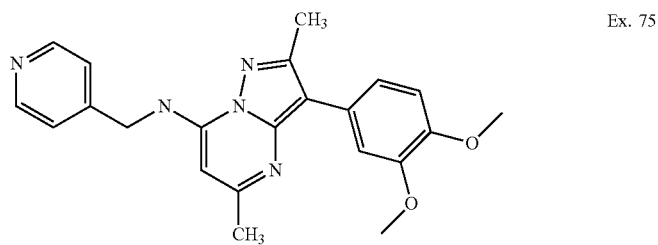
Ex. 75
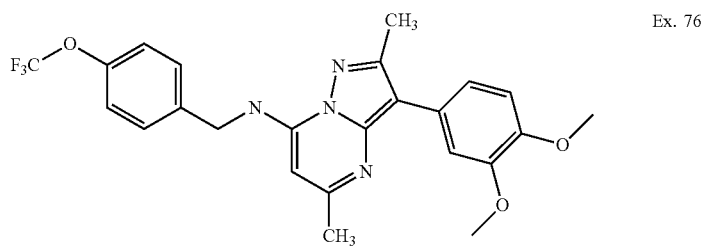
Ex. 76
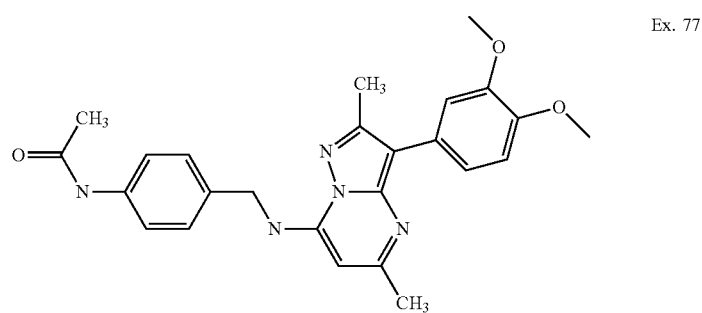
Ex. 77

TABLE 2-continued
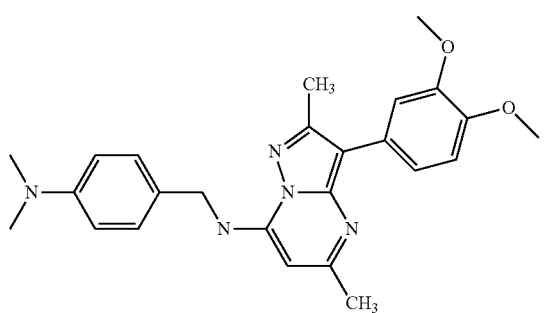
Ex. 78
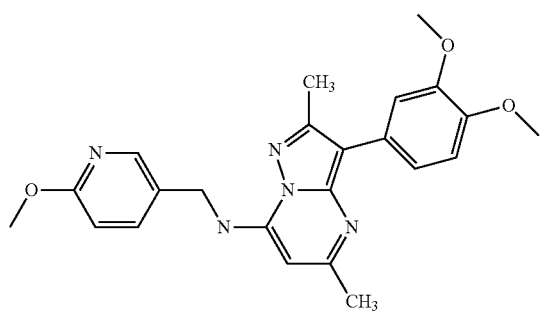
Ex. 79
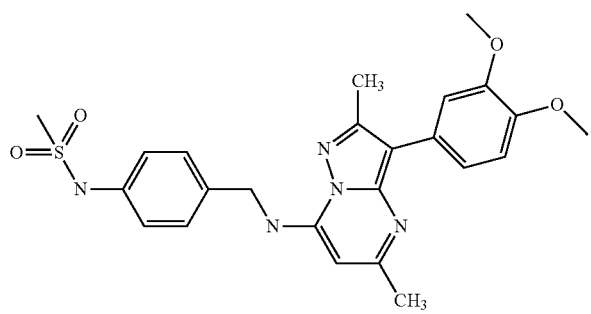 [SMILES: COc1ccc(-c2c(C)nn3c(NCc4ccc(NS(C)(=O)=O)cc4)cc(C)nc23)cc1OC]
Ex. 80
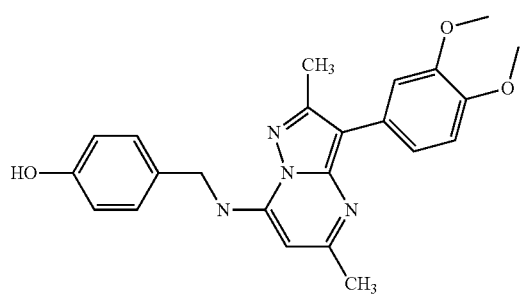
Ex. 81
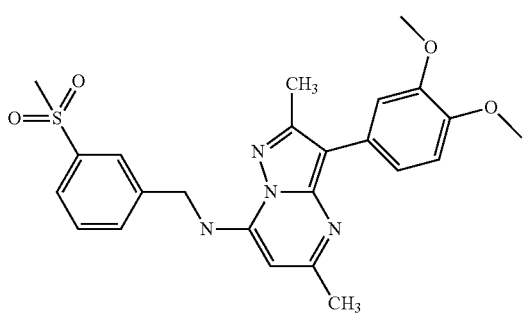 [SMILES: COc1ccc(-c2c(C)nn3c(NCc4cccc(S(C)(=O)=O)c4)cc(C)nc23)cc1OC]
Ex. 82

TABLE 2-continued
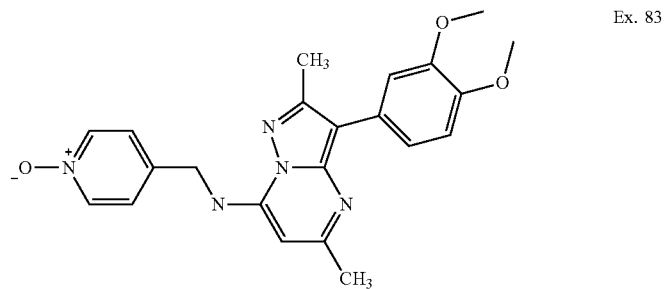
Ex. 83
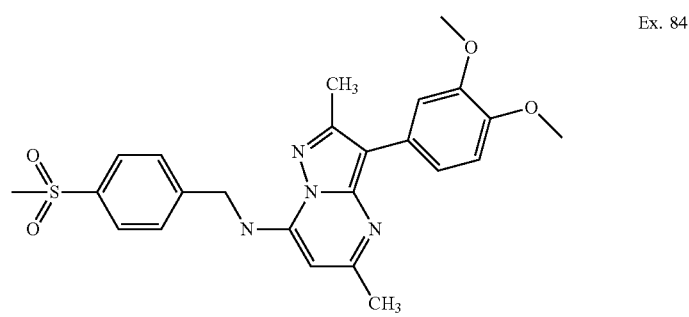
Ex. 84
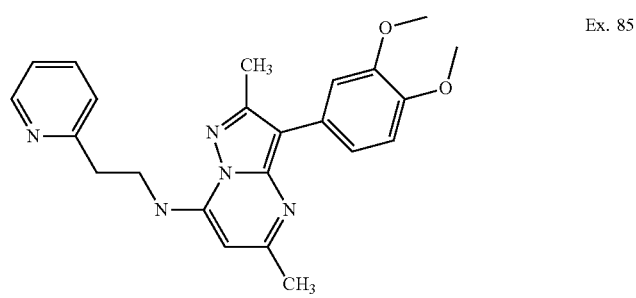
Ex. 85
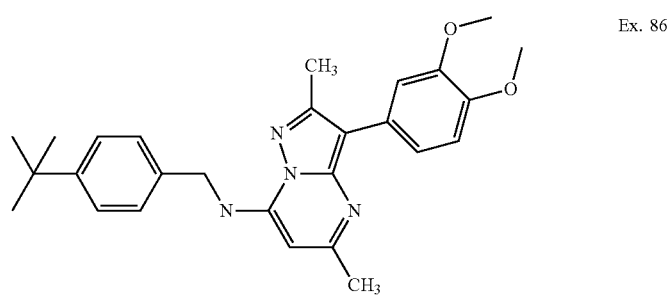
Ex. 86
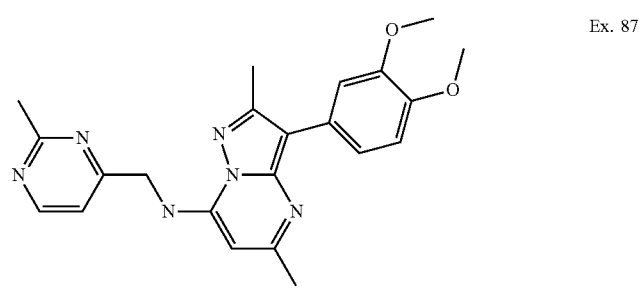
Ex. 87

TABLE 2-continued
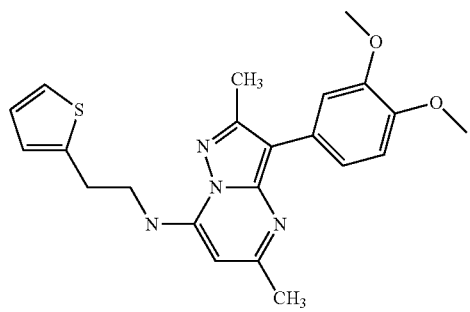 [SMILES: COc1ccc(-c2c(C)nn3c(NCCc4cccs4)cc(C)nc23)cc1OC]
Ex. 88
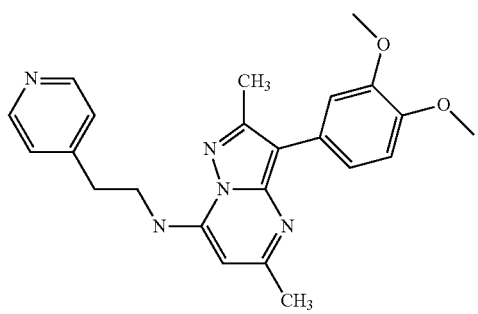 [SMILES: COc1ccc(-c2c(C)nn3c(NCCc4ccncc4)cc(C)nc23)cc1OC]
Ex. 89
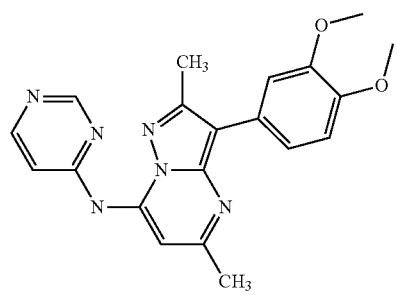 [SMILES: COc1ccc(-c2c(C)nn3c(Nc4ccncn4)cc(C)nc23)cc1OC]
Ex. 90
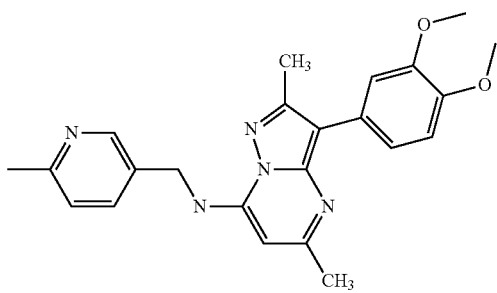
Ex. 91
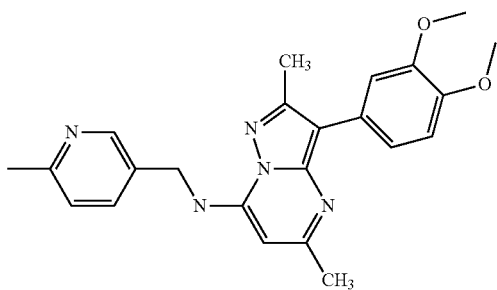
Ex. 92

TABLE 2-continued
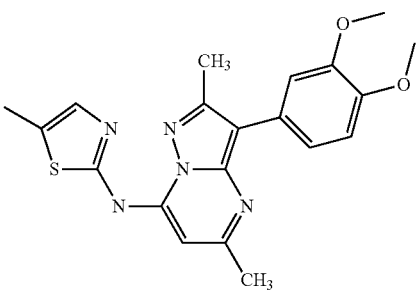 Ex. 93
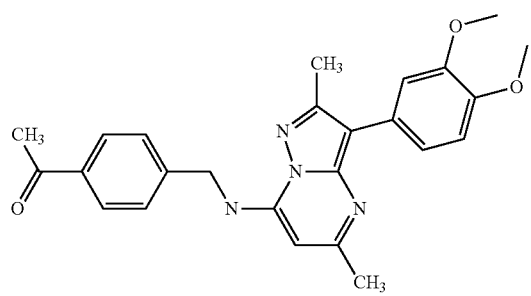 [SMILES: COc1ccc(-c2c(C)nn3c(NCc4ccc(C(C)=O)cc4)cc(C)nc23)cc1OC] Ex. 94
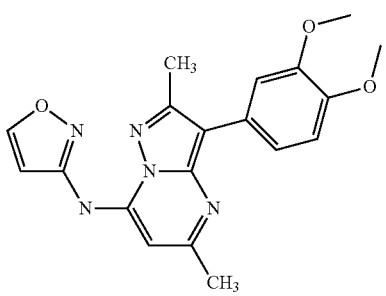 [SMILES: COc1ccc(-c2c(C)nn3c(Nc4ccon4)cc(C)nc23)cc1OC] Ex. 95
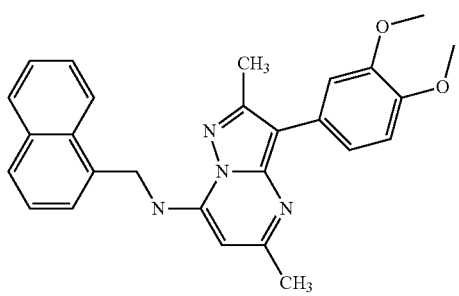 [SMILES: COc1ccc(-c2c(C)nn3c(NCc4cccc5ccccc45)cc(C)nc23)cc1OC] Ex. 96
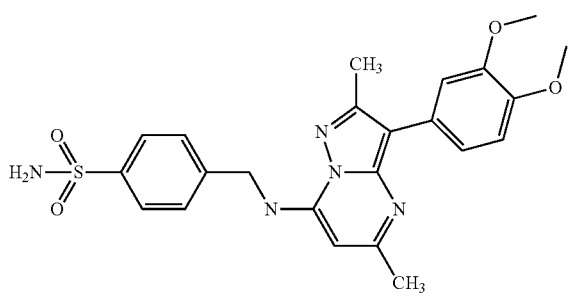 [SMILES: COc1ccc(-c2c(C)nn3c(NCc4ccc(S(N)(=O)=O)cc4)cc(C)nc23)cc1OC] Ex. 97

TABLE 2-continued
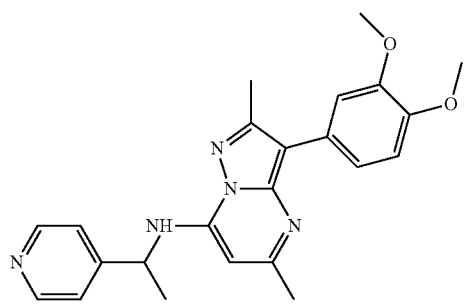 [SMILES: COc1ccc(-c2c(C)nn3c(NC(C)c4ccncc4)cc(C)nc23)cc1OC]
Ex. 98
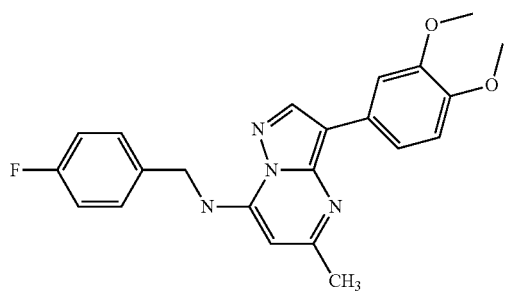 [SMILES: COc1ccc(-c2cnn3c(NCc4ccc(F)cc4)cc(C)nc23)cc1OC]
Ex. 99
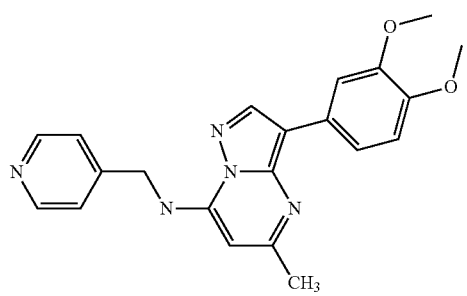 [SMILES: COc1ccc(-c2cnn3c(NCc4ccncc4)cc(C)nc23)cc1OC]
Ex. 100
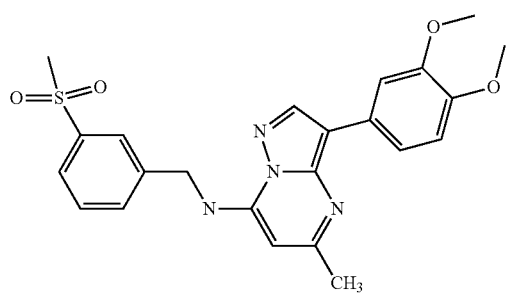 [SMILES: COc1ccc(-c2cnn3c(NCc4cccc(S(C)(=O)=O)c4)cc(C)nc23)cc1OC]
Ex. 101
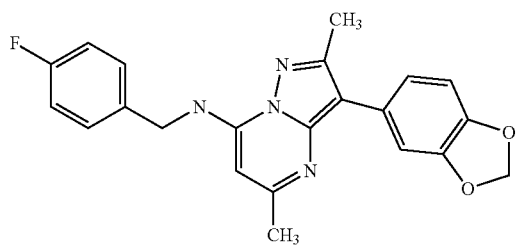 [SMILES: Cc1cc(NCc2ccc(F)cc2)n2nc(C)c(-c3ccc4c(c3)OCO4)c2n1]
Ex. 102

TABLE 2-continued
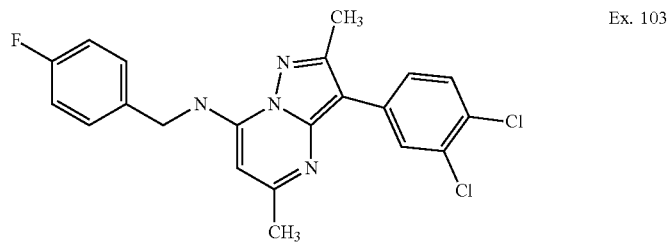 Ex. 103
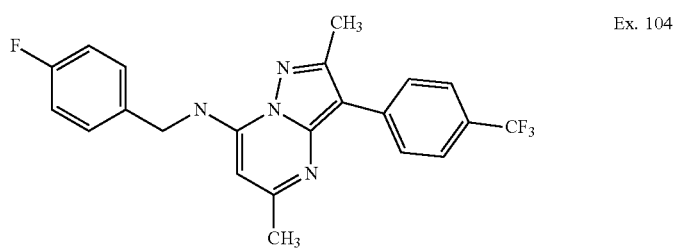 Ex. 104
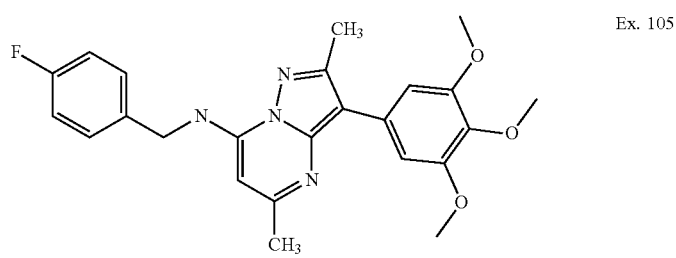 Ex. 105
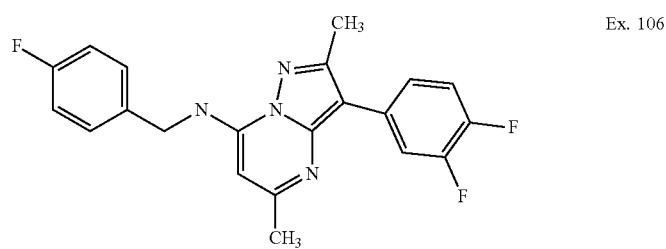 Ex. 106
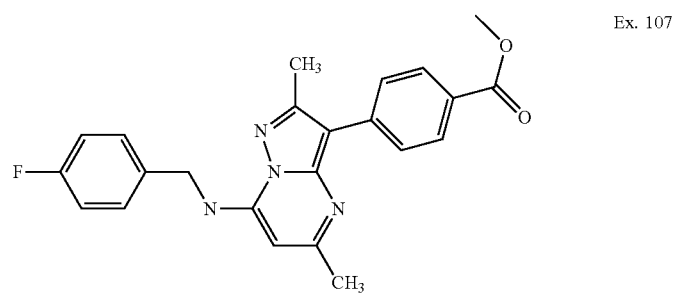 Ex. 107

TABLE 2-continued
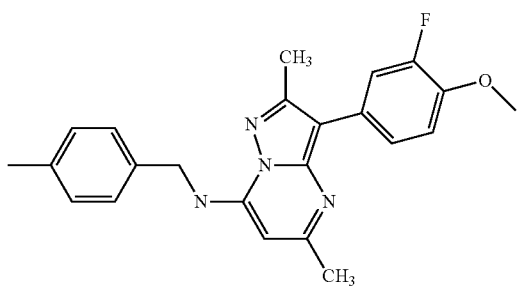
Ex. 108
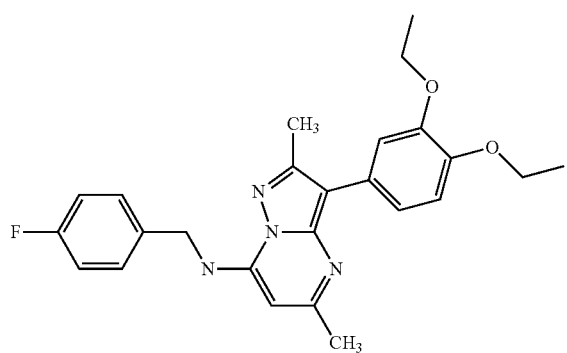 [SMILES: CCOc1ccc(-c2c(C)nn3c(NCc4ccc(F)cc4)cc(C)nc23)cc1OCC]
Ex. 109
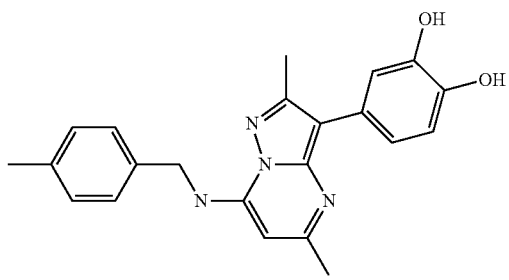 [SMILES: Cc1ccc(CNc2cc(C)nc3c(-c4ccc(O)c(O)c4)c(C)nn23)cc1]
Ex. 110
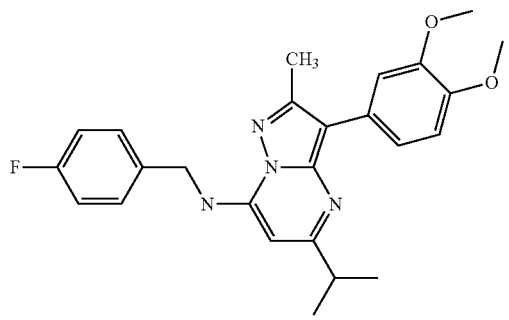 [SMILES: COc1ccc(-c2c(C)nn3c(NCc4ccc(F)cc4)cc(C(C)C)nc23)cc1OC]
Ex. 111
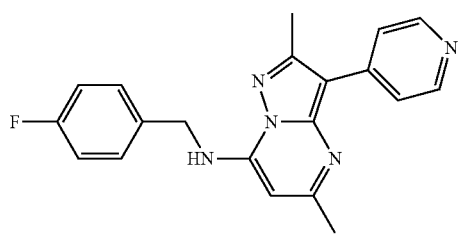 [SMILES: Cc1cc(NCc2ccc(F)cc2)n2nc(C)c(-c3ccncc3)c2n1]
Ex. 112

Examples 72-98

The compounds of Examples 72-98 were synthesized by following the General Procedure A described herein below.

General Procedure A

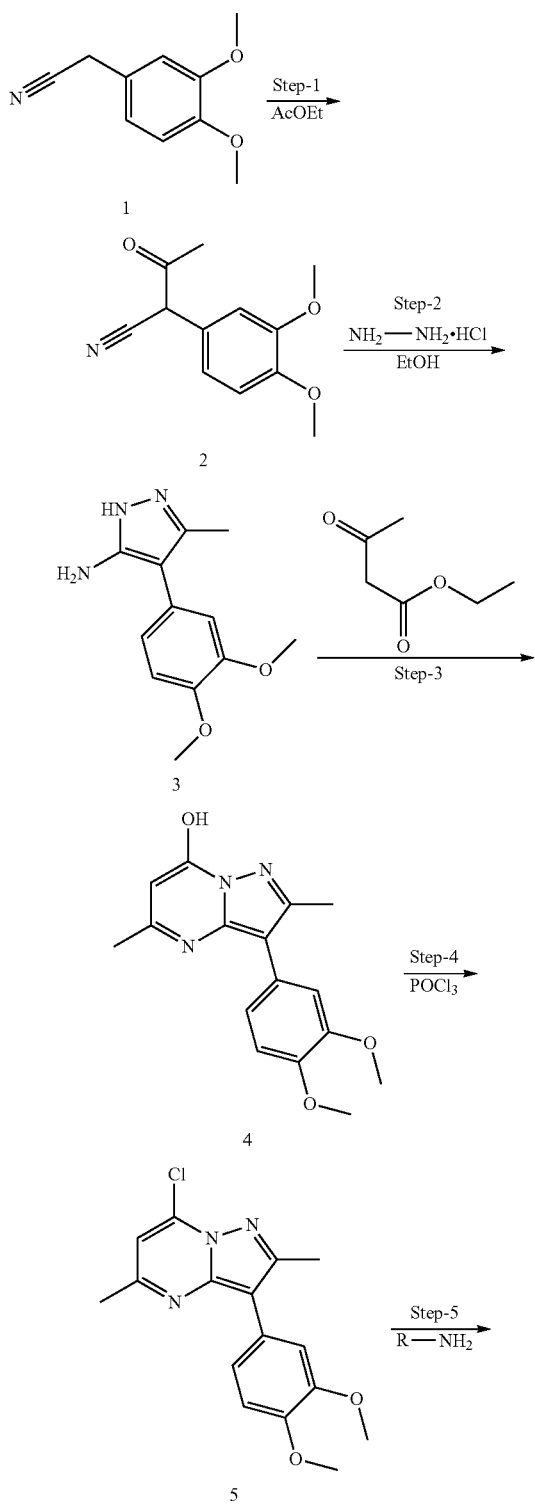

Ex. 72-98

Step-1

To a solution of 1 (10.0 g, 56.4 mmol) in ethyl acetate (200 mL) was added sodium metal (2.6 g, 112.8 mmol) portion wise at 0-5° C. under nitrogen atmosphere. The reaction mixture was stirred at room temperature for 6 h. The progress of the reaction was monitored by TLC. After completion, the reaction mixture was cooled to 0-5° C. quenched with methanol (50 mL) and the solvent was evaporated under pressure. The resultant solid was dissolved in water (100 mL) and washed with toluene (2×100 mL). The aqueous solution was acidified with acetic acid (pH: 4 to 5) and extracted with dichloromethane (3×100 mL). The combined organic layer was washed with water, brine, dried over sodium sulphate, filtered and concentrated under reduced pressure. The crude material was purified by recrystallization using ethyl acetate and hexane to afford 2 (9.5 g, 76.8%) as a pale brown solid.

Step-2

To a solution of 2 (9.0 g, 41.05 mmol) in ethanol (90 mL) were added hydrazine monohydrochloride (4.218 g, 61.57 mmol) and acetic acid (2.7 mL) at room temperature under nitrogen atmosphere. The reaction mixture was heated to 85° C. and stirred for 5-6 h. The reaction was monitored by TLC. After completion of the reaction, the reaction mixture was cooled to room temperature. The reaction mixture was quenched with water (90 mL) and concentrated under reduced pressure. The resultant aqueous layer was washed with toluene (3×45 mL) and basified with 10% aq. sodium bicarbonate solution (pH: 8-9). The aqueous layer was extracted with dichloromethane (4×50 mL). Combined organic layer was washed with water, brine, dried over sodium sulphate and concentrated under reduced pressure to afford 3 (7.6 g, 79.36%) as an off-white solid. The product obtained was used without further purification.

Step-3

To a solution of 3 (8.0 g, 21.4 mmol) in acetic acid (80 mL) was added ethyl acetoacetate (9 mL, 42.8 mmol) at room temperature and heated to 105° C. for 6 h. The progress of the reaction was monitored by TLC. After completion, the reaction mass was concentrated under high vacuum at 50° C. The resultant solid was diluted with water and extracted with dichloromethane (3×10 mL). The combined organic extract was washed with 10% sodium bicarbonate solution, water and brine. The organic extract was dried over sodium sulphate, filtered and concentrated under vacuum at 50° C. The residue obtained was treated with dichloromethane (25 mL). The solid was filtered and dried under vacuum to afford pure 4 (9.5 g, 92.54%) as a colorless solid.

Step-4

To a suspension of 4 (2.0 g, 6.68 mmol) in dry toluene (30 mL) were added phosphoryl chloride (6.24 mL, 6.68 mmol) and N,N-diethyl aniline (2.14 mL, 13.36 mmol) at room temperature under nitrogen atmosphere. The reaction mass was heated to 105° C. for 16 h. After 16 h, the reaction mass was concentrated under high vacuum at 50-55° C. and co-evaporated with toluene under high vacuum at 50-55° C. To the residue was added water (40 mL), followed by extraction with dichloromethane (3×40 mL), and the combined organic layer was washed with water, brine and dried over sodium sulphate. The organic layer was concentrated under vacuum at 45-50° C. to get crude compound. The crude compound was purified by flash column chromatography using ethyl acetate and hexane as eluant to afford 5 (2.1 g, 98.9%) as a yellow solid.

Step-5

To a solution of 5 (1.0 eq.) in toluene or acetonitrile or DMF (10-20 V) were added the respective amines (1.3 eq.) and base [DIPEA (5 V)/$K_2CO_3$/KO$^t$Bu/NaH (2.0 eq.)] sequentially. The reaction mixture was then heated to 90° C. and stirred well for 16 h. The progress of the reaction was monitored by TLC. The reaction mixture was cooled to room temperature and concentrated under reduced pressure. The residue was diluted with water (20 V) and extracted with dichloromethane (3×10 V). The combined organic extract was washed with water, brine, dried over sodium sulphate, filtered and concentrated under reduced pressure. The crude material was purified by flash column chromatography (silica gel, 50% EtOAc in hexane) to afford the desired compounds with >95% HPLC purity.

Examples 99-101

The compounds of Examples 99-101 were synthesized by following the General Procedure B.

General Procedure B

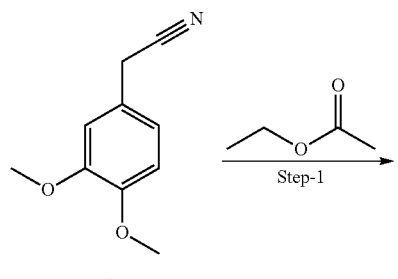

6

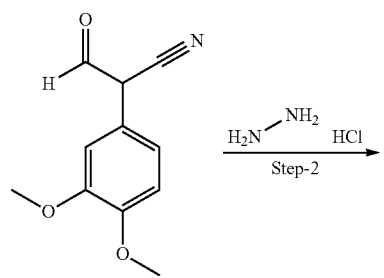

7

-continued

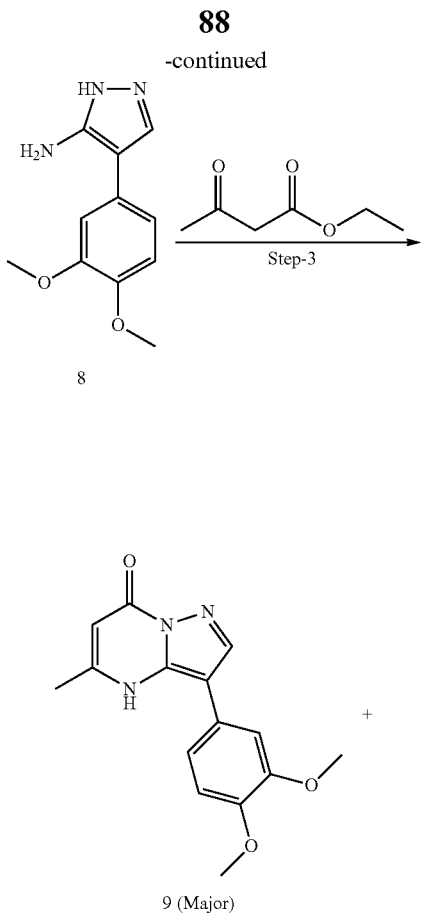

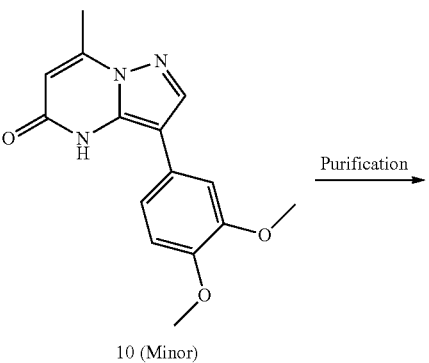

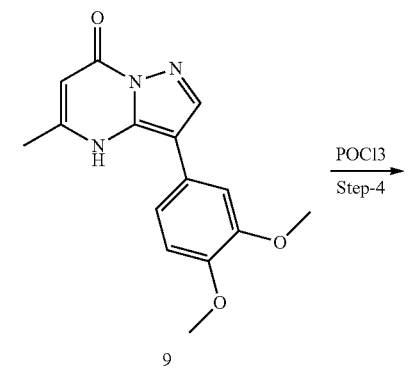

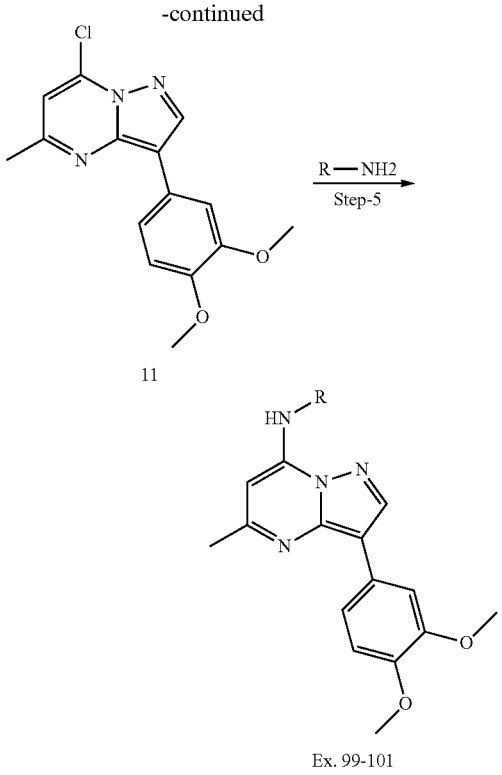

Ex. 99-101

Step-1

To a suspension of 6 (5.0 g, 28.22 mmol) and sodium methoxide (3.81 g, 70.5 mmol) in diethyl ether (75 mL) was added a solution of ethyl formate (2.6 mL, 2.4 g, 32.32 mmol) in diethyl ether (25 mL) slowly at room temperature under nitrogen atmosphere. The suspension was stirred for another 16 h at room temperature. The solid formed was filtered and washed with diethyl ether (25 mL). The solid was then dissolved in minimum amount of water and acidified with acetic acid. The solid formed was filtered, washed with water and dried under vacuum to give pure 7 (4.8 g, 83%) as a pale yellow solid.

Step-2

To a solution of 7 (4.5 g, 21.95 mmol) in ethanol (90 mL) was added hydrazine monohydrochloride (2.25 g, 32.92 mmol) and acetic acid (12 mL) at room temperature under nitrogen atmosphere. The reaction mixture was heated to 85° C. and stirred for 3-4 h. The reaction was monitored by TLC. After completion of the reaction, the reaction mixture was cooled to room temperature. The reaction mixture was quenched with water (45 mL), concentrated under reduced pressure. The resultant aqueous layer was washed with toluene (3×45 mL) and basified with 10% aq. sodium bicarbonate solution (pH: 8-9). The aqueous layer was extracted with dichloromethane (4×50 mL). Combined organic layer was washed with water, brine, dried over sodium sulphate and concentrated under reduced pressure to afford 8 (3.5 g, 75%) as an off-white solid. The product obtained was used without further purification.

Step-3

To a solution of 8 (4.0 g, 18.25 mmol) in acetic acid (40 mL) was added ethyl acetoacetate (2.55 mL, 18.253 mmol) at room temperature followed by heating to 105° C. for 6 h. The progress of the reaction was monitored by TLC. After completion, the reaction mass was concentrated under high vacuum at 50° C. The resultant solid was diluted with water and extracted with dichloromethane (3×10 mL). The combined organic extract was washed with 10% sodium bicarbonate solution, water and brine. The organic extract was dried over sodium sulphate, filtered and concentrated under vacuum at 50° C. The residue obtained was triturated with dichloromethane (25 mL) to afford pure 9 (5 g, 96%) as an off-white solid.

Step-4

To a suspension of 9 (5.0 g, 17.525 mmol) in dry toluene (75 mL) were added phosphoryl chloride (16.38 mL, 175.2 mmol) and N,N-diethyl aniline (5.62 mL, 35.05 mmol) at room temperature under nitrogen atmosphere. The reaction mass was heated to 105° C. for 16 h. After 16 h, the reaction mass was concentrated under high vacuum at 50-55° C. and co-evaporated with toluene under high vacuum at 50-55° C. To the residue was added water (40 mL), extracted with dichloromethane (3×40 mL), the combined organic layer were washed with water, brine and dried over sodium sulphate. The organic layer was concentrated under vacuum at 45-50° C. to get crude compound. The crude compound was purified by flash column chromatography using ethyl acetate and hexane as eluent to afford 11 (4.5 g, 84.58%) as a yellow solid.

Step-5

To a solution of 11 (1.0 eq.) in toluene or acetonitrile or DMF (10-20 V) were added the respective amines (1.3 eq.) and base [DIPEA (5 V)/K$_2$CO$_3$/KO$^t$Bu/NaH (2.0 eq.)] sequentially. The reaction mixture was then stirred at room temperature or at 90° C. for 16 h. The progress of the reaction was monitored by TLC. The reaction mixture was cooled to room temperature and concentrated under reduced pressure. The residue was diluted with water (20 V), extracted with dichloromethane (3×10 V). The combined organic extract was washed with water, brine, dried over sodium sulphate, filtered and concentrated under reduced pressure. The crude material was purified by flash column chromatography (silica gel, EtOAc in Hexane as eluent) to afford the desired compounds with >95% HPLC purity.

Examples 102-108

The compounds of Examples 102-108 were synthesized by following the General Procedure E described herein below.

General Procedure E

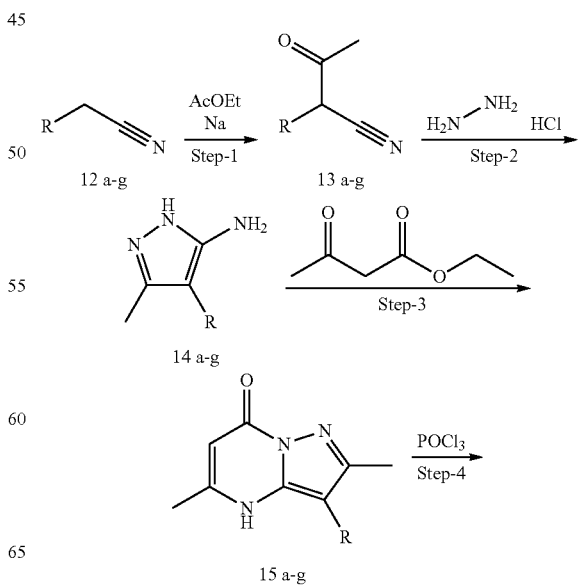

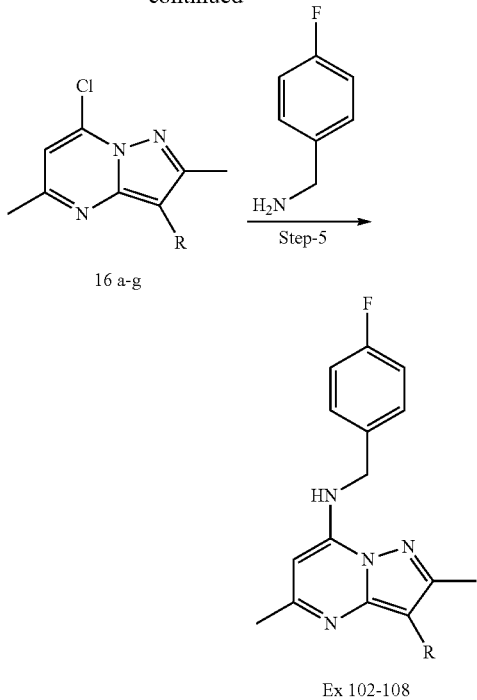

Ex 102-108

Step-1

To a solution of nitrile 12a-g (1.0 eq.) in ethyl acetate (20 Vol.) was added sodium metal (2.0 eq.) portion wise at 0-5° C. under nitrogen atmosphere. The reaction mixture was stirred at room temperature for 6 h. The progress of the reaction was monitored by TLC. After completion, the reaction mixture was cooled to 0-5° C. followed by quenching with methanol (5 Vol.) and the solvent was evaporated under pressure. The resultant solid was dissolved in water (10 Vol.) and washed with toluene (2×10 Vol.). The aqueous solution was acidified with acetic acid (pH: 4 to 5) and extracted with dichloromethane (3×10 Vol.). The combined organic layer was washed with water, brine, dried over sodium sulphate, filtered and concentrated under reduced pressure. The crude material was purified by recrystallization using ethyl acetate and hexane to afford 13a-g.

Step-2

To a solution of 13a-g (1.0 eq.) in ethanol (10 Vol.) were added hydrazine monohydrochloride (1.5 eq.) and acetic acid (1.2 eq.) at room temperature under nitrogen atmosphere. The reaction mixture was heated to 85° C. and stirred for 5-6 h. The reaction was monitored by TLC. After completion of the reaction, the reaction mixture was cooled to room temperature. The reaction mixture was quenched with water (10 Vol.) and concentrated under reduced pressure. The resultant aqueous layer was washed with toluene (3×5 Vol.) and basified with 10% aq. sodium bicarbonate solution (pH: 8-9). The aqueous layer was extracted with dichloromethane (4×5 Vol.). Combined organic layer was washed with water, brine, dried over sodium sulphate and concentrated under reduced pressure to afford 14a-g. The product obtained was used without further purification.

Step-3

To a solution of 14a-g (1.0 eq.) in acetic acid (10 Vol.) was added ethyl acetoacetate (2.0 eq.) at room temperature and heated to 105° C. for 6 h. The progress of the reaction was monitored by TLC. After completion, the reaction mass was concentrated under high vacuum at 50° C. The resultant solid was diluted with water and extracted with dichloromethane (3×2 Vol.). The combined organic extract was washed with 10% sodium bicarbonate solution, water and brine. The organic extract was dried over sodium sulphate, filtered and concentrated under vacuum at 50° C. The residue obtained was treated with dichloromethane (25 mL). The solid was filtered and dried under vacuum to afford pure 15a-g.

Step-4

To a suspension of 15a-g (1.0 eq.) in dry toluene (15 Vol.) were added phosphoryl chloride (1.0 eq.) and N, N-diethyl aniline (2.0 eq.) at room temperature under nitrogen atmosphere. The reaction mass was heated to 105° C. for 16 h. After 16 h, the reaction mass was concentrated under high vacuum at 50-55° C. and co-evaporated with toluene under high vacuum at 50-55° C. To the residue was added water (20 Vol.) followed by extraction with dichloromethane (3×20 Vol.), and the combined organic layer was washed with water, brine and dried over sodium sulphate. The organic layer was concentrated under vacuum at 45-50° C. to get crude compound. The crude compound was purified by flash column chromatography to afford 16a-g.

Step-5

To a solution of 16a-g (1.0 eq.) in toluene (20 V) was added the 4-fluorobenzylamine (1.3 eq.) and DIPEA (5 V) sequentially. The reaction mixture was then heated to 90° C. and stirred well for 16 h. The progress of the reaction was monitored by TLC. The reaction mixture was cooled to room temperature and concentrated under reduced pressure. The residue was diluted with water (20 V) and extracted with dichloromethane (3×10 V). The combined organic extract was washed with water, brine, dried over sodium sulphate, filtered and concentrated under reduced pressure. The crude material was purified by flash column chromatography (silica gel, ethyl acetate in hexane) to afford the desired compounds with >95% HPLC purity.

Example 109

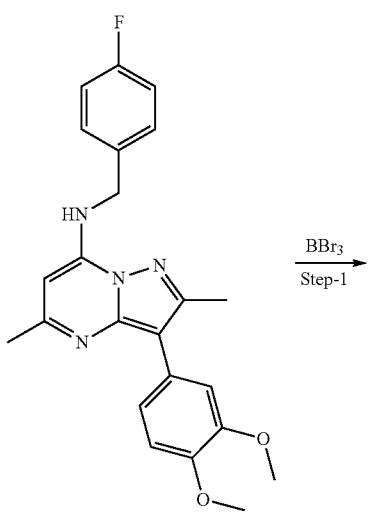

Ex 9

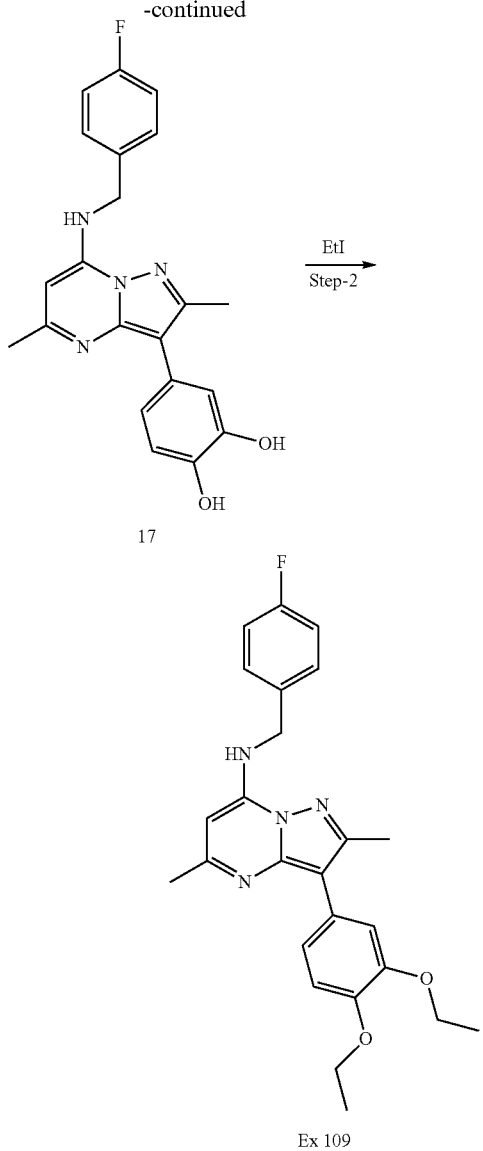

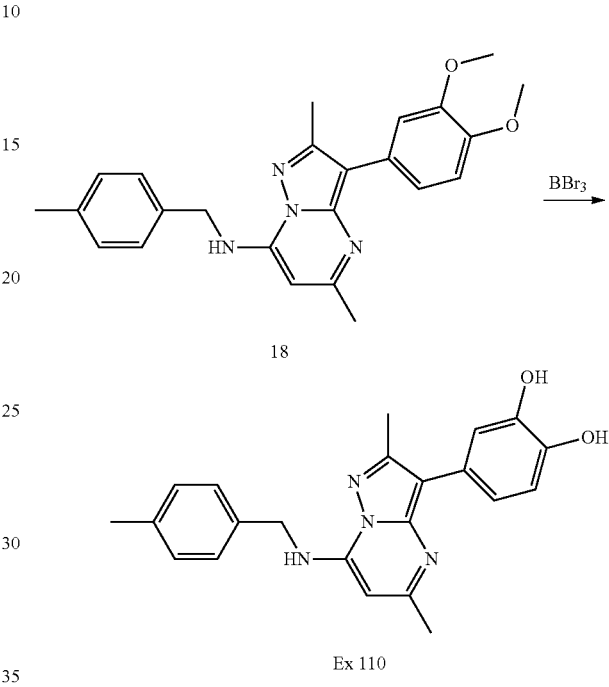

Ex 110

Step-1

To a solution of Ex 9 (2.0 g, 4.926 mmol) in dichloromethane (50 mL) was added BBr₃ (1M solution in CH₂Cl₂, 25 mL, 25 mmol) slowly at 0-5° C. After addition, the reaction mixture was allowed to attain room temperature with stirring. After 4 h, the reaction mixture was quenched with methanol (40 mL). The reaction mixture was concentrated under reduced pressure. The residue obtained was diluted with water (10 mL) and extracted with CH₂Cl₂ (3×20 mL). The combined organic extract was washed with water, brine, dried over sodium sulphate, filtered and concentrated under reduced pressure. The crude material was purified by recrystallization in dichloromethane to afford 17 (1.8 g, 96.77%) as a brown solid.

Step-2

To a solution of 17 (1.8 g, 4.762 mmol) in DMF (36 mL) was added cesium carbonate (3.099 g, 9.51 mmol) at room temperature. To this mixture iodoethane (7.427 g, 3.83 mL, 47.62 mmol) was added at the same temperature and stirred well. After 16 h, the reaction mixture was quenched with ice-cold water (180 mL) and extracted with ethyl acetate (3×20 mL). The combined organic extract was washed with water, brine, dried over sodium sulphate, filtered and concentrated under reduced pressure. The crude material was purified by flash column chromatography (silica gel, ethyl acetate in hexane as eluent) followed by recrystallization in ethyl acetate to give Ex 109 (0.9 g, 43.06%) as an off-white solid.

Example 110

To a solution of 18 which was formed as described in General Procedure A (500 mg, 1.242 mmol) in dichloromethane (12.5 mL) was added BBr₃ (1M solution in CH₂Cl₂, 7.86 mL, 7.86 mmol) slowly at 0-5° C. After addition, the reaction mixture was allowed to attain room temperature with stirring. After 4 h, the reaction mixture was quenched with methanol (10 mL). The reaction mixture was concentrated under reduced pressure. The residue obtained was diluted with water (10 mL) and extracted with CH₂Cl₂ (3×10 mL). The combined organic extract was washed with water, brine, dried over sodium sulphate, filtered and concentrated under reduced pressure. The crude material was purified by flash column chromatography (silica gel, ethyl acetate in hexane) followed by recrystallization in dichloromethane to afford Ex 110 (110 mg, 23.65%) as an off-white solid.

Example 111

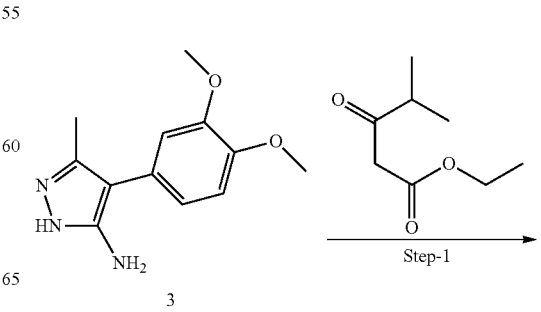

-continued

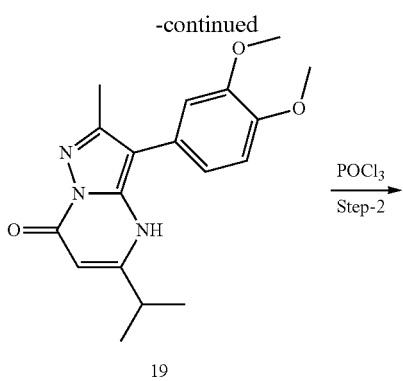

19

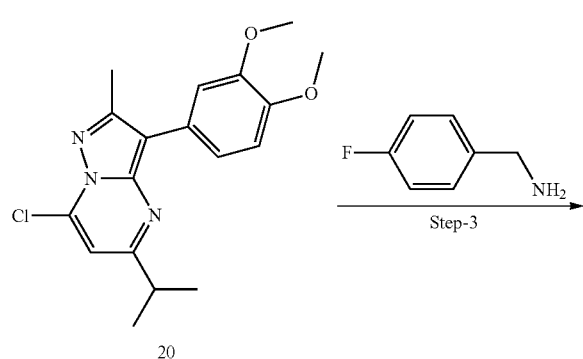

20

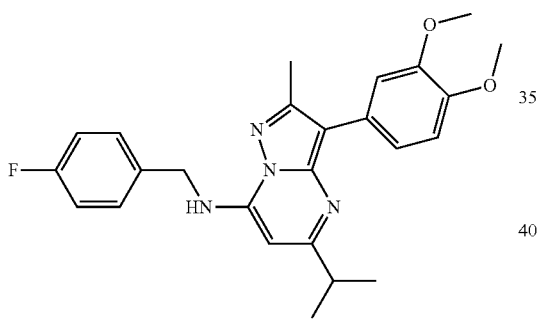

Ex 111

Step-1

To a solution of 3 (500 mg, 4.28 mmol) in acetic acid (10 mL) was added methyl isobutyl acetate (0.87 mL, 8.57 mmol) at room temperature and stirred at 105° C. for 16 h. The progress of the reaction was monitored by TLC. After completion, the reaction mixture was concentrated under high vacuum at 50° C. The resultant solid was diluted with water and extracted with dichloromethane (3×10 mL). The combined organic extract was washed with 10% sodium bicarbonate solution, water and brine. The organic extract was dried over sodium sulphate, filtered and concentrated under vacuum to afford 19 (600 mg, 85.71%) as a brown solid.

Step-2

To a suspension of 19 (1.0 g, 3.05 mmol) in dry toluene (15 mL) were added phosphoryl chloride (7.14 mL, 76.36 mmol) and N,N-diethyl aniline (0.98 mL, 6.11 mmol) at room temperature under nitrogen atmosphere. The reaction mass was heated to 105° C. for 16 h. After 16 h, the reaction mixture was concentrated under reduced pressure at 50-55° C. and co-evaporated with toluene under reduced pressure. To the resultant solid, was added water (40 mL) and extracted with dichloromethane (3×40 mL). The combined organic layer was washed with water, brine, dried over sodium sulphate and concentrated under reduced pressure to get crude compound. The crude compound was purified using flash column chromatography (silica gel, using ethyl acetate and hexane as eluent) to afford 20 (550 mg, 52.08%) as a yellow solid.

Step-3

To the solution of 20 (500 mg, 1.445 mmol) in toluene (5 mL) were added 4-fluoro benzyl amine (0.215 mL, 1.88 mmol) and DIPEA (4 mL, 22.965 mmol), followed by heating to 90° C. for 16 h. The progress of the reaction was monitored by TLC. After completion, the reaction mass was cooled to room temperature and concentrated under reduced pressure. The residue was diluted with water (30 mL) extracted with dichloromethane (3×10 mL). The combined organic layer was washed with water, brine, dried over sodium sulphate, filtered and concentrated under high vacuum at 45-50° C. The crude material was purified by flash column chromatography (silica gel, using ethyl acetate in hexane as eluent) to afford Ex 111 (280 mg, 15.92%) as a yellow solid.

Example 112

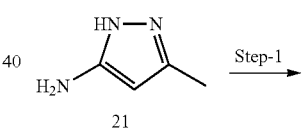

21

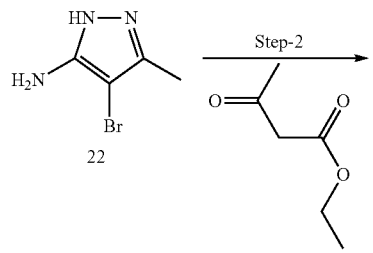

22

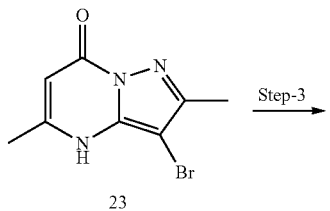

23

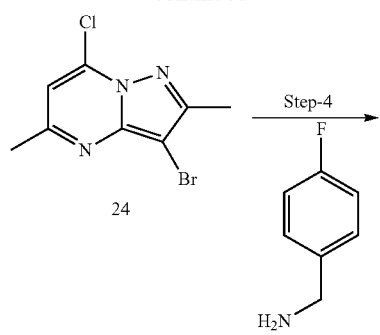

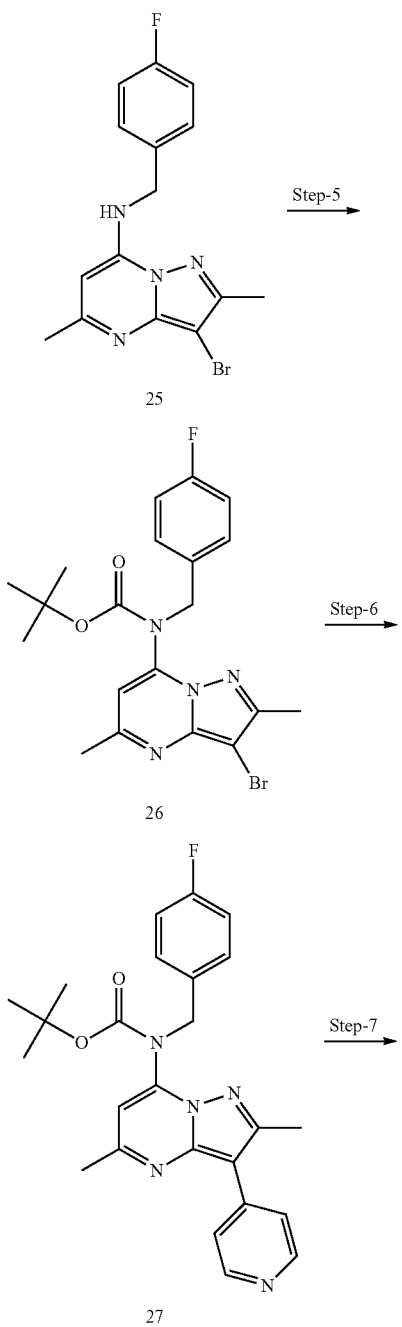

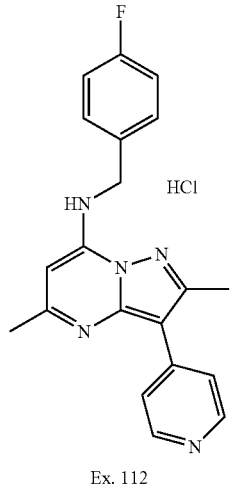

Ex. 112

Step-1
To a solution of 21, (10 g, 102.97 mmol) in acetonitrile (250 mL), was added AIBN (1.65 g, 10.29 mmol) at 0-5° C. To the reaction mixture was slowly added N-bromosuccinimide (18.33 g, 102.97 mmol) while maintaining temperature between 0-5° C. After the addition, the reaction mixture was allowed to attain room temperature gradually and stirred for 2 h. The progress of the reaction was monitored with TLC. Starting amine was completely consumed. The reaction mixture was concentrated under reduced pressure. The residue was diluted with water (100 mL) and the insoluble material was filtered. The filtrate was treated with 10% NaHCO₃ solution (100 mL) and extracted with dichloromethane (3×100 mL). The combined organic extract was washed with water, saturated brine and dried over sodium sulphate. The organic layer was filtered and dried under reduced pressure. The crude material obtained was purified by flash column chromatography (Silica gel, 30% Ethyl acetate in hexane) to afford 22 (14.0 g, 77.25%) as a brown solid.

Step-2
To a solution of 22 (14.0 g, 79.54 mmol) in ethanol (280 mL) were added ethyl acetoacetate (15.15 mL, 15.59 g, 119.79 mmol) and acetic acid (4.55 mL, 79.54 mmol) at room temperature under nitrogen atmosphere. The reaction mixture was then heated to 85° C. and stirred for 16 h. The progress of the reaction was monitored by TLC. After 16 h, the reaction mixture was concentrated completely under reduced pressure. The resultant solid was treated with CH₂Cl₂ (30 mL) and the solid was filtered. The filtered solid was dried under high vacuum at 45-55° C. to afford 23 (10.7 g, 55.57%) as a pale yellow solid.

Step-3
To a suspension of 23 (10.5 g, 43.38 mmol) in toluene (157.5 mL) were added N,N-diethyl aniline (20.63 mL, 130.16 mmol) and phosphorous oxychloride (10.14 mL, 108.47 mmol) at room temperature. The reaction mixture was heated to 105° C. for 16 h. The progress of the reaction was monitored by TLC. After 16 h, the reaction mass was cooled to room temperature and quenched with saturated brine solution, and filtered through Celite bed. The layers were separated and the toluene layer was washed with saturated sodium bicarbonate solution and saturated brine solution. The organic layer was dried over sodium sulphate, filtered and concentrated to get crude material. The crude material was purified by flash column chromatography (Silica gel, 5-10% Ethyl acetate in Hexane) to get 24 (10.0 g, 88.49%) as a pale yellow solid.

Step-4

To a solution of 24 (10.0 g, 38.38 mmol) in acetonitrile (100 mL) were added 4-fluoro benzyl amine (5.27 mL, 46.06 mmol) and DIPEA (32.85 mL, 191.9 mmol) at room temperature. The reaction mixture was heated to 80° C. for 16 h. The progress of the reaction was monitored by TLC. After 16 h, the reaction mixture was cooled to room temperature and concentrated under reduced pressure. The resultant solid was diluted with water (100 mL) and extracted with ethyl acetate (3×100 mL). The combined organic layer was washed with water, brine, dried over sodium sulphate. The organic layer was filtered and concentrated under reduced pressure to get crude compound. The crude material was purified by flash column chromatography (Silica gel, 5-10% Ethyl acetate in Hexane) to afford 25 (12.0 g, 89.55%) as a colorless solid.

Step-5

To a solution of 25 (2.0 g, 5.727 mmol) in dichloromethane (30 mL) were added DMAP (34.98 mg, 0.286 mmol), Boc-anhydride (1.44 mL, 6.30 mmol) at 10-15° C. under nitrogen atmosphere. The reaction mixture was slowly warmed to room temperature and stirred for 6 h. The progress of the reaction was monitored by TLC. After completion, the reaction mixture was cooled to 0-5° C. and quenched with water. The mixture was extracted with $CH_2Cl_2$ (3×20 mL). The combined organic layer was washed with brine, dried over sodium sulphate, filtered and concentrated under reduced pressure. The crude compound was purified by recrystallization using $CH_2Cl_2$ and Hexane solvent combination to afford 26 (2.12 g, 82.38%) as an off-white solid.

Step-6

To a solution of 26 (500 mg, 1.113 mmol) in DME:water (5:1, 10 mL) were added 4-pyridine boronic acid (205.23 mg, 1.66 mmol) and cesium carbonate (1.088 mg, 3.339 mmol) at room temperature under argon atmosphere. The reaction mixture was degassed thoroughly with argon. To the reaction mixture was added $Pd(PPh_3)_4$ (258 mg, 0.0445 mmol) under argon atmosphere. The reaction mixture was stirred for 3 h at 100° C. under microwave condition. The progress of the reaction of was monitored by LCMS. The reaction mixture was diluted with water and extracted with ethyl acetate (3×10 mL). The combined organic layer was washed with brine and dried over sodium sulphate. The organic layer was concentrated under reduced pressure to get crude material. The crude compound was purified by flash column chromatography to get 27 (0.2 g, 40%) as a brown semi solid.

Step-7

To a solution of 27 (200 mg) in 1,4-dioxane (2 mL) was added HCl solution (15 mL, 4M in dioxane) at 10-15° C. under nitrogen atmosphere. The reaction mixture was stirred for 16 h at room temperature. The solid formed was filtered. The solid was again dissolved in water (4 mL) and the insoluble material was filtered. The filtrate was concentrated under reduced pressure to get Ex. 112 in the salt form (60 mg, 35%) as a pale yellow solid.

Analytical data for the compounds of Examples 72-112 are shown in Table 3.

TABLE 3

| Ex. | Analytical Data |
|---|---|
| 72 | $^1$H-NMR (MeOD, 300 MHz): δ 7.65 (dd, 4 H), 7.26 (d, 2 H), 7.13 (d, 1 H), 7.05 (d, 1 H), 5.92 (s, 1 H), 4.79 (s, 2 H), 3.89 (s, 6 H), 2.53 (s, 3 H), 2.37 (s, 3 H), LCMS: 457.2 [M + H], HPLC purity: 98.46% |
| 73 | $^1$H-NMR (MeOD, 300 MHz): δ 7.79 (d, 2 H), 7.67 (d, 2 H), 7.30 (d, 1 H), 7.15 (d, 1 H), 7.08 (d, 1H), 6.45 (s, 1 H), 3.90 (s, 6 H), 2.58 (s, 3 H), 2.47 (s, 3 H), LCMS: 443.2 [M + H], HPLC purity: 99.99% |
| 74 | $^1$H-NMR (MeOD, 300 MHz): δ 8.53 (d, 2 H), 7.37 (d, 1 H), 7.22 (m, 2 H), 7.09 (m, 3 H), 3.90 (s, 6 H), 2.70 (s, 3 H), 2.58 (s, 3 H), LCMS: 376.5 [M + H], HPLC purity: 95.69% |
| 75 | $^1$H-NMR (MeOD, 300 MHz): δ 8.52 (d, 2 H), 7.48 (d, 2 H), 7.26 (d, 1 H), 7.14 (d, 1 H), 7.09 (dd, 1 H) 5.90 (s, 1 H), 4.78 (s, 2 H), 3.89 (s, 6 H), 2.54 (s, 3 H), 2.37 (s, 3 H), LCMS: 390.6 [M + H], HPLC purity: 98.97% |
| 76 | $^1$H-NMR (MeOD, 300 MHz): δ 7.51 (d, 2 H), 7.25 (dd, 2 H), 7.12 (d, 1 H), 7.06 (q, 1 H), 5.93 (s, 1 H), 4.70 (s, 2 H), 3.88 (s, 6 H), 2.51 (s, 3 H), 2.37 (s, 3 H), LCMS: 473.7 [M + H], HPLC purity: 100% |
| 77 | $^1$H-NMR (MeOD, 300 MHz): δ 7.56 (d, 2 H), 7.38 (d, 2 H), 7.25 (s, 1 H), 7.09 (m, 2 H), 5.95 (s, 1 H), 4.63 (s, 2 H), 3.88 (s, 6 H), 2.52 (s, 3 H), 2.39 (s, 3 H), 2.12 (s, 3 H), LCMS: 446.5 [M + H], HPLC purity: 99.56% |
| 78 | $^1$H-NMR (MeOD, 400 MHz): δ 7.23 (q, 3 H), 7.08 (dd, 1 H), 7.02 (d, 1 H), 6.77 (dd, 2 H), 5.97 (s, 1 H), 4.52 (s, 2 H), 3.86 (s, 6 H), 2.91 (s, 3 H), 2.48 (s, 3 H), 2.37 (s, 3 H), LCMS: 432.5 [M + H], HPLC purity: 99.59% |
| 79 | $^1$H-NMR (MeOH, 400 MHz): δ 8.19 (s, 1 H), 7.74 (d, 1 H), 7.23 (s, 1 H), 7.09 (dd, 1 H), 7.02, (d, 1 H), 6.88 (d, 1 H), 6.00 (s, 1 H), 4.60 (s, 2 H), 3.89 (s, 3 H), 3.86 (s, 3 H), 2.48 (s, 3 H), 2.39 (s, 3 H), LCMS: 420.4 [M + H], HPLC purity: 99.86% |
| 80 | $^1$H-NMR (MeOH, 400 MHz): δ 7.39 (d, 2 H), 7.23 (m, 3 H), 7.09 (dd, 1 H), 7.02 (d, 1 H), 5.94 (s, 1 H), 4.62 (s, 2 H), 3.86 (s, 6 H), 2.93 (s, 3 H), 2.49 (s, 3 H), 2.36 (s, 3 H), LCMS: 482.5 [M + H], HPLC purity: 99.20% |
| 81 | $^1$H-NMR (MeOH, 400 MHz): δ 7.23 (m, 3 H), 7.09 (dd, 1 H), 7.02 (d, 1 H), 6.77 (dd, 2 H), 5.96 (s, 1 H), 4.54 (s, 2 H), 3.86 (s, 6 H), 2.48 (s, 3 H), 2.37 (s, 3 H), LCMS: 405.6 [M + H], HPLC purity: 99.74% |
| 82 | $^1$H-NMR (DMSO, 400 MHz): δ 8.57 (t, 1 H), 8.02 (s, 1 H), 7.82 (d, 1 H), 7.76 (d, 1 H), 7.63 (t, 1 H), 7.21 (dd, 1 H), 7.01 (d, 1 H), 6.05 (s, 1 H), 4.70 (d, 2 H), 3.78 (s, 6 H), 3.20 (s, 3 H), 2.55 (s, 3 H), 2.37 (s, 3 H), LCMS: 467.4 [M + H], HPLC purity: 99.78% |
| 83 | $^1$H-NMR (MeOH, 400 MHz): δ 8.21 (d, 2 H), 7.47 (d, 2 H), 7.14 (d, 1 H), 7.01 (dd, 1H), 6.94 (d, 1 H), 5.83 (s, 1 H), 4.50 (s, 2 H), 3.78 (s, 6 H), 2.42 (s, 3 H), 2.28 (s, 3 H), LCMS: 406.5 [M + H], HPLC purity: 98.91% |

TABLE 3-continued

| Ex. | Analytical Data |
|---|---|
| 84 | $^1$H-NMR (MeOH, 400 MHz): δ 7.97 (dd, 2 H), 7.69 (d, 2 H), 7.26. (d, 1 H), 7.12 (dd, 1H), 7.05 (d, 1 H), 5.93 (s, 1 H), 4.82 (s, 2 H), 3.90 (s, 6 H), 3.13 (s, 3 H), 2.54 (s, 3 H), 2.38 (s, 3 H), LCMS: 467.3 [M + H], HPLC purity: 99.93% |
| 85 | $^1$H-NMR (MeOH, 300 MHz): δ 8.83 (d, 1 H), 8.63 (m, 1 H), 8.13 (d, 1 H), 8.04 (t, 1 H), 7.13 (d, 1H), 7.02 (m, 2 H), 6.70 (s, 1H) 4.15 (t, 2 H), 3.92 (d, 6 H), 3.57 (t, 2 H), 2.64 (s, 3 H), 2.43 (s, 3 H), LCMS: 404.3 [M + H], HPLC purity: 99.88% |
| 86 | $^1$H-NMR (MeOH, 300 MHz): δ 7.43 (dd, 2 H), 7.35 (d, 2 H), 7.52 (d, 1 H), 7.10 (dd, 1 H), 7.04 (d, 1H), 5.96 (s, 1H) 4.64 (s, 2 H), 3.89 (d, 6 H), 2.51 (s, 3 H), 2.39 (s, 3 H), 1.30 (s, 9 H), LCMS: 445.4 [M + H], HPLC purity: 99.03% |
| 87 | $^1$H-NMR (MeOH, 300 MHz): δ 8.60 (d, 1 H), 7.30 (d, 1 H), 7.24 (d, 1 H), 7.10 (dd, 1 H), 7.02 (d, 1H), 5.91 (s, 1H) 4.74 (s, 2 H), 3.87 (d, 6 H), 2.71 (s, 1 H), 2.51 (s, 3 H), 2.37 (s, 3 H), LCMS: 405.4 [M + H], HPLC purity: 98.34% |
| 88 | $^1$H-NMR (MeOH, 300 MHz): δ 7.24 (m, 2 H), 7.09 (d, 1 H), 7.04 (d, 1 H), 6.95 (m, 2 H), 5.96 (s, 1H) 3.89 (d, 6 H), 3.73 (t, 2 H), 3.26 (t, 2 H), 2.49 (s, 3 H), 2.41 (s, 3 H), LCMS: 409.3 [M + H], HPLC purity: 98.81% |
| 89 | $^1$H-NMR (MeOH, 300 MHz): δ 8.80 (d, 2 H), 8.10 (d, 2 H), 7.11 (d, 1 H), 6.97 (m, 2 H), 6.60 (s, 1H) 4.07 (t, 2 H), 3.87 (d, 6 H), 3.43 (t, 2 H), 2.59 (s, 3 H), 2.41 (s, 3 H), LCMS: 404.4 [M + H], HPLC purity: 99.23% |
| 90 | $^1$H-NMR (MeOH, 300 MHz): δ 10.69 (s, 1 H), 9.00 (s, 1 H), 8.45 (dd, 1 H), 8.31 (d, 1 H), 7.77 (s, 1 H), 7.40 (d, 1 H), 7.25 (dd, 1H), 7.06 (d, 1H), 3.81 (d, 6 H), 2.67 (s, 3 H), 2.49 (s, 3 H), LCMS: 377.3 [M + H], HPLC purity: 99.91% |
| 91 | $^1$H-NMR (MeOH, 300 MHz): δ 7.27 (dd, 2 H), 7.22 (d, 1 H), 7.17 (dd, 2 H), 7.08 (dd, 1 H), 7.02 (d, 1H), 6.17 (s, 1H) 4.62 (m, 1 H), 3.49 (dd, 2 H), 3.10 (dd, 2 H), 2.46 (s, 3 H), 2.44 (s, 3 H), LCMS: 415.4 [M + H], HPLC purity: 99.94% |
| 92 | $^1$H-NMR (MeOH, 300 MHz): δ 8.49 (d, 1 H), 7.80 (dd, 1 H), 7.30 (d, 1 H), 7.25 (d, 1 H), 7.10 (dd, 1H), 7.05 (d, 1H), 5.99 (s, 1H) 4.70 (s, 2 H), 3.89 (d, 6 H), 2.53 (s, 3 H), 2.51 (s, 3 H), 2.39 (s, 3 H), LCMS: 404.3 [M + H], HPLC purity: 99.93% |
| 93 | $^1$H-NMR (MeOH, 300 MHz): δ 11.52 (s, 1 H), 7.69 (s, 1 H), 7.40 (d, 1 H), 7.23 (m, 2 H), 7.04 (d, 1H), 3.80 (d, 6 H), 2.54 (s, 3 H), 2.49 (s, 3 H), 2.38 (s, 3 H), LCMS: 396.3 [M + H], HPLC purity: 98.52% |
| 94 | $^1$H-NMR (MeOH, 400 MHz): δ 7.96 (dd, 2 H), 7.52 (d, 2 H), 7.20 (d, 1 H), 7.08 (dd, 1 H), 7.00 (d, 1H), 5.86 (s 1 H), 4.72 (s, 2 H), 3.85 (d, 6 H), 2.56 (s, 3 H), 2.49 (s, 3 H), 2.32 (s, 3 H), LCMS: 431.3 [M + H], HPLC purity: 99.66% |
| 95 | $^1$H-NMR (MeOH, 300 MHz): δ 8.60 (d, 1 H), 7.37 (s, 1 H), 7.32 (d, 1 H), 7.16 (d, 1 H), 7.07 (d, 1H), 6.61 (s 1 H), 3.91 (d, 6 H), 2.58 (s, 3 H), 2.55 (s, 3 H), LCMS: 366.4 [M + H], HPLC purity: 94.2% |
| 96 | $^1$H-NMR (MeOH, 300 MHz): δ 8.13 (d, 1 H), 7.92 (d, 1 H), 7.85 (d, 1 H), 7.56 (m, 3 H), 7.43 (d, 1 H), 7.24 (d, 1 H), 7.11 (dd, 1 H), 7.02 (d, 1 H), 6.01 (s, 1 H), 5.12 (s, 2 H), 3.86 (d, 6 H), 2.47 (s, 3 H), 2.36 (s, 3 H), LCMS: 439.5 [M + H], HPLC purity: 99.94% |
| 97 | $^1$H-NMR (DMSO, 400 MHz): δ 8.50 (t, 1 H), 7.78 (d, 2 H), 7.55 (d, 2 H), 7.38 (d, 1 H), 7.30 (s, 2 H), 7.22 (dd, 1H), 7.00 (d, 1H), 5.94 (s, 1 H), 5.12 (s, 2 H), 3.78 (d, 6 H), 2.54 (s, 3 H), 2.32 (s, 3 H), LCMS: 468.3 [M + H], HPLC purity: 98.74% |
| 98 | $^1$H-NMR (MeOD, 400 MHz): δ 8.16 (dd, 2 H), 7.19 (dd, 2 H), 7.24 (d, 1 H), 7.10 (d, 1 H), 7.02 (d, 1H), 5.72 (s, 1H), 4.99 (q, 1H), 3.87 (s, 6 H), 2.66 (s, 1 H), 2.50 (s, 3 H), 2.32 (s, 3 H), LCMS: 404.5 [M + H], HPLC purity: 97.3% |
| 99 | $^1$H-NMR (DMSO, 400 MHz): δ 8.55 (t, 1 H), 7.77 (d, 1 H), 7.70 (d, 1 H), 7.46 (dd, 2 H), 7.16 (dd, 2 H), 6.97 (d, 1H), 6.08 (s, 1H), 4.58 (d, 1 H), 3.82 (s, 3 H), 3.75 (s, 3 H), 2.39 (s, 3 H), LCMS: 393.4 [M + H], HPLC purity: 99.61% |
| 100 | $^1$H-NMR (DMSO, 400 MHz): δ 8.62 (t, 1 H), 8.58 (s, 1 H), 8.51 (dd, 2 H), 7.78 (d, 1 H), 7.72 (dd, 1 H), 7.36 (d, 2 H), 6.97 (d, 1H), 6.02 (s, 1H), 4.65 (d, 2 H), 3.82 (s, 3 H), 3.75 (s, 3 H), 2.38 (s, 3 H), LCMS: 376.4 [M + H], HPLC purity: 96.46% |
| 101 | $^1$H-NMR (DMSO, 400 MHz): δ 8.69 (t, 1 H), 8.58 (s, 1 H), 8.03 (s, 1 H), 7.84 (d, 1 H), 7.78 (t, 2 H), 7.71 (dd, 1 H), 7.64 (t, 1H), 6.98 (d, 1 H), 6.14 (s, 1H), 4.73 (d, 2 H), 3.83 (s, 3 H), 3.76 (s, 3 H), 3.21 (s, 3 H), 2.41 (s, 3 H), LCMS: 453.3 [M + H], HPLC purity: 98.50% |
| 102 | $^1$H-NMR (MeOD, 300 MHz): δ 7.43 (q, 2 H), 7.09 (m, 3 H), 7.00 (dd, 1 H), 6.89 (d, 1 H), 5.95 (t, 3 H), 4.64 (s, 2 H), 2.47 (s, 3 H), 2.36 (s, 3 H), LCMS: 391.6 [M + H], HPLC purity: 99.74% |
| 103 | $^1$H-NMR (MeOD, 300 MHz): δ 7.87 (d, 1 H), 7.59 (m, 2 H), 7.43 (dd, 2 H), 7.08 (t, 2 H), 5.99 (s, 1 H), 4.64 (s, 2 H), 2.54 (s, 3 H), 2.40 (s, 3 H), LCMS: 415.4 [M + H], HPLC purity: 99.90% |
| 104 | $^1$H-NMR (MeOD, 300 MHz): δ 7.89 (d, 2 H), 7.72 (d, 2 H), 7.46 (m, 2 H), 7.11 (m, 2 H), 6.01 (s, 1 H), 4.67 (s, 2 H), 2.59 (s, 3 H), 2.41 (s, 3 H), LCMS: 415.1 [M + H], HPLC purity: 99.92% |
| 105 | $^1$H-NMR (MeOD, 300 MHz): δ 7.45 (t, 2 H), 7.11 (d, 2 H), 6.91 (s, 2 H), 5.97 (s, 1 H), 4.67 (s, 2 H), 3.90 (s, 6 H), 3.82 (s, 3 H), 2.56 (s, 3 H), 2.39 (s, 3 H), LCMS: 437.2 [M + H], HPLC purity: 99.63% |
| 106 | $^1$H-NMR (MeOD, 300 MHz): δ 7.60 (m, 1 H), 7.43 (m, 3 H), 7.31 (m, 1 H), 7.09 (m, 2 H), 5.98 (s, 1 H), 4.65 (s, 2 H), 2.54 (s, 3 H), 2.40 (s, 3 H), LCMS: 383.5 [M + H], HPLC purity: 99.88% |
| 107 | $^1$H-NMR (MeOD, 300 MHz): δ 8.09 (d, 2 H), 7.84 (d, 2 H), 7.45 (dd, 2 H), 7.10 (t, 2 H), 6.01 (s, 1 H), 4.67 (s, 2 H), 3.93 (s, 3 H), 2,59 (s, 3H), 2.42 (s, 3 H), LCMS: 404.45 [M + H], HPLC purity: 99.62% |
| 108 | $^1$H-NMR (MeOH, 300 MHz): δ 7.42 (d, 1 H), 7.34 (m, 3 H), 7.18 (m, 3 H), 5.95 (s, 1 H), 4.62 (s, 2 H), 3.92 (s, 3 H), 2.51 (s, 3 H), 2.39 (s, 3 H), 2.34 (s, 3 H), LCMS: 391.5 [M + H], HPLC purity: 98.09% |

TABLE 3-continued

| Ex. | Analytical Data |
|---|---|
| 109 | $^1$H-NMR (MeOD, 300 MHz): δ 8.43 (t, 1 H), 7.44 (m, 2 H), 7.38 (s, 1 H), 7.16 (m, 3 H), 6.99 (d, 1 H), 6.00 (s, 1 H), 4.57 (d, 2 H), 4.04 (m, 4 H), 2.51 (s, 3 H), 2.32 (s, 3 H), 1.35 (q, 6 H), LCMS: 435.3 [M + H], HPLC purity: 99.75% |
| 110 | $^1$H-NMR (DMSO, 400 MHz): δ 8.82 (bs, 2 H), 8.33 (bs, 1 H), 7.28 (d, 2 H), 7.14 (t, 3 H), 6.92 (dd, 1 H), 6.77 (d, 1 H), 5.91 (s, 1 H), 4.53 (s, 2 H), 2.48 (s, 3 H), 2.30 (s, 3 H), 2.26 (s, 3 H), LCMS: 375.3 [M + H], HPLC purity: 99.70% |
| 111 | $^1$H-NMR (MeOH, 400 MHz): δ 7.40 (s, 1 H), 7.35 (t, 2 H), 7.07. (dd, 1 H), 6.99 (t, 2H), 6.92 (d, 1 H), 5.81 (s, 1 H), 4.55 (s, 2 H), 3.78 (d, 6 H), 2.81 (m, 1 H), 2.45 (s, 3 H), 1.13 (d, 6 H), LCMS: 435.5 [M + H], HPLC purity: 95.7% |
| 112 | $^1$H-NMR (MeOD, 400 MHz): δ 8.88 (d, 2 H), 7.57 (d, 2 H), 7.49 (m, 2 H), 7.13 (t, 2 H), 6.65 (s, 1 H), 4.86 (s, 2 H), 2.71 (s, 3 H), 2.67 (s, 3 H), LCMS: 412.4 [M + H], HPLC purity: 99.49% |

Biological Assays
In Vitro Assay in Mammalian Cell Culture

The antiviral activity of compounds of the invention has been evaluated based on the ability of the compounds to prevent virus from causing viral cytopathic effects (CPE) in mammalian cell culture. Incubation time, cell line, cell density and virus titer differed from assay to assay but the general procedure was as follows: Cells were cultivated on 96 well flat bottom plates to approximately 90% confluence (20 000-90 000 cells/well) in a suitable media. The titer of the virus was determined by the standard method of tissue culture infective dose (TCID$_{50}$) on cells. Briefly, cells were infected with 50 µl of virus suspension, and diluted 10-fold in media. The plates were incubated in 37° C. with 5% CO$_2$ for 3-7 days and cells were inspected daily for CPE. After determining CPE, plates were stained with Gram's Crystal Violet solution and optical density was read at 540 nm. The highest virus dilution that resulted in >95% CPE was used in the assays. Substances at a final concentration of 2.5-20 µM and the virus were added to the cells and incubated for 3-7 days depending on the virus and cell line used. As controls, uninfected cells and cells infected with virus (no substance) were included on each plate. The cells were stained with crystal violet after determining the CPE on infected controls and the optical density was read at 540 nm. The inhibition capacity was calculated as a % by comparison with non-infected and infected controls.

Table 4 shows the inhibition capacity of compounds of the invention on different picornaviruses at different concentrations. LV012: Ljungan virus strain 012; LV145: Ljungan virus strain 145; EMCV: encephalomyocarditis virus; HPeV-1: Human parechovirus strain 1; HPeV-2: Human parechovirus strain 2; PTV: Porcine Tescho virus; EV6: Enterovirus strain 6; EV30: Enterovirus strain 30; EV71: Enterovirus strain 71; Cox-B1: coxsackie B virus strain 1; Cox-B2: coxsackie B virus strain 2; Cox-B3: coxsackie B virus strain 3; Cox-B4: coxsackie B virus strain 4; Cox-B5: coxsackie B virus strain 5; Polio 1: polio virus strain 1.

TABLE 4

| Ex. | Virus | Conc. µM | % inh. |
|---|---|---|---|
| 1 | EV6 | 0.25 | 75 |
| 2 | EV30 | 0.25 | 85 |
| 3 | EMCV | 2.5 | 92 |
| 4 | EV71 | 2.5 | 46 |
| 5 | Cox-B4 | 0.25 | 71 |
| 6 | LV145 | 5.0 | 56 |
| 7 | LV145 | 2.5 | 54 |
| 8 | Cox-B5 | 0.25 | 100 |
| 9 | EV71 | 0.25 | 93 |
| 10 | LV145 | 2.5 | 69 |
| 11 | PTV | 2.5 | 57 |
| 12 | LV012 | 2.5 | 60 |
| 13 | EV71 | 1 | 66 |
| 14 | Polio-1 | 10.0 | 73 |
| 15 | Polio-1 | 10.0 | 75 |
| 16 | LV145 | 10.0 | 83 |
| 17 | LV145 | 10.0 | 75 |
| 18 | Polio-1 | 10.0 | 51 |
| 19 | LV145 | 10.0 | 34 |
| 20 | EV71 | 1.0 | 40 |
| 21 | Polio-1 | 10.0 | 78 |
| 22 | Cox-B2 | 10.0 | 44 |
| 23 | Polio-1 | 10.0 | 94 |
| 24 | Polio-1 | 10.0 | 86 |
| 25 | HPeV-1 | 10.0 | 24 |
| 26 | Cox-B2 | 10.0 | 30 |
| 27 | Polio-1 | 10.0 | 35 |
| 28 | Polio-1 | 10.0 | 72 |
| 29 | Cox-B2 | 10.0 | 62 |
| 30 | LV145 | 10.0 | 100 |
| 31 | LV145 | 10.0 | 14 |
| 32 | Polio-1 | 10.0 | 25 |
| 33 | EV30 | 1.0 | 48 |
| 34 | EV71 | 1.0 | 100 |
| 35 | EV30 | 0.1 | 88 |
| 36 | Cox-B5 | 1.0 | 97 |
| 37 | Cox-B2 | 10.0 | 78 |
| 38 | LV0145 | 10.0 | 84 |
| 39 | Polio-1 | 1.0 | 71 |
| 40 | EV71 | 0.01 | 100 |
| 41 | EMCV | 10.0 | 93 |
| 42 | Polio-1 | 1.0 | 96 |
| 43 | HPeV-1 | 10.0 | 46 |
| 44 | Polio-1 | 1.0 | 70 |
| 45 | EV71 | 1.0 | 100 |
| 46 | LV0145 | 10.0 | 92 |
| 47 | HPeV-1 | 10.0 | 56 |
| 48 | Polio-1 | 1.0 | 79 |
| 49 | Cox-B2 | 1.0 | 80 |
| 50 | Polio-1 | 1.0 | 81 |
| 51 | LV0145 | 10.0 | 94 |
| 52 | LV0145 | 10.0 | 63 |
| 53 | Polio-1 | 10.0 | 84 |
| 54 | Polio-1 | 1.0 | 89 |
| 55 | LV145 | 1.0 | 41 |
| 56 | LV145 | 1.0 | 61 |
| 57 | HPeV-1 | 10.0 | 22 |
| 58 | Polio-1 | 0.1 | 74 |
| 59 | Cox-B2 | 10.0 | 88 |
| 60 | EV-71 | 1.0 | 69 |
| 61 | LV0145 | 10.0 | 85 |
| 62 | Polio-1 | 1.0 | 97 |
| 63 | Polio-1 | 1.0 | 87 |
| 64 | Polio-1 | 1.0 | 20 |
| 65 | Cox-B2 | 1.0 | 91 |
| 66 | Polio-1 | 0.01 | 100 |
| 67 | Polio-1 | 1.0 | 63 |
| 68 | LV145 | 10.0 | 86 |

TABLE 4-continued

| Ex. | Virus | Conc. μM | % inh. |
|---|---|---|---|
| 69 | Cox-B2 | 10.0 | 65 |
| 70 | Polio-1 | 10.0 | 89 |
| 71 | Polio-1 | 10.0 | 72 |
| 72 | Cox-B4 | 0.1 | 85 |
| 73 | Cox-B4 | 0.1 | 44 |
| 74 | LV012 | 10 | 55 |
| 75 | Cox-B3 | 0.01 | 85 |
| 76 | Cox-B3 | 1 | 100 |
| 77 | Cox-B3 | 0.1 | 60 |
| 78 | Cox-B1 | 0.1 | 94 |
| 79 | EV68 | 1 | 51 |
| 80 | EV6 | 1 | 93 |
| 81 | Cox-B1 | 0.01 | 76 |
| 82 | Cox-B3 | 0.01 | 82 |
| 83 | EV71 | 0.01 | 82 |
| 84 | Cox-B3 | 0.1 | 84 |
| 85 | Cox-B1 | 1 | 98 |
| 86 | LV012 | 10 | 48 |
| 87 | Polio-1 | 0.1 | 100 |
| 88 | EV30 | 1 | 88 |
| 89 | Cox-2 | 1 | 100 |
| 90 | LV012 | 10 | 71 |
| 91 | Cox-B5 | 1 | 75 |
| 92 | Cox-B3 | 0.01 | 100 |
| 93 | LV012 | 100 | 42 |
| 94 | Cox-B1 | 0.01 | 100 |
| 95 | HPeV-1 | 10 | 55 |
| 96 | Cox-B1 | 0.1 | 100 |
| 97 | EV71 | 0.1 | 94 |
| 98 | Not tested | — | — |
| 99 | Cox-B3 | 0.1 | 100 |
| 100 | EV30 | 0.1 | 78 |
| 101 | EV71 | 0.1 | 99 |
| 102 | Cox-B3 | 1 | 100 |
| 103 | EMCV | 10 | 74 |
| 104 | Theiler | 10 | 59 |
| 105 | EV30 | 10 | 67 |
| 106 | LV145 | 10 | 100 |
| 107 | Polio | 1 | 21 |
| 108 | Cox-B1 | 1 | 100 |
| 109 | Polio-1 | 1 | 88 |
| 110 | Cox-B5 | 1 | 72 |
| 111 | Cox-B1 | 0.1 | 68 |

Table 5 and 6 show the antiviral effect of certain compounds of the invention at different concentrations against a panel of different picornaviruses. LV012: Ljungan virus strain 012; LV145: Ljungan virus strain 145; EMCV: encephalomyocarditis virus; HPeV-1: Human parechovirus strain 1; HPeV-2: Human parechovirus strain 2; PTV: Porcine Tescho virus; EV6: Enterovirus strain 6; EV30: Enterovirus strain 30; EV71: Enterovirus strain 71; B1: coxsackie B virus strain 1; B2: coxsackie B virus strain 2; B3: coxsackie B virus strain 3; B4: coxsackie B virus strain 4; B5: coxsackie B virus strain 5; Polio 1: polio virus strain 1.

TABLE 5

| Ex. | Conc. mM | LV012 | LV145 | EMCV | HPeV-1 | PTV | EV6 | EV30 |
|---|---|---|---|---|---|---|---|---|
| 1 | 5 | 34 | 37 | 14 | 14 | 19 | 90 | 100 |
| 2 | 5 | 49 | 17 | 0 | 0 | 33 | 83 | 91 |
| 4 | 10 | 28 | 61 | 81 | 7 | 87 | 0 | 0 |
| 5 | 5 | 18 | 60 | 0 | 22 | 11 | 80 | 58 |
| 6 | 10 | 28 | 63 | 0 | 60 | 62 | 58 | 44 |
| 7 | 2.5 | 14 | 54 | 0 | 6 | 29 | 78 | 89 |
| 8 | 5 | 38 | 28 | 0 | 14 | 22 | 88 | 53 |
| 9 | 10 | 18 | 59 | 14 | 19 | 23 | 66 | 35 |
| 10 | 10 | 0 | 41 | 25 | 3 | 43 | 93 | 88 |
| 11 | 10 | 18 | 77 | 0 | 8 | 51 | 70 | 80 |
| 12 | 2.5 | 60 | nd | 0 | 8 | 0 | 63 | 84 |
| 33 | 10 | nd | 69 | 60 | 13 | nd | nd | 85 |
| 72 | 1 | 0 | 7 | 0 | 4 | nd | 77 | 100 |
| 75 | 0.1 | 0 | 0 | 0 | 0 | nd | 90 | 100 |
| 79 | 0.1 | 0 | 0 | 0 | 0 | nd | 0 | 10 |
| 80 | 1 | 0 | 0 | 0 | 0 | nd | 80 | 90 |
| 81 | 0.1 | 0 | 0 | 0 | 0 | nd | 62 | 97 |
| 82 | 0.1 | 0 | 0 | 0 | nd | nd | 89 | 94 |
| 92 | 0.1 | 0 | 0 | 0 | nd | nd | nd | 100 |
| 94 | 0.1 | 12 | 0 | 0 | nd | nd | nd | 96 |
| 100 | 0.1 | 0 | 0 | 0 | nd | nd | 88 | 78 |
| 101 | 0.1 | 0 | 0 | 0 | nd | nd | 44 | 89 |
| 111 | 1 | 0 | 0 | 0 | nd | nd | 89 | 80 |

TABLE 6

| Ex. | Conc. mM | EV68 | EV71 | B1 | B2 | B3 | B4 | B5 | Polio 1 |
|---|---|---|---|---|---|---|---|---|---|
| 1 | 5 | nd | 44 | 93 | 60 | 95 | 86 | 90 | 31 |
| 2 | 5 | nd | 73 | 91 | 93 | 97 | 86 | 91 | 90 |
| 4 | 10 | nd | 69 | 36 | 0 | 0 | 53 | 0 | 17 |
| 5 | 5 | nd | 77 | 79 | 76 | nd | 97 | 94 | 68 |
| 6 | 10 | nd | 37 | 35 | 82 | nd | 69 | 54 | 19 |
| 7 | 2.5 | nd | 82 | 77 | 92 | nd | 82 | 68 | 80 |
| 8 | 5 | nd |  | 82 | 100 | nd | 89 | 100 | 91 |
| 9 | 10 | nd | 16 | 53 | 76 | nd | 48 | 73 | 91 |
| 10 | 10 | nd | 58 | 79 | 97 | nd | 94 | 92 | 94 |
| 11 | 10 | nd | 47 | 93 | 85 | nd | 100 | 70 | 52 |
| 12 | 2.5 | nd | 80 | 93 | nd | nd | 77 | 82 | 73 |
| 33 | 10 | nd | 0 | nd | 81 | nd | nd | 92 | 58 |
| 72 | 1 | nd | 84 | 100 | 94 | 99 | 91 | 99 | 100 |
| 75 | 0.1 | 31 | 85 | 100 | 100 | 89 | 100 | 98 | 100 |
| 79 | 0.1 | 46 | 88 | 88 | 84 | 87 | 78 | 98 | 79 |
| 80 | 1 | 30 | 78 | 78 | 96 | 78 | 78 | 97 | 85 |
| 81 | 0.1 | 29 | 86 | 85 | 88 | 87 | 77 | 81 | 89 |
| 82 | 0.1 | 24 | 85 | 95 | 98 | 91 | 100 | 89 | 100 |
| 92 | 0.1 | nd | 100 | 100 | 96 | 100 | nd | 95 | 98 |
| 94 | 0.1 | nd | 100 | 100 | 100 | 100 | nd | 56 | 100 |
| 100 | 0.1 | nd | 81 | nd | 99 | 199 | nd | 90 | 83 |
| 101 | 0.1 | nd | 99 | nd | 99 | 90 | nd | 29 | 100 |
| 111 | 1 | 40 | 96 | 97 | 96 | 100 | 98 | 99 | 100 |

Evaluation of Anti-Viral Efficacy Against Coxsackie Virus in a Neutropenic Mouse Model Test System Male BALB/c mice, weighing 22-26 grams were used with 4 animals/group.

Neutropenic induction: Cyclophosphamide

Challenge organism: Coxsackie (human origin) virus CVB3

Route of infection: Intraperitoneal

Route of administration: per oral

End point: Cumulative survival

All experimental procedures involving animals were performed according to protocols approved by the Institutional Animal Ethics Committee of Anthem Biosciences. The mice, male BALB/c mice were housed 4 animals per cage and allowed access to feed and water ad libitum under controlled conditions. Mice were acclimatized for 7 days prior to the study. The animals were observed daily for general health during this period.

Neutropenic Induction 4 mice/group were treated with intraperitoneal injection of cyclophosphamide (150 mg/kg), 2 days before and, on day "0" 4 hours before infection in order to become neutropenic.

Infection and Treatment

Animals were infected by intraperitoneal injection of 0.2 mL of saline containing $10^3$ PFU of Coxsackie B3 virus, Nancy strain on day 0. The animals were then treated with the compound of Ex. 9, 200 mg/kg once daily per orally starting on day 1 (group 1) or on day 3 (group 2). The control group was treated with vehicle only (0.4% Tween 80, 2% glycerol and 15% 3-hydroxypropyl cyclodextrin)

Clinical Observation

The animals were observed daily during the study period for signs of mortality, morbidity (paralysis) and signs of acute toxicity. Abnormal clinical signs were recorded if observed.

Results

The results of the above described assay indicate that the compound of Ex. 9 has an antiviral effect in vivo and can extend the life of the animals, cf. the FIGURE.

Toxicity Assay

Mouse

Treatment with Ex 9 at 200 and 400 mg/kg body weight/day for 7 days in BALB/C mice did not reveal any adverse clinical signs or mortality in neither sex. The treatment resulted in no adverse effects on body weight, feed consumption, hematology, clinical chemistry and histopathology of the major organs evaluated.

In light of above findings from the present study, the No Observed Adverse Effect Level (NOAEL) of Ex 9 could be determined as 400 mg/kg body weight/day when administered orally to BALB/c mice for 7 consecutive days under the tested dose levels and experimental conditions employed.

Rat

MTD Study

Single dose treatment with Ex 9 in doses up to 2000 mg/kg resulted in no adverse effects on clinical signs, mortality, body weight, body weight gain, feed consumption, absolute and relative organ weights. On macroscopic examination, no treatment related gross pathological findings were observed.

In the light of the above findings, the maximum tolerable dose of Ex 9 in female Sprague Dawley rats is found to be >2000 mg/kg body weight under the experimental conditions employed.

7 Days Toxicity Study

Treatment with test item Ex 9 at 250 and 750 mg/kg body weight/day for 7 days in Sprague Dawley rats did reveal adverse clinical signs in both sexes at 750 mg/kg and mortality in one female at 750 mg/kg. The treatment resulted in adverse effects on body weight, feed consumption, hematology, clinical chemistry and histopathology of the major organs evaluated at the 759 mg/kg dose level.

In light of above findings from the present study, the No Observed Adverse Effect Level (NOAEL) of Ex 9 could be determined as 250 mg/kg body weight/day when administered orally to Sprague Dawley rats for 7 consecutive days under the tested dose levels and experimental conditions employed.

28 Days Toxicity Study

Treatment with the test item Ex 9 at 100 and 200 mg/kg body weight for 28 days in both sexes had no adverse effects on clinical signs, body weight, feed consumption, hematology, clinical chemistry, urinalysis, neurological examination, gross necropsy and histopathological evaluation of the specified tissues. All the animals survived until the scheduled terminal necropsy on Day 29. Serum biochemistry showed an increase in cholesterol, which was correlated with findings of macrovesicular fatty changes in liver at 200 mg/kg body weight in both the sexes.

In light of above findings from the present study, the No Observed Adverse Effect Level (NOAEL) of Ex 9 could be determined as 200 mg/kg body weight when administered orally to Sprague Dawley rats for 28 consecutive days under the tested dose levels and experimental conditions employed.

The invention claimed is:

1. A pharmaceutical composition comprising a compound of formula (I)

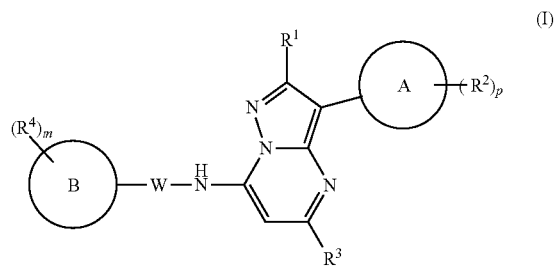

or a pharmaceutically acceptable salt thereof, wherein

W is

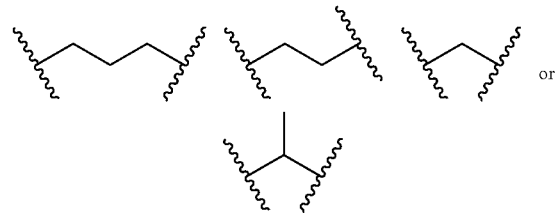

p is an integer of from 0 to 3;

$R^1$ is H or C1-C6 alkyl;

ring A is phenyl or 5- or 6-membered heteroaryl;

when ring A is phenyl, said phenyl is not substituted in ortho position;

each $R^2$ is independently selected from C1-C6 alkyl, $R^5O-$, $R^6R^7NC(O)-$, $R^9C(O)N(R^8)-$, $R^{10}OC(O)-$, $R^{11}C(O)O-$, and halogen;

$R^5$, $R^6$, $R^7$ and $R^8$ are independently selected from H and C1-C6 alkyl;

$R^9$, $R^{10}$ and $R^{11}$ are independently selected from C1-6 alkyl;

any alkyl is optionally substituted by one or more F; or two $R^2$ attached to adjacent carbon atoms together form a methylenedioxy or ethylenedioxy biradical;

$R^3$ is C1-C6 alkyl;

m is an integer of from 0 to 2;

each $R^4$ is independently selected from C1-C6 alkyl, $R^{12}O$, halogen, $R^{13}R^{14}NC(O)-$, $R^{16}C(O)N(R^{15})-$, $R^{17}OC(O)-$, $R^{18}C(O)O-$, $R^{19}S(O)_2-$, $R^{20}S(O)_2N(H)-$, $NH_2S(O)_2-$, $R^{21}C(O)-$, $N(R^{22})(R^{23})-$, and $^-O-$;

$R^{12}$, $R^{13}$, $R^{14}$, $R^{15}$, $R^{22}$, and $R^{23}$ are independently selected from H and C1-C6 alkyl;

$R^{16}$, $R^{17}$, $R^{18}$, $R^{19}$, $R^{20}$, and $R^{21}$ are independently selected from C1-6 alkyl;

any alkyl is optionally substituted by one or more F; or two $R^4$ attached to adjacent atoms of ring B form, together with the atoms to which they are attached, a 5- or 6-membered heterocyclic or carbocyclic ring, or a benzene ring;

ring B is a 5- or 6-membered saturated or unsaturated carbocyclyl, 5- or 6-membered heteroaryl or phenyl;

and optionally a pharmaceutically acceptable excipient, provided that the compound is not:
N-(cyclohexylmethyl)-2,5-dimethyl-3-(p-tolyl)pyrazolo[1,5-a]pyrimidin-7-amine, N-benzyl-2,5-dimethyl-3-(p-tolyl)pyrazolo[1,5-a]pyrimidin-7-amine, or 2,5-dimethyl-N-phenethyl-3-(p-tolyl)pyrazolo[1,5-a]pyrimidin-7-amine.

2. The composition according to claim 1, wherein ring B is phenyl.
3. The composition according to claim 1, wherein ring B is 5- or 6-membered heteroaryl.
4. The composition according to claim 1, wherein ring A is phenyl.
5. The composition according to claim 1, wherein $R^1$ is C1-C6 alkyl.
6. The composition according to claim 1, wherein the compound is selected from
  N-[(4-chlorophenyl)methyl]-3-(3,4-dimethoxyphenyl)-2,5-dimethyl-pyrazolo[1,5-a]pyrimidin-7-amine,
  3-(3,4-dimethoxyphenyl)-N-[(4-methoxyphenyl)methyl]-2,5-dimethyl-pyrazolo[1,5-a]pyrimidin-7-amine,
  3-(4-fluorophenyl)-2,5-dimethyl-N-(1-phenylethyl)pyrazolo[1,5-a]pyrimidin-7-amine,
  N-benzyl-5-isopropyl-3-phenyl-pyrazolo[1,5-a]pyrimidin-7-amine,
  N-[2-(4-chlorophenyl)ethyl]-3-(3,4-dimethoxyphenyl)-2,5-dimethyl-pyrazolo[1,5-a]pyrimidin-7-amine,
  3-(3,4-dimethoxyphenyl)-2,5-dimethyl-N-(p-tolylmethyl)pyrazolo[1,5-a]pyrimidin-7-amine,
  3-(3,4-dimethoxyphenyl)-2,5-dimethyl-N-(3-phenylpropyl)pyrazolo[1,5-a]pyrimidin-7-amine,
  N-(1,3-benzodioxol-5-ylmethyl)-3-(3,4-dimethoxyphenyl)-2,5-dimethyl-pyrazolo[1,5-a]pyrimidin-7-amine,
  3-(3,4-dimethoxyphenyl)-N-[(4-fluorophenyl)methyl]-2,5-dimethyl-pyrazolo[1,5-a]pyrimidin-7-amine,
  3-(3,4-dimethoxyphenyl)-2,5-dimethyl-N-(2-phenylpropyl)pyrazolo[1,5-a]pyrimidin-7-amine,
  N-(2-cyclohexen-1-ylethyl)-3-(3,4-dimethoxyphenyl)-2,5-dimethyl-pyrazolo[1,5-a]pyrimidin-7-amine,
  3-(3,4-dimethoxyphenyl)-N-[2-(2,4-dimethoxyphenyl)ethyl]-2,5-dimethyl-pyrazolo[1,5-a]pyrimidin-7-amine,
  N-benzyl-3-(4-fluorophenyl)-2,5-dimethyl-pyrazolo[1,5-a]pyrimidin-7-amine,
  3-(4-fluorophenyl)-2,5-dimethyl-N-phenethyl-pyrazolo[1,5-a]pyrimidin-7-amine,
  N-[2-(3,4-dimethoxyphenyl) ethyl]-3-(4-fluorophenyl)-2,5-dimethyl-pyrazolo[1,5-a]pyrimidin-7-amine,
  N-(2-cyclohexen-1-ylethyl)-3-(4-fluorophenyl)-2,5-dimethyl-pyrazolo[1,5-a]pyrimidin-7-amine,
  3-(4-fluorophenyl)-2,5-dimethyl-N-(1-phenylethyl)pyrazolo[1,5-a]pyrimidin-7-amine,
  N-benzyl-3-(4-fluorophenyl)-5-methyl-pyrazolo[1,5-a]pyrimidin-7-amine,
  N-[2-(3,4-dimethoxyphenyl)ethyl]-3-(4-fluorophenyl)-5-methyl-pyrazolo[1,5-a]pyrimidin-7-amine,
  5-tert-butyl-N-(2-cyclohexen-1-ylethyl)-3-(4-fluorophenyl)-2-methyl-pyrazolo[1,5-a]pyrimidin-7-amine,
  N-benzyl-5-methyl-3-phenyl-pyrazolo[1,5-a]pyrimidin-7-amine,
  N-[2-(3,4-dimethoxyphenyl)ethyl]-5-methyl-3-phenyl-pyrazolo[1,5-a]pyrimidin-7-amine,
  5-tert-butyl-N-(3-imidazol-1-ylpropyl)-3-phenyl-pyrazolo[1,5-a]pyrimidin-7-amine,
  N-(3-imidazol-1-ylpropyl)-2-methyl-3-phenyl-5-propyl-pyrazolo[1,5-a]pyrimidin-7-amine,
  N-benzyl-3-(4-chlorophenyl)-5-methyl-pyrazolo[1,5-a]pyrimidin-7-amine,
  3-(4-chlorophenyl)-5-methyl-N-phenethyl-pyrazolo[1,5-a]pyrimidin-7-amine,
  3-(4-chlorophenyl)-N-[2-(3,4-dimethoxyphenyl)ethyl]-5-methyl-pyrazolo[1,5-a]pyrimidin-7-amine,
  3-(4-chlorophenyl)-N-(3-imidazol-1-ylpropyl)-5-methyl-pyrazolo[1,5-a]pyrimidin-7-amine,
  N-[2-(3,4-dimethoxy phenyl)ethyl]-5-methyl-3-(p-tolyl)pyrazolo[1,5-a]pyrimidin-7-amine,
  N-[2-(3,4-dimethoxyphenyl) ethyl]-2-ethyl-5-methyl-3-phenyl-pyrazolo[1,5-a]pyrimidin-7-amine,
  2-ethyl-N-(3-imidazol-1-ylpropyl)-5-methyl-3-phenyl-pyrazolo[1,5-a]pyrimidin-7-amine,
  3-(4-chlorophenyl)-2,5-dimethyl-N-[2-(p-tolyl)ethyl]pyrazolo[1,5-a]pyrimidin-7-amine,
  2,5-dimethyl-3-(p-tolyl)-N-(2-pyridylmethyl)pyrazolo[1,5-a]pyrimidin-7-amine,
  2,5-dimethyl-3-(p-tolyl)-N-(3-pyridylmethyl)pyrazolo[1,5-a]pyrimidin-7-amine,
  3-(3,4-dimethoxyphenyl)-2,5-dimethyl-N-(2-pyridylmethyl)pyrazolo[1,5-a]pyrimidin-7-amine,
  3-(4-fluorophenyl)-2,5-dimethyl-N-(3-pyridylmethyl)pyrazolo[1,5-a]pyrimidin-7-amine,
  3-(4-fluorophenyl)-2,5-dimethyl-N-(2-pyridylmethyl)pyrazolo[1,5-a]pyrimidin-7-amine,
  2,5-dimethyl-3-phenyl-N-(3-pyridylmethyl)pyrazolo[1,5-a]pyrimidin-7-amine,
  N-benzyl-3-(3,4-dimethoxyphenyl)-2,5-dimethyl-pyrazolo[1,5-a]pyrimidin-7-amine,
  3-(4-chlorophenyl)-2,5-dimethyl-N-(2-pyridylmethyl)pyrazolo[1,5-a]pyrimidin-7-amine,
  3-(4-chlorophenyl)-N-(3-imidazol-1-ylpropyl)-2,5-dimethyl-pyrazolo[1,5-a]pyrimidin-7-amine,
  3-(4-chlorophenyl)-2,5-dimethyl-N-(3-pyridylmethyl)pyrazolo[1,5-a]pyrimidin-7-amine,
  3-(4-methoxyphenyl)-2,5-dimethyl-N-(3-pyridylmethyl)pyrazolo[1,5-a]pyrimidin-7-amine,
  3-(4-methoxyphenyl)-2,5-dimethyl-N-(4-pyridylmethyl)pyrazolo[1,5-a]pyrimidin-7-amine,
  N-(3-imidazol-1-ylpropyl)-3-(4-methoxyphenyl)-2,5-dimethyl-pyrazolo[1,5-a]pyrimidin-7-amine,
  3-(4-methoxyphenyl)-2,5-dimethyl-N-[2-(2-pyridyl)ethyl]pyrazolo[1,5-a]pyrimidin-7-amine,
  2,5-dimethyl-N-(3-pyridylmethyl)-3-(2-thienyl)pyrazolo[1,5-a]pyrimidin-7-amine,
  2,5-dimethyl-N-(4-pyridylmethyl)-3-(2-thienyl)pyrazolo[1,5-a]pyrimidin-7-amine,
  N-(3-imidazol-1-ylpropyl)-2,5-dimethyl-3-(2-thienyl)pyrazolo[1,5-a]pyrimidin-7-amine,
  3-(3,4-dimethoxyphenyl)-2,5-dimethyl-N-[[4-(trifluoromethyl)phenyl]methyl]pyrazolo[1,5-a]pyrimidin-7-amine,
  3-(3,4-dimethoxyphenyl)-2,5-dimethyl-N-(4-pyridylmethyl)pyrazolo[1,5-a]pyrimidin-7-amine,
  3-(3,4-dimethoxyphenyl)-2,5-dimethyl-N-[[4-(trifluoromethoxy)phenyl]methyl]pyrazolo[1,5-a]pyrimidin-7-amine,
  N-[4-[[[3-(3,4-dimethoxyphenyl)-2,5-dimethyl-pyrazolo[1,5-a]pyrimidin-7-yl]amino]methyl]phenyl]acetamide,
  3-(3,4-dimethoxyphenyl)-N-[(4-dimethylaminophenyl)methyl]-2,5-dimethyl-pyrazolo[1,5-a]pyrimidin-7-amine,
  3-(3,4-dimethoxyphenyl)-N-[(6-methoxy-3-pyridyl)methyl]-2,5-dimethyl-pyrazolo[1,5-a]pyrimidin-7-amine, N-[4-[[[3-(3,4-dimethoxyphenyl)-2,5-dimethyl-pyrazolo[1,5-a]pyrimidin-7-yl]amino]methyl]phenyl]methanesulfonamide,
4-[[[3-(3,4-dimethoxyphenyl)-2,5-dimethyl-pyrazolo[1,5-a]pyrimidin-7-yl]amino]methyl]phenol,
3-(3,4-dimethoxyphenyl)-2,5-dimethyl-N-[(3-methylsulfonylphenyl)methyl]pyrazolo[1,5-a]pyrimidin-7-amine,
3-(3,4-dimethoxyphenyl)-2,5-dimethyl-N-[(1-oxidopyridin-1-ium-4-yl)methyl]pyrazolo[1,5-a]pyrimidin-7-amine,
3-(3,4-dimethoxyphenyl)-2,5-dimethyl-N-[(4-methylsulfonylphenyl)methyl]pyrazolo[1,5-a]pyrimidin-7-amine,
3-(3,4-dimethoxyphenyl)-2,5-dimethyl-N-[2-(2-pyridyl)ethyl]pyrazolo[1,5-a]pyrimidin-7-amine,
N-[(4-tert-butylphenyl)methyl]-3-(3,4-dimethoxyphenyl)-2,5-dimethyl-pyrazolo[1,5-a]pyrimidin-7-amine,
3-(3,4-dimethoxyphenyl)-2,5-dimethyl-N-[(2-methylpyrimidin-4-yl)methyl]pyrazolo[1,5-a]pyrimidin-7-amine,
3-(3,4-dimethoxyphenyl)-2,5-dimethyl-N-[2-(2-thienyl)ethyl]pyrazolo[1,5-a]pyrimidin-7-amine,
3-(3,4-dimethoxyphenyl)-2,5-dimethyl-N-[2-(4-pyridyl)ethyl]pyrazolo[1,5-a]pyrimidin-7-amine,
3-(3,4-dimethoxyphenyl)-2,5-dimethyl-N-[(6-methyl-3-pyridyl)methyl]pyrazolo[1,5-a]pyrimidin-7-amine,
1-[4-[[[3-(3,4-dimethoxyphenyl)-2,5-dimethyl-pyrazolo[1,5-a]pyrimidin-7-yl]amino]methyl]phenyl]ethanone,
3-(3,4-dimethoxyphenyl)-2,5-dimethyl-N-(1-naphthylmethyl)pyrazolo[1,5-a]pyrimidin-7-amine,
4-[[[3-(3,4-dimethoxyphenyl)-2,5-dimethyl-pyrazolo[1,5-a]pyrimidin-7-yl]amino]methyl]benzenesulfonamide,
3-(3,4-dimethoxyphenyl)-N-[(4-fluorophenyl)methyl]-5-methyl-pyrazolo[1,5-a]pyrimidin-7-amine,
3-(3,4-dimethoxyphenyl)-2,5-dimethyl-N-[1-(4-pyridyl)ethyl]pyrazolo[1,5-a]pyrimidin-7-amine,
3-(3,4-dimethoxyphenyl)-5-methyl-N-(4-pyridylmethyl)pyrazolo[1,5-a]pyrimidin-7-amine,
3-(3,4-dimethoxyphenyl)-5-methyl-N-[(3-methylsulfonylphenyl)methyl]pyrazolo[1,5-a]pyrimidin-7-amine,
3-(1,3-benzodioxol-5-yl)-N-[(4-fluorophenyl)methyl]-2,5-dimethyl-pyrazolo[1,5-a]pyrimidin-7-amine,
3-(3,4-dichlorophenyl)-N-[(4-fluorophenyl)methyl]-2,5-dimethyl-pyrazolo[1,5-a]pyrimidin-7-amine,
N-[(4-fluorophenyl)methyl]-2,5-dimethyl-3-[4-(trifluoromethyl)phenyl]pyrazolo[1,5-a]pyrimidin-7-amine,
N-[(4-fluorophenyl)methyl]-2,5-dimethyl-3-(3,4,5-trimethoxyphenyl)pyrazolo[1,5-a]pyrimidin-7-amine,
3-(3,4-difluorophenyl)-N-[(4-fluorophenyl)methyl]-2,5-dimethyl-pyrazolo[1,5-a]pyrimidin-7-amine,
methyl 4-[7-[(4-fluorophenyl)methylamino]-2,5-dimethyl-pyrazolo[1,5-a]pyrimidin-3-yl]benzoate
3-(3-fluoro-4-methoxy-phenyl)-2,5-dimethyl-N-(p-tolylmethyl)pyrazolo[1,5-a]pyrimidin-7-amine,
3-(3,4-diethoxyphenyl)-N-[(4-fluorophenyl)methyl]-2,5-dimethyl-pyrazolo[1,5-a]pyrimidin-7-amine,
4-[2,5-dimethyl-7-(p-tolylmethylamino)pyrazolo[1,5-a]pyrimidin-3-yl]benzene-1,2-diol,
3-(3,4-dimethoxyphenyl)-N-[(4-fluorophenyl)methyl]-5-isopropyl-2-methyl-pyrazolo[1,5-a]pyrimidin-7-amine, and
N-[(4-fluorophenyl)methyl]-2,5-dimethyl-3-(4-pyridyl)pyrazolo[1,5-a]pyrimidin-7-amine,
or a pharmaceutically acceptable salt thereof.

7. A compound of formula (Id)

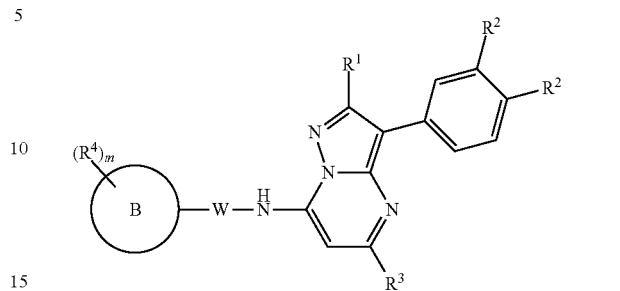

(Id)

or a pharmaceutically acceptable salt thereof,
wherein
W is

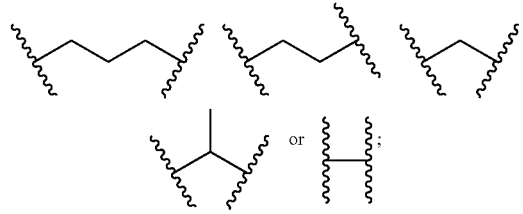

$R^1$ is H or C1-C6 alkyl,
each $R^2$ is independently selected from C1-C6 alkyl, $R^5O-$, $R^6R^7NC(O)-$, $R^9C(O)N(R^8)-$, $R^{10}OC(O)-$, $R^{11}C(O)O-$, and halogen;
$R^5$, $R^6$, $R^7$ and $R^8$ are independently selected from H and C1-C6 alkyl;
$R^9$, $R^{10}$ and $R^{11}$ are independently selected from C1-6 alkyl;
any alkyl is optionally substituted by one or more F; or
two $R^2$ together form a methylenedioxy or ethylenedioxy biradical;
$R^3$ is C1-C6 alkyl;
m is an integer of from 0 to 2;
each $R^4$ is independently selected from C1-C6 alkyl, $R^{12}O$, halogen, $R^{13}R^{14}NC(O)-$, $R^{16}C(O)N(R^{15})-$, $R^{17}OC(O)-$, $R^{18}C(O)O-$, $R^{19}S(O)_2-$, $R^{20}S(O)_2N(H)-$, $NH_2S(O)_2-$, $R^{21}C(O)-$, $N(R^{22})(R^{23})-$, and $-O-$;
$R^{12}$, $R^{13}$, $R^{14}$, $R^{15}$, $R^{22}$, and $R^{23}$ are independently selected from H and C1-C6 alkyl,
$R^{16}$, $R^{17}$, $R^{18}$, $^{19}$, $R^{20}$, and $R^{21}$ are independently selected from C1-6 alkyl;
any alkyl is optionally substituted by one or more F; or
two $R^4$ attached to adjacent atoms of ring B form, together with the atoms to which they are attached, a 5- or 6-membered heterocyclic or carbocyclic ring, or a benzene ring;
ring B is a 5- or 6-membered heteroaryl or phenyl;
provided that the compound is not:
N-[(4-chlorophenyl)methyl]-3-(3,4-dimethoxyphenyl)-2,5-dimethyl-pyrazolo[1,5-a]pyrimidin-7-amine,
3-(3,4-dimethoxyphenyl)-N-[(4-methoxyphenyl)methyl]-2,5-dimethyl-pyrazolo[1,5-a]pyrimidin-7-amine, N-[2-(4-chlorophenyl)ethyl]-3-(3,4-dimethoxyphenyl)-2,5-dimethyl-pyrazolo[1,5-a]pyrimidin-7-amine,
3-(3,4-dimethoxyphenyl)-2,5-dimethyl-N-(p-tolylmethyl)pyrazolo[1,5-a]pyrimidin-7-amine,
3-(3,4-dimethoxyphenyl)-2,5-dimethyl-N-(3-phenylpropyl)pyrazolo[1,5-a]pyrimidin-7-amine,
N-(1,3-benzodioxol-5-ylmethyl)-3-(3,4-dimethoxyphenyl)-2,5-dimethyl-pyrazolo[1,5-a]pyrimidin-7-amine,
3-(3,4-dimethoxyphenyl)-N-[(4-fluorophenyl)methyl]-2,5-dimethyl-pyrazolo[1,5-a]pyrimidin-7-amine,
3-(3,4-dimethoxyphenyl)-2,5-dimethyl-N-(2-phenylpropyl)pyrazolo[1,5-a]pyrimidin-7-amine,
3-(3,4-dimethoxyphenyl)-N-[2-(2,4-dimethoxyphenyl)ethyl]-2,5-dimethyl-pyrazolo[1,5-a]pyrimidin-7-amine,
3-(3,4-dimethoxyphenyl)-2,5-dimethyl-N-(2-pyridylmethyl)pyrazolo[1,5-a]pyrimidin-7-amine,
N-benzyl-3-(3,4-dimethoxyphenyl)-2,5-dimethyl-pyrazolo[1,5-a]pyrimidin-7-amine,
N-(4-bromophenyl)-3-(3,4-dimethoxyphenyl)-2,5-dimethyl-pyrazolo[1,5-a]pyrimidin-7-amine,
N-(4-chlorophenyl)-3-(3,4-dimethoxyphenyl)-2,5-dimethyl-pyrazolo[1,5-a]pyrimidin-7-amine,
3-(3,4-dimethoxyphenyl)-2,5-dimethyl-N-(p-tolyl)pyrazolo[1,5-a]pyrimidin-7-amine,
3-(3,4-dimethoxyphenyl)-N-(4-methoxyphenyl)-2,5-dimethyl-pyrazolo[1,5-a]pyrimidin-7-amine,
3-(3,4-dimethoxyphenyl)-2,5-dimethyl-N-(m-tolyl)pyrazolo[1,5-a]pyrimidin-7-amine,
N-(3-chlorophenyl)-3-(3,4-dimethoxyphenyl)-2,5-dimethyl-pyrazolo[1,5-a]pyrimidin-7-amine,
3-(3,4-dimethoxyphenyl)-N-(3,4-dimethylphenyl)-2,5-dimethyl-pyrazolo[1,5-a]pyrimidin-7-amine,
3-(3,4-dimethoxyphenyl)-N-(4-fluorophenyl)-2,5-dimethyl-pyrazolo[1,5-a]pyrimidin-7-amine,
3-(3,4-dimethoxyphenyl)-N-(4-ethoxyphenyl)-2,5-dimethyl-pyrazolo[1,5-a]pyrimidin-7-amine,
N-(3-chloro-4-methyl-phenyl)-3-(3,4-dimethoxyphenyl)-2,5-dimethyl-pyrazolo[1,5-a]pyrimidin-7-amine,
3-(3,4-dimethoxyphenyl)-N-(3,5-dimethylphenyl)-2,5-dimethyl-pyrazolo[1,5-a]pyrimidin-7-amine,
3-(3,4-dimethoxyphenyl)-2,5-dimethyl-N-phenyl-pyrazolo[1,5-a]pyrimidin-7-amine,
N-[4-[[3-(3,4-dimethoxy phenyl)-2,5-dimethyl-pyrazolo[1,5-a]pyrimidin-7-yl]amino]phenyl]acetamide
N-(3,4-dichlorophenyl)-3-(3,4-dimethoxyphenyl)-2,5-dimethyl-pyrazolo[1,5-a]pyrimidin-7-amine,
3-(3,4-dimethoxyphenyl)-N-(4-isopropylphenyl)-2,5-dimethyl-pyrazolo[1,5-a]pyrimidin-7-amine,
3-(3,4-dimethoxyphenyl)-N-(3-methoxyphenyl)-2,5-dimethyl-pyrazolo[1,5-a]pyrimidin-7-amine
3-(3,4-dimethoxyphenyl)-N-(4-ethylphenyl)-2,5-dimethyl-pyrazolo[1,5-a]pyrimidin-7-amine,
N-(4-butylphenyl)-3-(3,4-dimethoxyphenyl)-2,5-dimethyl-pyrazolo[1,5-a]pyrimidin-7-amine, or
N-(3,5-dichlorophenyl)-3-(3,4-dimethoxyphenyl)-2,5-dimethyl-pyrazolo[1,5-a]pyrimidin-7-amine.

8. The compound of claim 7 or a pharmaceutically acceptable salt thereof, wherein W is

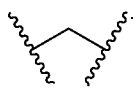

9. A compound of formula (Ih)

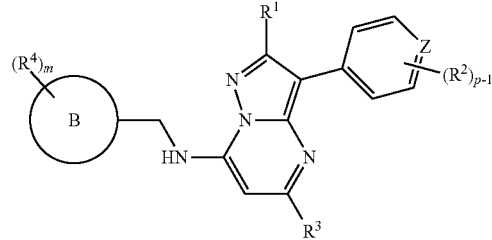

or a pharmaceutically acceptable salt thereof, wherein
p is an integer of from 1 to 3;
Z is N or $CR^2$;
$R^1$ is H or C1-C6 alkyl;
each $R^2$ is independently selected from C1-C6 alkyl, $R^5O$—, $R^6R^7NC(O)$—, $R^9C(O)N(R^8)$—, $R^{10}OC(O)$—, $R^{11}C(O)O$—, and halogen;
$R^5$, $R^6$, $R^7$ and $R^8$ are independently selected from H and C1-C6 alkyl;
$R^9$, $R^{10}$ and $R^{11}$ are independently selected from C1-6 alkyl;
any alkyl is optionally substituted by one or more F; or
two $R^2$ together form a methylenedioxy or ethylenedioxy biradical;
no $R^2$ is attached in ortho position on the phenyl ring;
$R^3$ is C1-C6 alkyl;
m is an integer of from 0 to 2;
each $R^4$ is independently selected from C1-C6 alkyl, $R^{12}O$, halogen, $R^{13}R^{14}NC(O)$—, $R^{16}C(O)N(R^{15})$—, $R^{17}OC(O)$—, $R^{18}C(O)O$—, $R^{19}S(O)_2$—, $R^{20}S(O)_2N(H)$—, $NH_2S(O)_2$—, $R^{21}C(O)$—, $N(R^{22})(R^{23})$—, and $^-O$—;
$R^{12}$, $R^{13}$, $R^{14}$, $R^{15}$, $R^{22}$, and $R^{23}$ are independently selected from H and C1-C6 alkyl,
$R^{16}$, $R^{17}$, $R^{18}$, $R^{19}$, $R^{20}$, and $R^{21}$ are independently selected from C1-6 alkyl;
any alkyl is optionally substituted by one or more F; or
two $R^4$ attached to adjacent atoms of ring B form, together with the atoms to which they are attached, a 5- or 6-membered heterocyclic or carbocyclic ring, or a benzene ring;
ring B is a 5- or 6-membered heteroaryl or phenyl;
provided that the compound is not:
N-benzyl-2,5-dimethyl-3-(p-tolyl)pyrazolo[1,5-a]pyrimidin-7-amine,
3-(4-methoxyphenyl)-2,5-dimethyl-N-(pyridin-3-ylmethyl)pyrazolo[1,5-a]pyrimidin-7-amine,
3-(4-methoxyphenyl)-2,5-dimethyl-N-(pyridin-4-ylmethyl)pyrazolo[1,5-a]pyrimidin-7-amine,
N-[(4-chlorophenyl)methyl]-3-(3,4-dimethoxyphenyl)-2,5-dimethyl-pyrazolo[1,5-a]pyrimidin-7-amine,
3-(3,4-dimethoxyphenyl)-N-[(4-methoxyphenyl)methyl]-2,5-dimethyl-pyrazolo[1,5-a]pyrimidin-7-amine,
3-(3,4-dimethoxyphenyl)-2,5-dimethyl-N-(p-tolylmethyl)pyrazolo[1,5-a]pyrimidin-7-amine,
N-(1,3-benzodioxol-5-ylmethyl)-3-(3,4-dimethoxyphenyl)-2,5-dimethyl-pyrazolo[1,5-a]pyrimidin-7-amine,
3-(3,4-dimethoxyphenyl)-N-[(4-fluorophenyl)methyl]-2,5-dimethyl-pyrazolo[1,5-a]pyrimidin-7-amine,
N-benzyl-3-(4-fluorophenyl)-2,5-dimethyl-pyrazolo[1,5-a]pyrimidin-7-amine,
N-benzyl-3-(4-fluorophenyl)-5-methyl-pyrazolo[1,5-a]pyrimidin-7-amine, N-benzyl-3-(4-chlorophenyl)-5-methyl-pyrazolo[1,5-a]pyrimidin-7-amine,
2,5-dimethyl-3-(p-tolyl)-N-(2-pyridylmethyl)pyrazolo[1,5-a]pyrimidin-7-amine,
2,5-dimethyl-3-(p-tolyl)-N-(3-pyridylmethyl)pyrazolo[1,5-a]pyrimidin-7-amine,
3-(3,4-dimethoxyphenyl)-2,5-dimethyl-N-(2-pyridylmethyl)pyrazolo[1,5-a]pyrimidin-7-amine,
3-(4-fluorophenyl)-2,5-dimethyl-N-(3-pyridylmethyl)pyrazolo[1,5-a]pyrimidin-7-amine,
3-(4-fluorophenyl)-2,5-dimethyl-N-(2-pyridylmethyl)pyrazolo[1,5-a]pyrimidin-7-amine,
N-benzyl-3-(3,4-dimethoxyphenyl)-2,5-dimethyl-pyrazolo[1,5-a]pyrimidin-7-amine,
3-(4-chlorophenyl)-2,5-dimethyl-N-(2-pyridylmethyl)pyrazolo[1,5-a]pyrimidin-7-amine,
3-(4-chlorophenyl)-2,5-dimethyl-N-(3-pyridylmethyl)pyrazolo[1,5-a]pyrimidin-7-amine,
3-(4-methoxyphenyl)-2,5-dimethyl-N-(3-pyridylmethyl)pyrazolo[1,5-a]pyrimidin-7-amine, or
3-(4-methoxyphenyl)-2,5-dimethyl-N-(4-pyridylmethyl)pyrazolo[1,5-a]pyrimidin-7-amine.

10. The compound of claim 9, or a pharmaceutically acceptable salt thereof, wherein Z is $CR^2$.

11. The compound of claim 7, or a pharmaceutically acceptable salt thereof, wherein the ring B is phenyl.

12. The compound of claim 7, or a pharmaceutically acceptable salt thereof, wherein the ring B is 5- or 6-membered heteroaryl.

13. A compound according to claim 7, selected from
3-(3,4-dimethoxyphenyl)-2,5-dimethyl-N-[[4-(trifluoromethyl)phenyl]methyl]pyrazolo[1,5-a]pyrimidin-7-amine,
3-(3,4-dimethoxyphenyl)-2,5-dimethyl-N-[4-(trifluoromethyl)phenyl]pyrazolo[1,5-a]pyrimidin-7-amine,
3-(3,4-dimethoxyphenyl)-2,5-dimethyl-N-(4-pyridyl)pyrazolo[1,5-a]pyrimidin-7-amine,
3-(3,4-dimethoxyphenyl)-2,5-dimethyl-N-(4-pyridylmethyl)pyrazolo[1,5-a]pyrimidin-7-amine,
3-(3,4-dimethoxyphenyl)-2,5-dimethyl-N-[[4-(trifluoromethoxy)phenyl]methyl]pyrazolo[1,5-a]pyrimidin-7-amine,
N-[4-[[[3-(3,4-dimethoxyphenyl)-2,5-dimethyl-pyrazolo[1,5-a]pyrimidin-7-yl]amino]methyl]phenyl]acetamide,
3-(3,4-dimethoxyphenyl)-N-[(4-dimethylaminophenyl)methyl]-2,5-dimethyl-pyrazolo[1,5-a]pyrimidin-7-amine,
3-(3,4-dimethoxyphenyl)-N-[(6-methoxy-3-pyridyl)methyl]-2,5-dimethyl-pyrazolo[1,5-a]pyrimidin-7-amine,
N-[4-[[[3-(3,4-dimethoxyphenyl)-2,5-dimethyl-pyrazolo[1,5-a]pyrimidin-7-yl]amino]methyl]phenyl]methanesulfonamide,
4-[[[3-(3,4-dimethoxyphenyl)-2,5-dimethyl-pyrazolo[1,5-a]pyrimidin-7-yl]amino]methyl]phenol,
3-(3,4-dimethoxyphenyl)-2,5-dimethyl-N-[(3-methylsulfonylphenyl)methyl]pyrazolo[1,5-a]pyrimidin-7-amine,
3-(3,4-dimethoxyphenyl)-2,5-dimethyl-N-[(1-oxidopyridin-1-ium-4-yl)methyl]pyrazolo[1,5-a]pyrimidin-7-amine,
3-(3,4-dimethoxyphenyl)-2,5-dimethyl-N-[(4-methylsulfonylphenyl)methyl]pyrazolo[1,5-a]pyrimidin-7-amine,
3-(3,4-dimethoxyphenyl)-2,5-dimethyl-N-[2-(2-pyridyl)ethyl]pyrazolo[1,5-a]pyrimidin-7-amine,
N-[(4-tert-butylphenyl)methyl]-3-(3,4-dimethoxyphenyl)-2,5-dimethyl-pyrazolo[1,5-a]pyrimidin-7-amine,
3-(3,4-dimethoxyphenyl)-2,5-dimethyl-N-[(2-methylpyrimidin-4-yl)methyl]pyrazolo[1,5-a]pyrimidin-7-amine,
3-(3,4-dimethoxyphenyl)-2,5-dimethyl-N-[2-(2-thienyl)ethyl]pyrazolo[1,5-a]pyrimidin-7-amine,
3-(3,4-dimethoxyphenyl)-2,5-dimethyl-N-[2-(4-pyridyl)ethyl]pyrazolo[1,5-a]pyrimidin-7-amine,
3-(3,4-dimethoxyphenyl)-2,5-dimethyl-N-pyrazin-2-yl-pyrazolo[1,5-a]pyrimidin-7-amine,
3-(3,4-dimethoxyphenyl)-N-indan-2-yl-2,5-dimethyl-pyrazolo[1,5-a]pyrimidin-7-amine,
3-(3,4-dimethoxyphenyl)-2,5-dimethyl-N-[(6-methyl-3-pyridyl)methyl]pyrazolo[1,5-a]pyrimidin-7-amine,
N-[3-(3,4-dimethoxyphenyl)-2,5-dimethyl-pyrazolo[1,5-a]pyrimidin-7-yl]-5-methyl-thiazol-2-amine,
1-[4-[[[3-(3,4-dimethoxyphenyl)-2,5-dimethyl-pyrazolo[1,5-a]pyrimidin-7-yl]amino]methyl]phenyl]ethanone,
N-[3-(3,4-dimethoxyphenyl)-2,5-dimethyl-pyrazolo[1,5-a]pyrimidin-7-yl]isoxazol-3-amine,
3-(3,4-dimethoxyphenyl)-2,5-dimethyl-N-(1-naphthylmethyl)pyrazolo[1,5-a]pyrimidin-7-amine,
4-[[[3-(3,4-dimethoxyphenyl)-2,5-dimethyl-pyrazolo[1,5-a]pyrimidin-7-yl]amino]methyl]benzenesulfonamide,
3-(3,4-dimethoxyphenyl)-N-[(4-fluorophenyl)methyl]-5-methyl-pyrazolo[1,5-a]pyrimidin-7-amine,
3-(3,4-dimethoxyphenyl)-2,5-dimethyl-N-[1-(4-pyridyl)ethyl]pyrazolo[1,5-a]pyrimidin-7-amine,
3-(3,4-dimethoxyphenyl)-5-methyl-N-(4-pyridylmethyl)pyrazolo[1,5-a]pyrimidin-7-amine,
3-(3,4-dimethoxyphenyl)-5-methyl-N-[(3-methylsulfonylphenyl)methyl]pyrazolo[1,5-a]pyrimidin-7-amine,
3-(1,3-benzodioxol-5-yl)-N-[(4-fluorophenyl)methyl]-2,5-dimethyl-pyrazolo[1,5-a]pyrimidin-7-amine,
3-(3,4-dichlorophenyl)-N-[(4-fluorophenyl)methyl]-2,5-dimethyl-pyrazolo[1,5-a]pyrimidin-7-amine,
3-(3,4-difluorophenyl)-N-[(4-fluorophenyl)methyl]-2,5-dimethyl-pyrazolo[1,5-a]pyrimidin-7-amine,
3-(3-fluoro-4-methoxy-phenyl)-2,5-dimethyl-N-(p-tolylmethyl)pyrazolo[1,5-a]pyrimidin-7-amine,
3-(3,4-diethoxyphenyl)-N-[(4-fluorophenyl)methyl]-2,5-dimethyl-pyrazolo[1,5-a]pyrimidin-7-amine,
4-[2,5-dimethyl-7-(p-tolylmethylamino)pyrazolo[1,5-a]pyrimidin-3-yl]benzene-1,2-diol, and
3-(3,4-dimethoxyphenyl)-N-[(4-fluorophenyl)methyl]-5-isopropyl-2-methyl-pyrazolo[1,5-a]pyrimidin-7-amine, or a pharmaceutically acceptable salt thereof.

14. A compound according to claim 9, selected from
3-(3,4-dimethoxyphenyl)-2,5-dimethyl-N-[[4-(trifluoromethyl)phenyl]methyl]pyrazolo[1,5-a]pyrimidin-7-amine,
3-(3,4-dimethoxyphenyl)-2,5-dimethyl-N-(4-pyridylmethyl)pyrazolo[1,5-a]pyrimidin-7-amine,
3-(3,4-dimethoxyphenyl)-2,5-dimethyl-N-[[4-(trifluoromethoxy)phenyl]methyl]pyrazolo[1,5-a]pyrimidin-7-amine,
N-[4-[[[3-(3,4-dimethoxyphenyl)-2,5-dimethyl-pyrazolo[1,5-a]pyrimidin-7-yl]amino]methyl]phenyl]acetamide,
3-(3,4-dimethoxyphenyl)-N-[(4-dimethylaminophenyl)methyl]-2,5-dimethyl-pyrazolo[1,5-a]pyrimidin-7-amine,
3-(3,4-dimethoxyphenyl)-N-[(6-methoxy-3-pyridyl)methyl]-2,5-dimethyl-pyrazolo[1,5-a]pyrimidin-7-amine, N-[4-[[[3-(3,4-dimethoxyphenyl)-2,5-dimethyl-pyrazolo[1,5-a]pyrimidin-7-yl]amino]methyl]phenyl]methanesulfonamide,
4-[[[3-(3,4-dimethoxyphenyl)-2,5-dimethyl-pyrazolo[1,5-a]pyrimidin-7-yl]amino]methyl]phenol,
3-(3,4-dimethoxyphenyl)-2,5-dimethyl-N-[(3-methylsulfonylphenyl)methyl]pyrazolo[1,5-a]pyrimidin-7-amine,
3-(3,4-dimethoxyphenyl)-2,5-dimethyl-N-[(1-oxidopyridin-1-ium-4-yl)methyl]pyrazolo[1,5-a]pyrimidin-7-amine,
3-(3,4-dimethoxyphenyl)-2,5-dimethyl-N-[(4-methylsulfonylphenyl)methyl]pyrazolo[1,5-a]pyrimidin-7-amine,
N-[(4-tert-butylphenyl)methyl]-3-(3,4-dimethoxyphenyl)-2,5-dimethyl-pyrazolo[1,5-a]pyrimidin-7-amine,
3-(3,4-dimethoxyphenyl)-2,5-dimethyl-N-[(2-methylpyrimidin-4-yl)methyl]pyrazolo[1,5-a]pyrimidin-7-amine,
3-(3,4-dimethoxyphenyl)-2,5-dimethyl-N-[(6-methyl-3-pyridyl)methyl]pyrazolo[1,5-a]pyrimidin-7-amine,
1-[4-[[[3-(3,4-dimethoxyphenyl)-2,5-dimethyl-pyrazolo[1,5-a]pyrimidin-7-yl]amino]methyl]phenyl]ethanone,
3-(3,4-dimethoxyphenyl)-2,5-dimethyl-N-(1-naphthylmethyl)pyrazolo[1,5-a]pyrimidin-7-amine,
4-[[[3-(3,4-dimethoxyphenyl)-2,5-dimethyl-pyrazolo[1,5-a]pyrimidin-7-yl]amino]methyl]benzenesulfonamide,
3-(3,4-dimethoxyphenyl)-2,5-dimethyl-N-[1-(4-pyridyl)ethyl]pyrazolo[1,5-a]pyrimidin-7-amine,
3-(3,4-dimethoxyphenyl)-5-methyl-N-(4-pyridylmethyl)pyrazolo[1,5-a]pyrimidin-7-amine,
3-(3,4-dimethoxyphenyl)-5-methyl-N-[(3-methylsulfonylphenyl)methyl]pyrazolo[1,5-a]pyrimidin-7-amine,
3-(1,3-benzodioxol-5-yl)-N-[(4-fluorophenyl)methyl]-2,5-dimethyl-pyrazolo[1,5-a]pyrimidin-7-amine,
3-(3,4-dichlorophenyl)-N-[(4-fluorophenyl)methyl]-2,5-dimethyl-pyrazolo[1,5-a]pyrimidin-7-amine,
N-[(4-fluorophenyl)methyl]-2,5-dimethyl-3-[4-(trifluoromethyl)phenyl]pyrazolo[1,5-a]pyrimidin-7-amine,
N-[(4-fluorophenyl)methyl]-2,5-dimethyl-3-(3,4,5-trimethoxyphenyl)pyrazolo[1,5-a]pyrimidin-7-amine,
3-(3,4-difluorophenyl)-N-[(4-fluorophenyl)methyl]-2,5-dimethyl-pyrazolo[1,5-a]pyrimidin-7-amine,
methyl 4-[7-[(4-fluorophenyl)methylamino]-2,5-dimethyl-pyrazolo[1,5-a]pyrimidin-3-yl]benzoate,
3-(3-fluoro-4-methoxy-phenyl)-2,5-dimethyl-N-(p-tolylmethyl)pyrazolo[1,5-a]pyrimidin-7-amine,
3-(3,4-diethoxyphenyl)-N-[(4-fluorophenyl)methyl]-2,5-dimethyl-pyrazolo[1,5-a]pyrimidin-7-amine,
4-[2,5-dimethyl-7-(p-tolylmethylamino)pyrazolo[1,5-a]pyrimidin-3-yl]benzene-1,2-diol,
3-(3,4-dimethoxyphenyl)-N-[(4-fluorophenyl)methyl]-5-isopropyl-2-methyl-pyrazolo[1,5-a]pyrimidin-7-amine, and
N-[(4-fluorophenyl)methyl]-2,5-dimethyl-3-(4-pyridyl)pyrazolo[1,5-a]pyrimidin-7-amine,
or a pharmaceutically acceptable salt thereof.

15. A pharmaceutical composition comprising a compound according to claim 7, and optionally a pharmaceutically acceptable excipient.

16. A method of treatment of a viral infection, by administration of a therapeutically effective amount of a compound according to claim 7, to a mammal in need thereof.

17. A method of treatment of a viral infection, by administration of a therapeutically effective amount of a compound of formula (I)

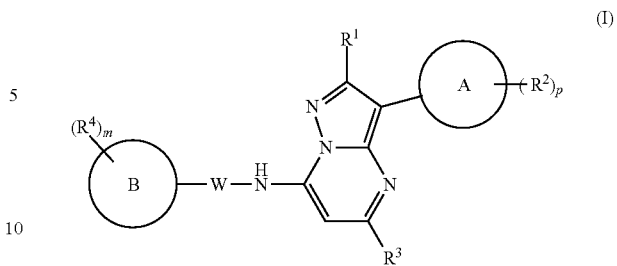

or a pharmaceutically acceptable salt thereof, wherein W is

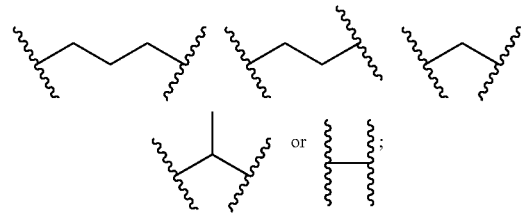

p is an integer of from 0 to 3,
$R^1$ is H or C1-C6 alkyl,
ring A is phenyl or 5- or 6-membered heteroaryl;
when ring A is phenyl, said phenyl is not substituted in ortho position;
each $R^2$ is independently selected from C1-C6 alkyl, $R^5O-$, $R^6R^7NC(O)-$, $R^9C(O)N(R^8)-$, $R^{10}OC(O)-$, $R^{11}C(O)O-$, and halogen;
$R^5$, $R^6$, $R^7$ and $R^8$ are independently selected from H and C1-C6 alkyl;
$R^9$, $R^{10}$ and $R^{11}$ are independently selected from C1-6 alkyl;
any alkyl is optionally substituted by one or more F; or
two $R^2$ attached to adjacent carbon atoms together form a methylenedioxy or ethylenedioxy biradical;
$R^3$ is C1-C6 alkyl;
m is an integer of from 0 to 2;
each $R^4$ is independently selected from C1-C6 alkyl, $R^{12}O$, halogen, $R^{13}R^{14}NC(O)-$, $R^{16}C(O)N(R^{15})-$, $R^{17}OC(O)-$, $R^{18}C(O)O-$, $R^{19}S(O)_2-$, $R^{20}S(O)_2N(H)-$, $NH_2S(O)_2-$, $R^{21}C(O)-$, $N(R^{22})(R^{23})-$, and $^-O-$;
$R^{12}$, $R^{13}$, $R^{14}$, $R^{15}$, $R^{22}$, and $R^{23}$ are independently selected from H and C1-C6 alkyl,
$R^{16}$, $R^{17}$, $R^{18}$, $^{19}$, $R^{20}$, and $R^{21}$ are independently selected from C1-6 alkyl;
any alkyl is optionally substituted by one or more F; or
two $R^4$ attached to adjacent atoms of ring B form, together with the atoms to which they are attached, a 5- or 6-membered heterocyclic or carbocyclic ring, or a benzene ring;
ring B is a 5- or 6-membered saturated or unsaturated carbocyclyl, 5- or 6-membered heteroaryl, or phenyl;
to a mammal in need thereof, provided that the compound is not:
N-(cyclohexylmethyl)-2,5-dimethyl-3-(p-tolyl)pyrazolo[1,5-a]pyrimidin-7-amine,
2,5-dimethyl-N-phenyl-3-(p-tolyl)pyrazolo[1,5-a]pyrimidin-7-amine, N-benzyl-2,5-dimethyl-3-(p-tolyl)pyrazolo[1,5-a]pyrimidin-7-amine, or 2,5-dimethyl-N-phenethyl-3-(p-tolyl)pyrazolo[1,5-a]pyrimidin-7-amine.

18. The method according to claim 16, wherein the viral infection is an RNA viral infection.

19. A method of treatment of a viral infection by administering, to a mammal in need thereof, a therapeutically effective amount of a composition according to claim 1.

20. The method according to claim 17, wherein the viral infection is an RNA viral infection.

21. The method according to claim 19, wherein the viral infection is an RNA viral infection.

* * * * *